(12) United States Patent
Worgall et al.

(10) Patent No.: US 10,159,678 B2
(45) Date of Patent: Dec. 25, 2018

(54) METHODS TO DECREASE SUSCEPTIBILITY TO ASTHMATIC BRONCHOCONSTRICTION

(71) Applicants: Cornell University, Ithaca, NY (US); Columbia University, New York, NY (US)

(72) Inventors: Stefan Worgall, New York, NY (US); Tilla S. Worgall, New York, NY (US)

(73) Assignees: Cornell University, Ithaca, NY (US); Columbia University, New York, NY (US)

( * ) Notice: Subject to any disclaimer, the term of this patent is extended or adjusted under 35 U.S.C. 154(b) by 49 days.

(21) Appl. No.: 14/400,887

(22) PCT Filed: May 16, 2013

(86) PCT No.: PCT/US2013/041375
§ 371 (c)(1),
(2) Date: Nov. 13, 2014

(87) PCT Pub. No.: WO2013/173595
PCT Pub. Date: Nov. 21, 2013

(65) Prior Publication Data
US 2015/0139915 A1    May 21, 2015

Related U.S. Application Data

(60) Provisional application No. 61/647,955, filed on May 16, 2012.

(51) Int. Cl.

| | | |
|---|---|---|
| *A61K 31/5383* | (2006.01) | |
| *A61K 31/353* | (2006.01) | |
| *A61K 31/165* | (2006.01) | |
| *A61K 31/167* | (2006.01) | |
| *A61K 31/185* | (2006.01) | |
| *A61K 31/352* | (2006.01) | |
| *A61K 31/4245* | (2006.01) | |
| *A61K 31/426* | (2006.01) | |
| *A61K 31/427* | (2006.01) | |
| *A61K 31/519* | (2006.01) | |

(52) U.S. Cl.
CPC ........ *A61K 31/5383* (2013.01); *A61K 31/165* (2013.01); *A61K 31/167* (2013.01); *A61K 31/185* (2013.01); *A61K 31/352* (2013.01); *A61K 31/353* (2013.01); *A61K 31/426* (2013.01); *A61K 31/427* (2013.01); *A61K 31/4245* (2013.01); *A61K 31/519* (2013.01)

(58) Field of Classification Search
CPC .......................... A61K 31/5383; A61K 31/519
See application file for complete search history.

(56) References Cited

U.S. PATENT DOCUMENTS

| | | | | |
|---|---|---|---|---|
| 7,414,037 | B2 * | 8/2008 | Verkman | A01K 67/027 514/313 |
| 8,207,205 | B2 * | 6/2012 | Jones | C07D 271/04 514/364 |
| 2007/0197656 | A1 | 8/2007 | Kubow et al. | |
| 2007/0243232 | A1 * | 10/2007 | Eby, III | A61K 9/0056 424/439 |
| 2008/0269206 | A1 | 10/2008 | Russell | |
| 2011/0200583 | A1 * | 8/2011 | Hakonarson | C12Q 1/6883 424/130.1 |

FOREIGN PATENT DOCUMENTS

| | | |
|---|---|---|
| WO | WO-2011137427 A2 | 11/2011 |
| WO | WO-2013173595 A1 | 11/2013 |

OTHER PUBLICATIONS

Hamai, H. et al. "Defective CFTR increases synthesis and mass of sphingolipids that modulate membrane composition and lipid signaling", 2009, J Lipid Res, vol. 50, 1101-1108.*

"International Application Serial No. PCT/US2013/041375, International Search Report dated Oct. 21, 2013", 4 pgs.

"International Application Serial No. PCT/US2013/041375, Written Opinion dated Oct. 21, 2013", 5 pgs.

Kanagaratham, Cynthia, et al., "The protective effect of fenretinide against allergic asthma", Allergy, Asthma Clin Immunol. 6(Suppl 3), (Nov. 26, 2010), 18 pgs.

"International Application Serial No. PCT/US2013/041375, International Preliminary Report on Patentability dated Nov. 27, 2014", 7 pgs.

* cited by examiner

*Primary Examiner* — Gina C Justice
(74) *Attorney, Agent, or Firm* — Schwegman Lundberg & Woessner, P.A.

(57) ABSTRACT

Methods and compositions are described for reducing airway reactivity and the susceptibility to asthmatic bronchoconstriction that involve increasing sphingolipid content in airways and lungs of a mammalian subject.

8 Claims, 23 Drawing Sheets
Specification includes a Sequence Listing.

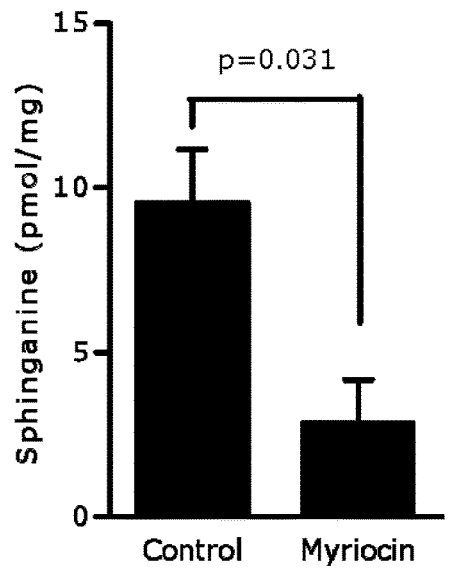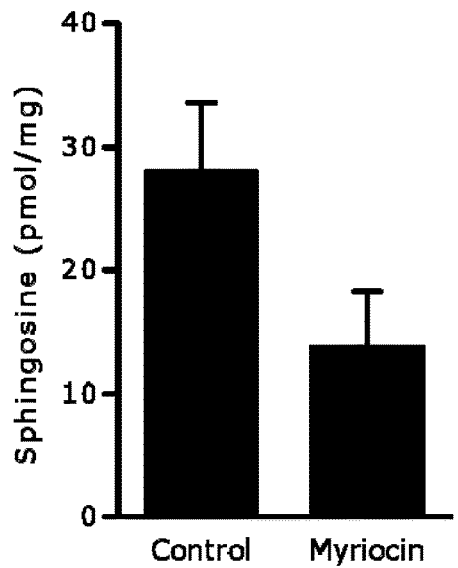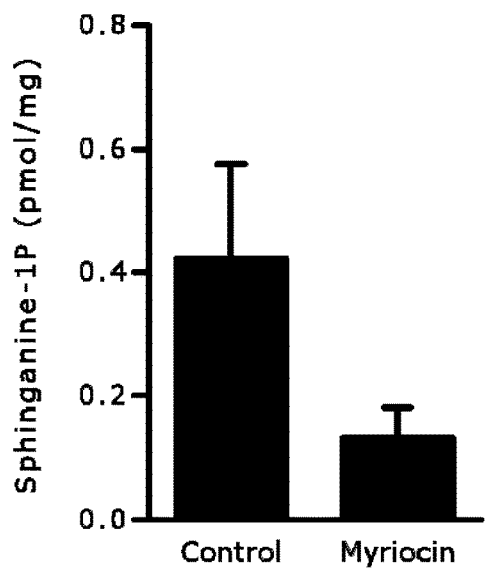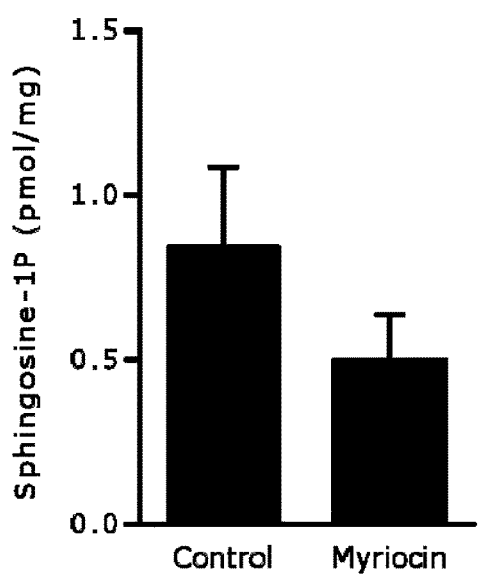
Fig. 1A    Fig. 1B
Fig. 1C    Fig. 1D

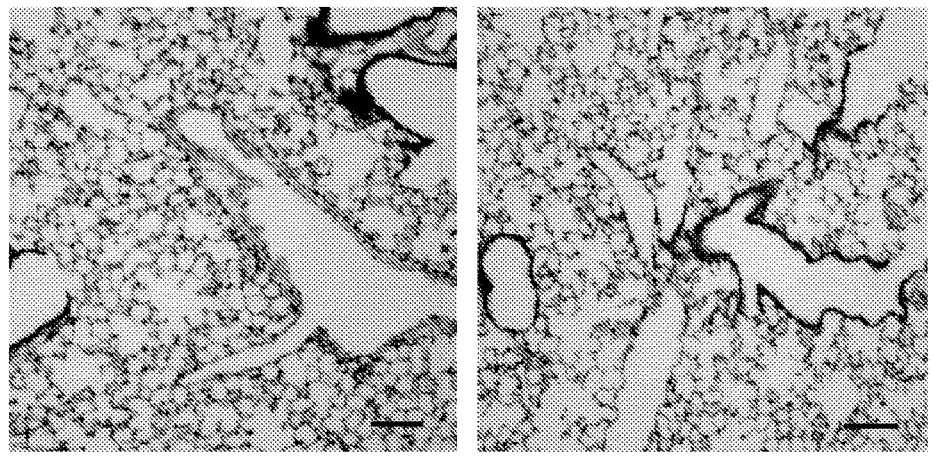
*Fig. 4C*   *Fig. 4D*
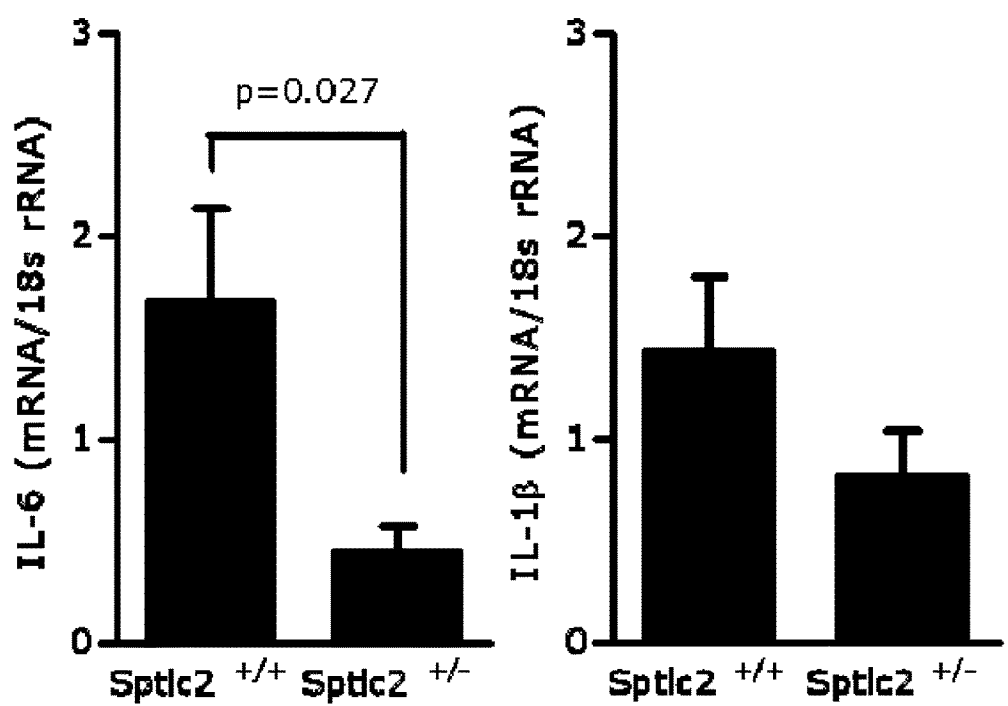
*Fig. 4E*   *Fig. 4F*

```
                        SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 1
gggaattgtc ctgtgaccag                                                  20

<210> SEQ ID NO 2
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 2
cactgtgggc aactccaac                                                   19

<210> SEQ ID NO 3
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 3
tcctggagac cacaggtgta                                                  20

<210> SEQ ID NO 4
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 4
agcttgttcc ccagctgtc                                                   19

<210> SEQ ID NO 5
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 5
ccctcaccaa ccttatccac                                                  20

<210> SEQ ID NO 6
<211> LENGTH: 19
<212> TYPE: DNA
<213> ORGANISM: Artificial Sequence
<220> FEATURE:
<223> OTHER INFORMATION: A synthetic oligonucleotide
```

```
<400> SEQUENCE: 6 ggacccccgta gtccatctg                                              19
```

METHODS TO DECREASE SUSCEPTIBILITY TO ASTHMATIC BRONCHOCONSTRICTION

RELATED APPLICATIONS

This application is a U.S. National Application filed under 35 U.S.C. § 371 from International Application Serial No. PCT/US2013/041375, which was filed May 16, 2013, and published as WO 2013/173595, on Nov. 21, 2013, which claims benefit of the filing date of U.S. Provisional Patent Application No. 61/647,955, filed May 16, 2012, the contents of which are specifically incorporated herein in their entirety.

This invention was made with government support under Grant No. UL1 RR024156 by the National Institutes of Health. The government has certain rights in the invention.

BACKGROUND

Asthma is one of the most common chronic medical conditions in the developed world and is responsible for many thousands of deaths each year. Asthma can be characterized as an obstruction of the airways which leads to chest tightness, wheezing, coughing and difficulties in breathing. Triggers for asthma episodes often include allergens, strenuous exercise, cold air, infections, exposure to atmospheric irritants and strong odors. The pathogenesis of asthma is varied and there are several biological pathways involved in the development of asthma (see R. Balkissoon, Prim. Care Clin. Office Pract., 35 (2008) 41-60). Although it is clear that both environmental and genetic influences are important in the development of asthma, the pathogenesis of this disease remains unclear.

A number of medications are currently available for treatment and prevention of asthma. For example, anti-inflammatory agents, leukotriene modifiers, long-acting beta agonists, theophylline, and inhaled corticosteroids are important asthma medications. While these medications are useful, some have side effects and many must be taken on long-term basis. Current asthma therapies are not curative and generally do not address the underlying mechanisms of asthma, because those mechanisms have not yet been identified. Some patients are well-treated by administration of one asthma drug, while other patients are not, likely because the underlying causes of asthma are multi-faceted and patient responses to stimuli are different. New treatments for prevention and management of asthma are needed.

SUMMARY

As described herein, airway constriction and the susceptibility to asthma can be reduced by increasing sphingolipid synthesis in a subject. The methods and compositions described herein increase de-novo sphingolipid synthesis in airways and/or the lungs. The methods and compositions described herein do not primarily involve modulation of sphingosine-1P levels and are not mediated by altered sphingosine-1P levels.

DESCRIPTION OF THE DRAWINGS

FIG. 1A-1G graphically illustrate sphingolipid levels in myriocin treated lungs compared to control, untreated animals. As shown, myriocin decreased SPT activity and reduced sphingolipid levels in the treated lungs. Long chain bases and ceramides of lung homogenates from myriocin treated mice (20 µg) were quantified by tandem mass spectrometry (LC-MS/MS). FIG. 1A shows sphinganine levels (pmole/mg tissue). FIG. 1B shows sphingosine levels (pmole/mg tissue). FIG. 1C shows sphinganine-1P levels (pmole/mg tissue). FIG. 1D shows sphingosine-1P levels (pmole/mg tissue). FIG. 1E shows total ceramides, the sum of Cer14, C16, Cer18, Cer20, Cer22, Cer24 and Cer24:1. FIG. 1F shows a pie chart illustrating the percentage of individual ceramides in control (untreated) animals. FIG. 1G shows a pie chart illustrating the percentage of individual ceramides in treated animals. Data shown are the mean of 7 mice tested/group; error bars show s.e.m.; the symbol * designates $p<0.05$ (unpaired t test).

FIG. 2A shows sphinganine levels (pmole/mg tissue). FIG. 2B shows sphingosine levels (pmole/mg tissue). FIG. 2C shows sphinganine-1P levels (pmole/mg tissue). FIG. 2D shows sphingosine-1P levels (pmole/mg tissue). FIG. 2E shows total ceramides, the sum of Cer14, C16, Cer18, Cer20, Cer22, Cer24 and Cer24:1. FIG. 2F shows a pie chart illustrating the percentage of individual ceramides in control (Sptlc2$^{+/+}$) animals. FIG. 2G shows a pie chart illustrating the percentage of individual ceramides in Sptlc2$^{+/-}$ animals. Data shown are the mean of 7 mice tested/group; error bars show s.e.m.; the symbol * designates $p<0.05$ (unpaired t test). FIG. 2H graphically illustrates that expression of ORMDL in the lung is not altered by treatment of mice with 20 µg myriocin. FIG. 2I graphically illustrates that expression of ORMDL in the lung is not altered in Sptlc2$^{+/-}$ mice. Expression of ORMDL1, ORMDL2 and ORMDL3 mRNA was quantified by Real-Time RT-PCR. Data shown are the mean of 5-7 mice tested/group; error bars show s.e.m.

FIG. 3A graphically illustrates airway resistance (Rn) in response to increasing doses of inhaled methacholine three hours after intranasal administration of myriocin (2 or 20 µg) to BALB/c mice. FIG. 3B illustrates static compliance of the same mice treated as described for FIG. 3A. FIG. 3C shows myograph (muscle contraction) readings on isolated bronchial rings upon administration of 1 mM methacholine (MC) after treatment with myriocin (20 µg) as described for FIG. 3A. The control rings received no myriocin. FIG. 3D shows isometric force generation in isolated bronchial rings exposed to 0.001-10 µM methacholine after treatment with myriocin (20 µg) as described for FIG. 3A. FIG. 3E shows isometric force generation of human bronchial rings isolated from unaffected parts of lungs that were resected for cancer after incubation for 2 h with methacholine in the bath solution. FIG. 3F illustrates airway resistance in response to methacholine administration to Sptlc2$^{+/-}$ mice compared to wild type controls (Sptlc2$^{+/+}$). Contractile responses for FIGS. 3D-3E are expressed as absolute force generated. FIG. 3G shows the static compliance of mice treated as described in FIG. 3F. FIG. 3H shows the contractile responses (isometric force generation) of bronchial rings isolated from Sptlc2$^{+/-}$ or Sptlc2$^{+/+}$ mice stimulated with methacholine. Data shown in FIGS. 3A-C, F and G are representative of three independent experiments, each with 5-8 mice/group; data shown in FIGS. 3E and 3H are the mean of three independent experiments; error bars show s.e.m. The symbol * signifies $p<0.05$, the symbol  signifies $p<0.001$, and the symbol * signifies $p<0.0001$ (ANOVA).

FIG. 4A-4N illustrate that reduced SPT activity in the lung is not associated with increased inflammation. FIG. 4A graphically illustrates the numbers of cells in bronchioalveolar lavage from Sptlc2$^{+/-}$ mice. FIG. 4C shows an image of an HE-stained lung section following myriocin (20 μg) treatment (bar=100 μm). FIG. 4D shows an image of an HE-stained lung section from Sptlc2$^{+/-}$ mice (bar=100 μm). FIG. 4E graphically illustrates the expression level of interleukin-6 (IL-6) in Sptlc2$^{+/-}$ mice. FIG. 4F graphically illustrates the expression level of interleukin-1β (IL-1β) in Sptlc2$^{+/-}$ mice. FIG. 4E-4J: unpaired t test). FIGS. 4K-4N show that reduced SPT activity in the lung is not associated with increased mucus production. FIG. 4K graphically illustrates expression levels of Muc5ac mRNA in the lungs of mice following myriocin treatment. FIG. 4L graphically illustrates expression levels of Muc5ac mRNA in the lungs of Sptlc2$^{+/+}$ and Sptlc2$^{+/-}$ mice. Data in FIGS. 4K and 4L show the mean of 7 mice/group; error bars show s.e.m. (unpaired t test). FIG. 4M graphically illustrates the thickness of α-SMA-positive smooth muscle cell layers in 100-200 μm airways. FIG. 4N graphically illustrates the thickness of the collagen layer in 100-200 μm bronchi.

FIG. 5A graphically illustrates expression levels of the magnesium transporter TRPM7 mRNA in lungs of Sptlc2$^{+/-}$ mice or mice that had received myriocin. FIG. 5B graphically illustrates total lung magnesium content in Sptlc2$^{+/-}$ mice and mice that had received myriocin (20 μg). FIG. 5C graphically illustrates the effects of MgSO$_4$ (15 mM) on relaxation of methacholine (MC)-induced isometric force generation of bronchial rings isolated from myriocin-treated (20 μg) mice. FIG. 5D graphically illustrates the effect of MgSO$_4$ (15 mM) on relaxation of methacholine (MC)-induced isometric force generation of bronchial rings isolated from Sptlc2$^{+/-}$ mice. Relaxation is expressed as percentage of maximum force generated before addition of MgSO$_4$. Data in FIG. 5A-D show the mean representative experiment of 5-6 mice/group; error bars show s.e.m. The symbol * designates $p<0.05$ (unpaired t test).

FIG. 6A shows that sphinganine levels increase when GlyH-101 is added to the culture media of non-cystic fibrosis airway epithelial cells (bottom two lines). Sphinganine is a sphingolipid intermediate produced only via the de-novo pathway. Cystic fibrosis airway epithelial cells (top two lines) have increased baseline levels of sphinganine that are not altered by GlyH-101. FIG. 6B shows that GlyH-101 also increases the amount of sphinganine produced when GlyH-101 is added to the culture media of A549 cells, a lung epithelial cell line. FIG. 6C shows that inhibition of CFTR by GlyH-101 ameliorates bronchial hyper-responsiveness induced by Spt deficiency. In particular, FIG. 6C shows that the contractile response of bronchial rings isolated from Sptlc2$^{+/-}$ mice is relieved by administration of GlyH-101. This effect is not seen in bronchial rings from Sptlc2$^{+/+}$ mice. FIG. 6D shows that GlyH-101 does not affect the airway resistance observed in Sptlc2$^{+/+}$ mice after intranasal administration of methacholine, a bronchoconstriction agent.

DETAILED DESCRIPTION

The invention relates to reducing symptoms and susceptibility to asthma. As described herein agents that increase sphingolipid synthesis reduce the incidence and the symptoms (e.g., bronchial hyper-reactivity and/or constriction) in a subject. Such agents include, for example, dihydroceramide reductase (also known as dihydroceramide desaturase) inhibitors, cystic fibrosis transmembrane conductance regulator (CFTR) protein inhibitors, substrates for serine palmitoyl-CoA transferase (SPT), and combinations thereof. Examples of agents useful for reducing the symptoms of asthma and the susceptibility of subjects to asthma include compounds embraced by formulae I-IV. For example, agents useful for reducing the symptoms of asthma and the susceptibility of subjects to asthma include serine, alanine, glycine, Phenyl-GlyH, GlyH 101, fenretinide, GT-11, Crofelemer, PPQ-102, BPO-27, CFTR$_{inh}$-172, Tetrazolo-172, MalH-PEG and iOWHO32.

Figure 8:
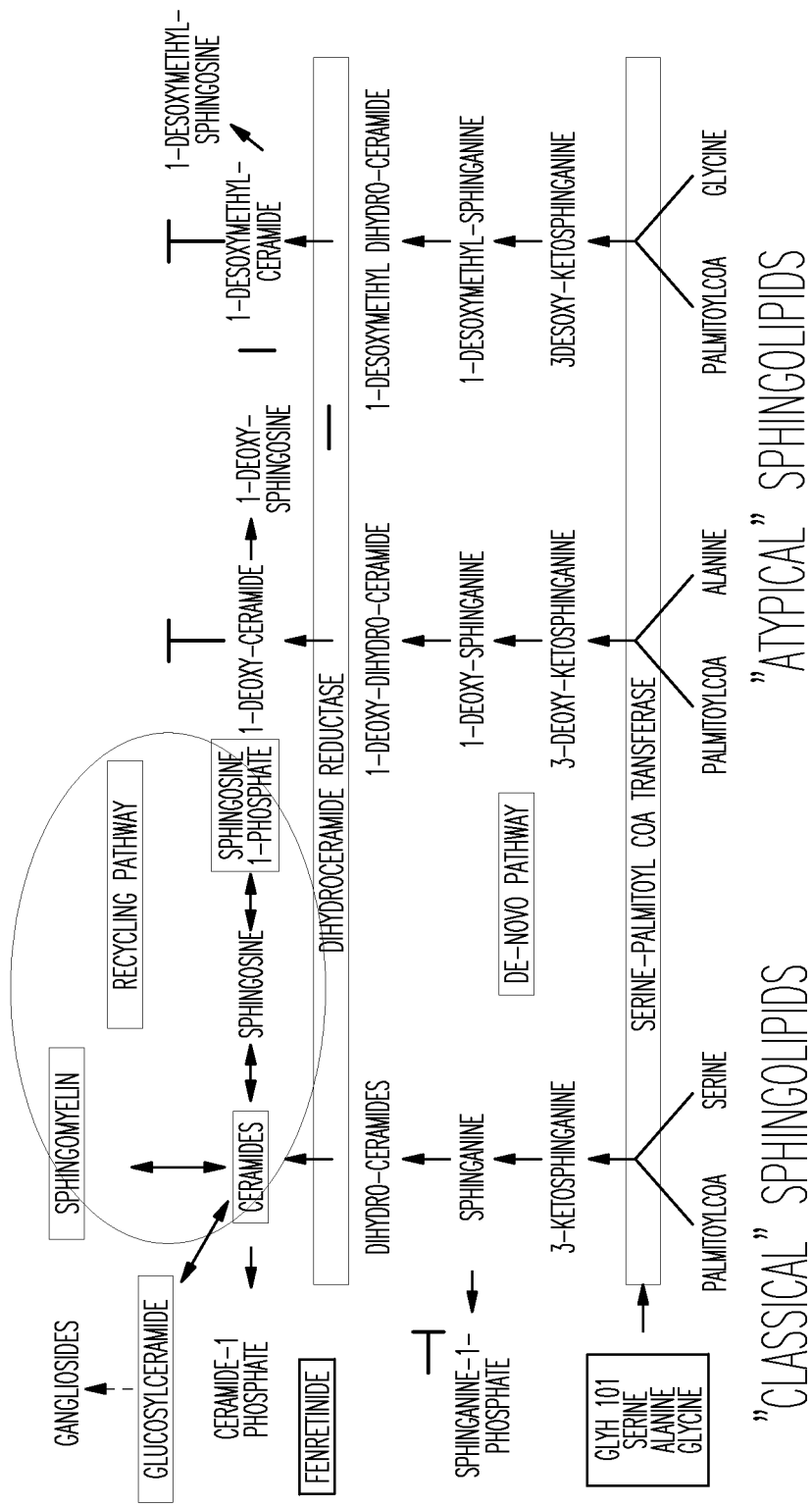
FIG. 8 is a schematic diagram of sphingolipid synthesis pathways.

Sphingolipids are a class of lipids containing a backbone of an aliphatic amino alcohol, sphingoid base such as sphingosine. The sphingosine-like backbone can be O-linked to a charged head group such as ethanolamine, serine, or choline. A fatty acid can be linked to the amino group. Examples of sphingolipids include sphingomyelins, cerebrosides, and gangliosides. FIG. 8 lists some types of sphingolipids and illustrates sphingolipid synthetic pathways.

Asthma

Asthma is a common but complex disorder, where both environmental and genetic factors influence the onset and subsequent susceptibility to the disorder. In general, asthma involves constriction and contraction of the bronchial smooth muscle. Bronchial asthma is one of the most frequent causes for hospitalization not only in adults but also in children. Even though some treatments are available, asthma is thought to be a disease for which prevention and treatment for all cases of asthma is difficult.

Polymorphisms on chromosome 17 at the 17Q21 locus have been correlated with development of asthma. For example, orosomucoid like 3 (ORMDL3) is a gene in this region that has been associated with early-onset asthma susceptibility. For example, polymorphisms such as Rs 7216389 (T allele), rs 8076131 (A allele), rs 4378650 (C allele), rs 3744246 (C allele), rs12603332 (C allele), and/or rs 3859192 (C allele) can be associated with the development of asthma (see, EP2006687, WO2008155396, and US2011046202, as well as Galanter et al., Am J Respir Crit Care Med. 177(11): 1194-1200 (2008), each of which is specifically incorporated herein in its entirety). Polymorphisms controlling ORMDL3 expression are associated with childhood asthma but not with atopy (prone to allergies), suggesting that ORMDL3 affects asthma susceptibility independent of atopic or IgE-mediated pathways (Sleiman et al., J. Allergy Clin. Immunol. 122, 1225-1227 (2008)).

ORMDL3 is a member of a gene family that encodes Orm transmembrane proteins that are anchored in the endoplasmic reticulum (ER). Orm proteins negatively regulate sphingolipid (SL) synthesis through assembly with serine palmitoyl-CoA transferase (SPT) in a homeostatic regulator complex.

SPT catalyzes the condensation of serine and fatty acid CoA to yield sphinganine, the rate limiting step of de-novo sphingolipid synthesis. FIG. 8 shows a schematic diagram of the de-novo sphingolipid pathway. The rate-limiting enzyme is serine palmitoyltransferase (SPT), which condenses serine and palmitoyl-CoA to form 3-ketosphinganine. The 3-ketosphinganine is then reduced to sphinganine (often referred to as the sphingoid base or the sphingoid backbone). Dihydroceramide synthases (CerS 1-6) selectively N-acylate sphinganine with a fatty acid acyl-chain. The fatty acid attached to sphinganine can vary not only in carbon length but also in degree of saturation. The product of such an N-acylation reaction is a dihydroceramide. Dihydroceramide reductase (also called dihydroceramide desaturase, DEGS-1) desaturates the sphingoid backbone of the dihydroceramide to yield the corresponding ceramide. Fenretinide is a stimulator of both SPT and CerS. Fenretinide is also a partial inhibitor of dihydroceramide reductase. GT-11 is a synthetic ceramide derivative that similarly inhibits dihydroceramide reductase.

Asthma-associated ORMDL3 polymorphisms can negatively regulate expression of SPT, and thereby inhibit de-novo sphingolipid synthesis. It has been suggested that ORMDL3 plays a role in epithelial cell remodeling through its effect on the sarco/endoplasmatic reticulum $C^{a2+}$ ATPase (SERCA) (Sun et al., Mol. Biol. Cell 23, 2388-2398 (2012); Siow et al., J. Biol. Chem. 287, 40198-40204 (2012), but no mechanism has yet been identified linking de-novo sphingolipid synthesis to asthma. Moreover, the consequences of altered SPT activity on lung function were previously unknown.

However, as described herein, decreased SPT activity leads to airway hyper-reactivity without associated airway remodeling, inflammation or mucus hyperplasia. In addition the data provided herein shows that decreased sphingolipid synthesis alters magnesium homeostasis that affects airway reactivity.

Compounds that Reduce Airway Constriction

As described herein agents and methods that increase sphingolipid synthesis are useful for treating asthma and reducing the susceptibility of subjects to asthma. Any compound or method that increases sphingolipid synthesis can be employed. For example, compounds that increase sphingolipid synthesis and reduce airway constriction include cystic fibrosis transmembrane conductance regulator (CFTR) inhibitors, dihydroceramide reductase inhibitors, and substrates for serine palmitoyl-CoA transferase (SPT). Dihydroceramide reductase is also known as dihydroceramide desaturase.

For example, the agent can be a compound of formula I:

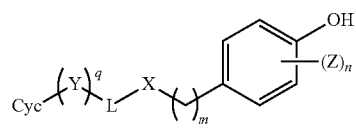

wherein:

Cyc is aryl or cycloalkyl, optionally substituted with alkyl;

Y is NH or O, and q is 0 or 1;

L is alkyl or arylalkyl, wherein any alkyl optionally comprises one or more double bond, is optionally substituted with carbonyl, or both;

X is C(O)NH—N=, C(O)NH, or NHC(O)-heteroaryl;

m is 0 or 1, provided that when m is 1 and X is C(O)NH—N=, a carbon-nitrogen double bond is present; and each independently selected Z is halo or OH, n is 0, 1, 2, or 3.

Examples of agents falling within the scope of Formula I include:

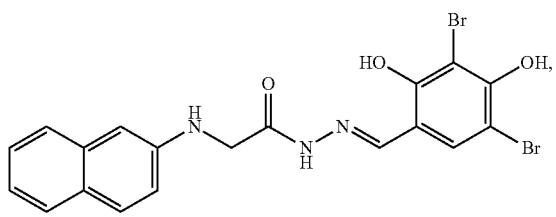

GlyH-101

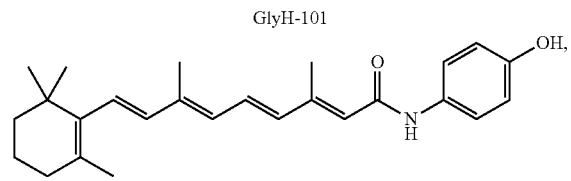

Fenretinide

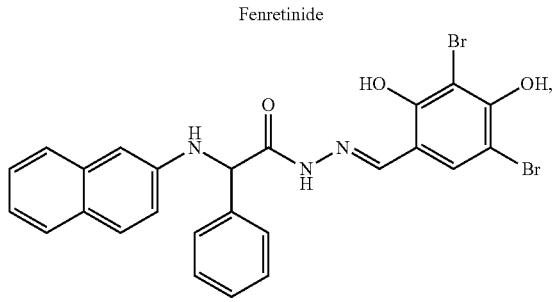

Phenyl-GlyH

-continued

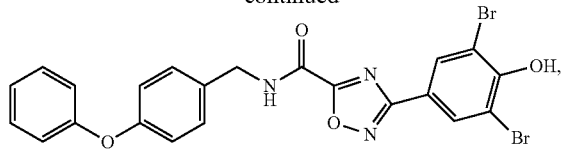

iOWH032 or
a combination thereof.
The agent can also be a compound of formula II:

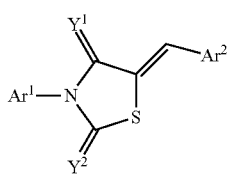

II wherein
$Y^1$ and $Y^2$ are each independently O or S;
$Ar^1$ and $Ar^2$ are each independently aryl, wherein any aryl is optionally mono- or independently multi-substituted with carboxyl, haloalkyl, or tetrazolyl.

Examples of agents falling within the scope of Formula II include:

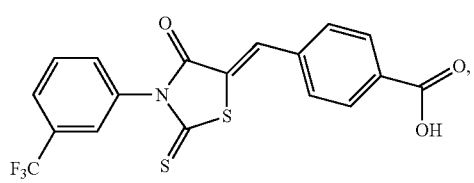

CFTR$_{inh}$-172

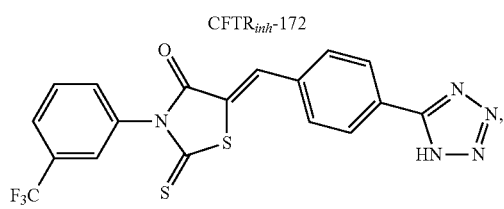

Tetrazolo-172 or
a combination thereof.
The agent can also be a compound of formula III:

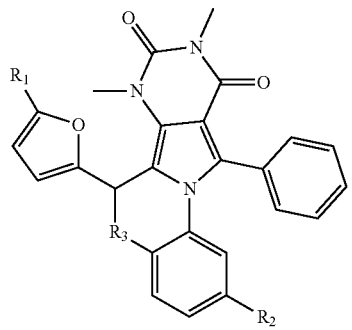

III wherein:
$R_1$ is alkyl or halo;
$R_2$ is H or carboxyl; and
$R_3$ is O or NH.

Examples of agents falling within the scope of Formula III include:

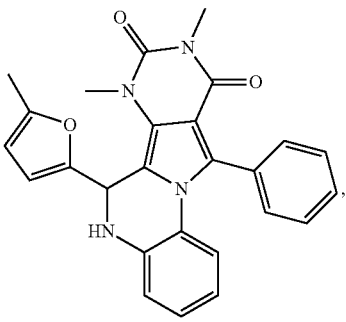

PPQ-102

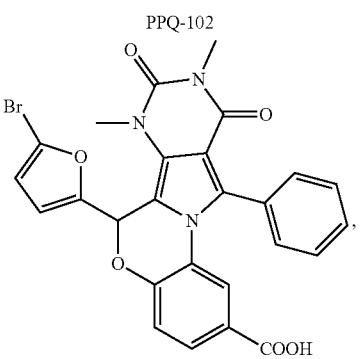

BPO-27 or
a combination thereof.
The agent can also be a compound of formula IV (e.g., a compound of formula IVa or IVb):

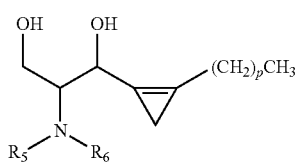

IVa

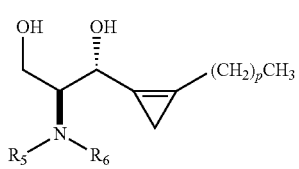

IVb wherein:
$R_5$ is —CO(CH$_2$)$_v$R$_7$, —COO(CH$_2$)$_v$R$_7$, —CONH(CH$_2$)$_v$R$_7$, —CSNH(CH$_2$)$_v$R$_7$, —COCO(CH$_2$)$_v$R$_7$;
v is an integer from 0 to 12;
$R_7$ is methyl or aryl;
$R_6$ is H or lower alkyl; and
p is an integer from 8 to 16.

The GT-11 compound is an example of a compound of formula IV:

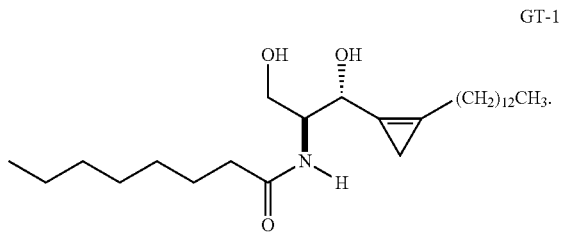

GT-11

Other examples of agents that can be used in the methods and compositions described include:

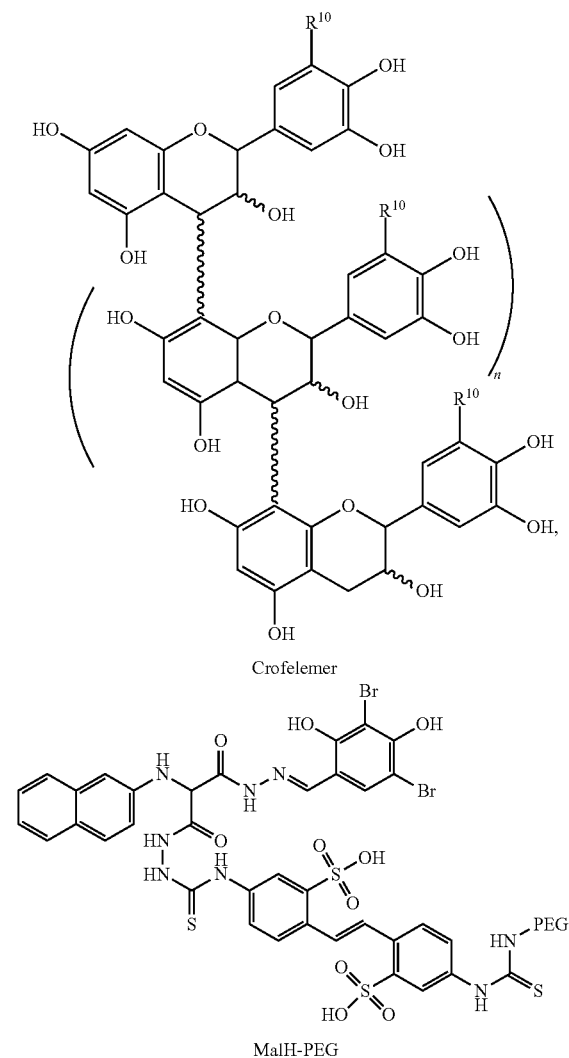

Crofelemer

MalH-PEG or a combination thereof.

Other useful agents for use in the methods and compositions described herein include serine, alanine, glycine or a combination thereof.

Useful compounds include substrates of serine palmitoyl-CoA transferase (SPT) such as serine, alanine and glycine. Useful dihydroceramide reductase inhibitors include fenretinide (4-hydroxyphenylretinamide) and GT-11 (N-[(1R, 2S)-2-hydroxy-1-hydroxymethyl-2-(2-tridecyl-1-cyclopropenyl)ethyl]octanamide) Inhibitors of the cystic fibrosis transmembrane conductance regulator (CFTR) protein including GlyH 101, Crofelemer, PPQ-102, BPO-27, $CFTR_{inh}$-172 and iOWHO32 are also useful. Further examples of CFTR inhibitors that can be used treat asthma include those described in U.S. Pat. Nos. 8,410,132 and 8,058,295, which are specifically incorporated herein by reference in their entireties.

For example, serine, alanine, glycine, Phenyl-GlyH, GlyH 101, fenretinide, GT-11, Crofelemer, PPQ-102, BPO-27, $CFTR_{inh}$-172, Tetrazolo-172, MalH-PEG and iOWHO32 are examples of compounds useful for treating asthma and/or reducing the susceptibility of subjects for asthma and episodes of asthma. Structures of such compounds are shown below:

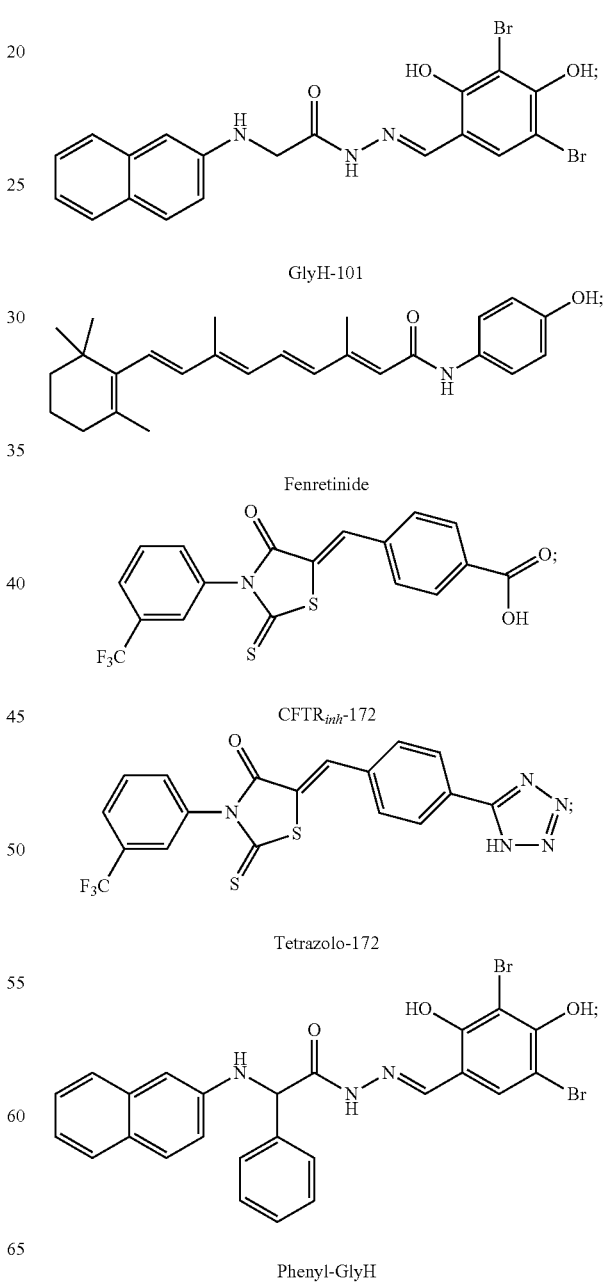

GlyH-101

Fenretinide $CFTR_{inh}$-172

Tetrazolo-172

Phenyl-GlyH

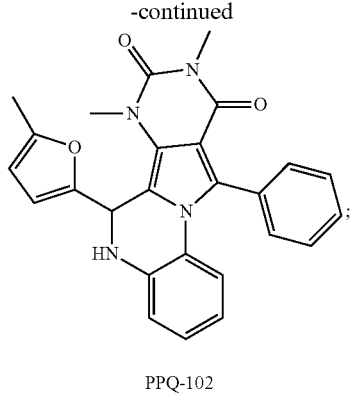

PPQ-102

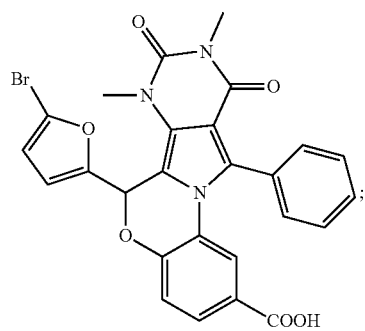

BPO-27

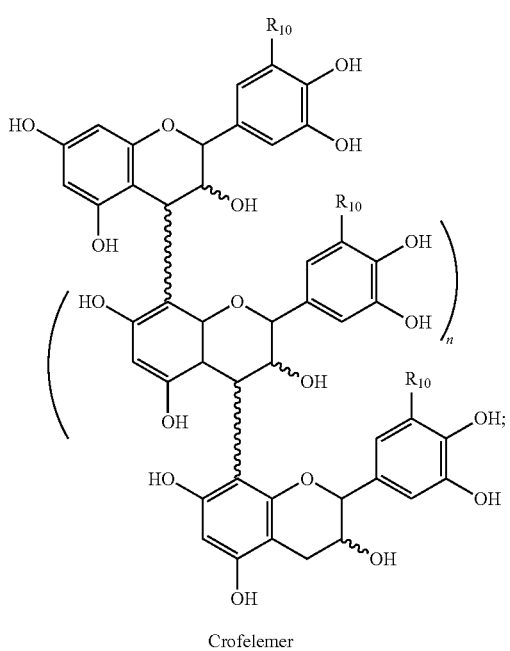

Crofelemer

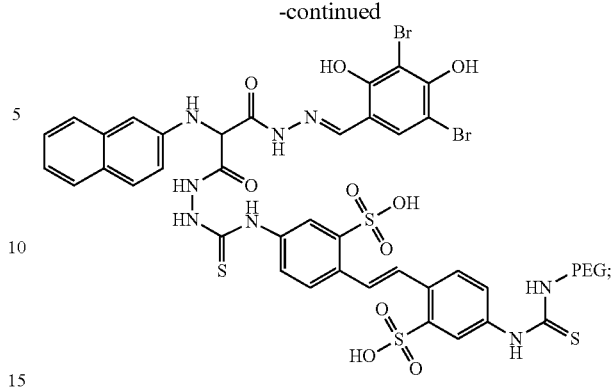

MalH-PEG

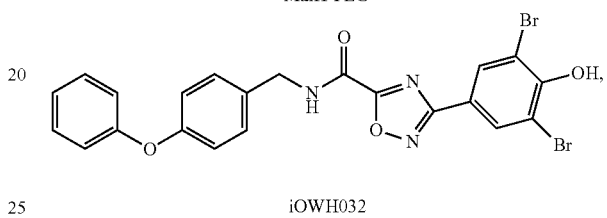

iOWH032 and combinations thereof.

Other CFTR inhibitor such as GlyH-101 (Naphthalen-2-ylamino)-acetic acid (3,5-dibromo-2,4,-dihydroxybenzylidene)-hydrazide) and related compounds described by Muanprasat et al. (*J. Gen. Physiol.* 124, 125-137 (2004)) and Kelly et al. (*J. Pharmacol. Exp. Ther* 333, 60-69 (2010)) can also be employed. CFTR inhibitors that have been developed to create models for cystic fibrosis but also as anti-diarrheal agents in CFTR-dependent secretory diarrheas and agents to treat polycystic kidney disease can also be employed. For example, other compounds can also be employed in the compositions and methods provided herein such as those described by Muanprasat et al. (*J. Gen. Physiol.* 124, 125-137 (2004); Stahl et al. (*Am. J. Physiol.* 302, C67-C76 (2011); de Hostos et al. (Future Med Chem 3(10): 1317-25 (2011); Yang et al. (J Am Soc Nephrol 19 (7): 1300-1310, (2008); Snyder et al. (J Med Chem 54(15): 5468-77 (2011); and Tradtrantip et al. (J Med Chem 52(20): 6447-55 (2009)), each of which is specifically incorporated herein in its entirety.

Any one of these compounds can be used to treat asthma and/or to reduce susceptibility to asthma. A composition useful for treatment of asthma or to reduce asthma susceptibility can also be formulated without any one of the foregoing compounds. The compositions useful for treatment of asthma or to reduce asthma susceptibility can also be formulated without one or more of serine, alanine, glycine, Phenyl-GlyH, GlyH 101, fenretinide, Crofelemer, PPQ-102, BPO-27, $CFTR_{inh}$-172, Tetrazolo-172, MalH-PEG and iOWHO32. Such compositions can also exclude any agent or compound that primarily modulates sphingosine-1P levels.

Two different murine models were used in experiments described herein to test whether impaired activity of SPT in the respiratory tract would induce an asthma phenotype in vivo: (1) Pharmacological inhibition of de-novo sphingolipid synthesis by myriocin, an inhibitor of SPT (Miyake et al., Biochem. Biophys. Res. Commun. 211, 396 (1995)); and (2) SPT-deficient $Sptlc2^{+/-}$ mice (Hojjati et al., Biochim Biophys. Acta 1737, 44 (2005)). Myriocin acts through phosphorylation of Orm proteins (Breslow et al., Nature 463, 1048 (2010); Roelants et al., Proc. Natl. Acad. Sci. 108, 19222 (Nov. 29, 2011)). Myriocin administration to animals provides an asthma model useful for testing and evaluating compounds for efficacy against asthma.

Figure 1E:
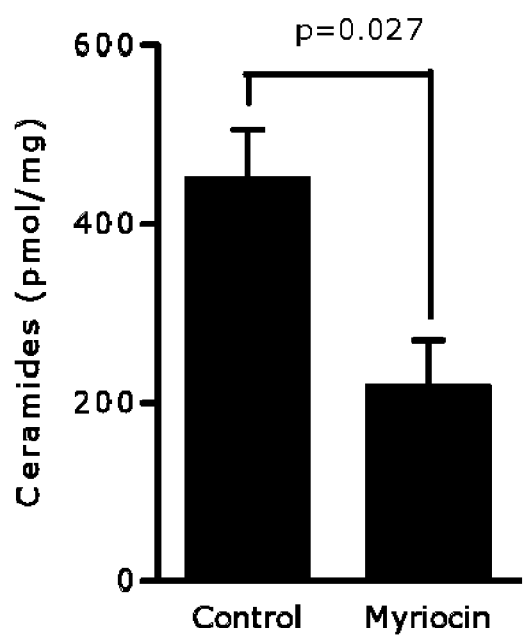

As shown herein, measurements made 3 hours following intranasal administration of myriocin demonstrate that SPT-dependent synthesis of sphinganine from $^3$H-serine was significantly decreased (FIG. 1). Although sphingosine, sphinganine-1P and sphingosine-1P were lower after myriocin administration, the reduction was not statistically significant (FIG. 1). However, as shown in FIG. 1E, the sum of ceramides (C14, C16, C18, C20, C22, C24, C24:1) was decreased by myriocin (FIG. 1E). Non-SPT-dependent syntheses of ceramides or sphingomyelins from $^3$H-sphingosine were not affected by myriocin administration (data not shown). Thus, administration of a dose of myriocin to the respiratory tract impairs de-novo sphinganine synthesis in the lung.

The lung function phenotype of genetic SPT-deficient Sptlc2$^{+/-}$ mice was also assessed by experiments described herein. Sptlc2 codes for one of the three subunits of SPT (Hornemann et al., Biochem. J. 405, 157 (2007)). Homozygous knockout of the gene is embryologically lethal, and heterozygous Sptlc2$^{+/-}$ have 60% decreased hepatic SPT activity, decreased serum ceramide and sphingosine levels but no other apparent phenotype (Hojjati et al., Biochim Biophys. Acta 1737, 44 (2005)).

Figure 2A:
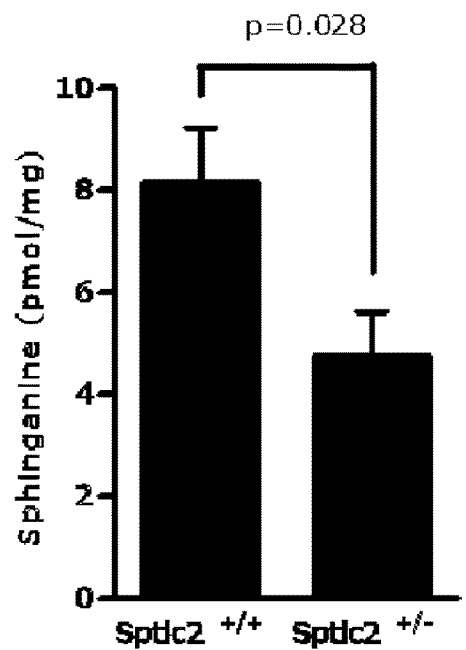
FIG. 2A-2I graphically illustrates that lung sphingolipids are reduced in mice with decreased SPT activity. Long chain bases and ceramides of lung homogenates from Sptlc2$^{+/-}$ and Sptlc2$^{+/+}$ mice were quantified by tandem mass spectrometry (LC-MS/MS).
Figure 2B:
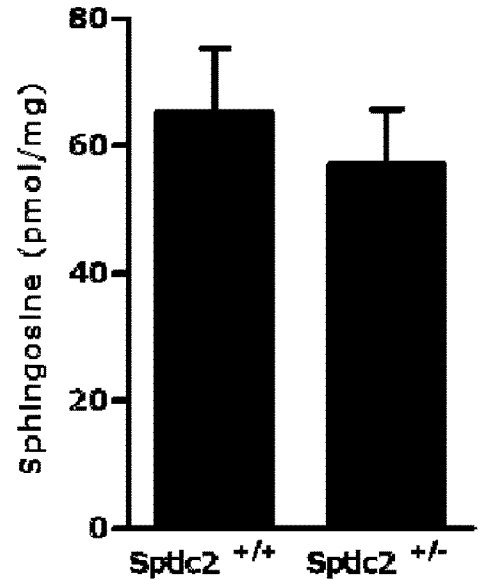
Figure 2C:
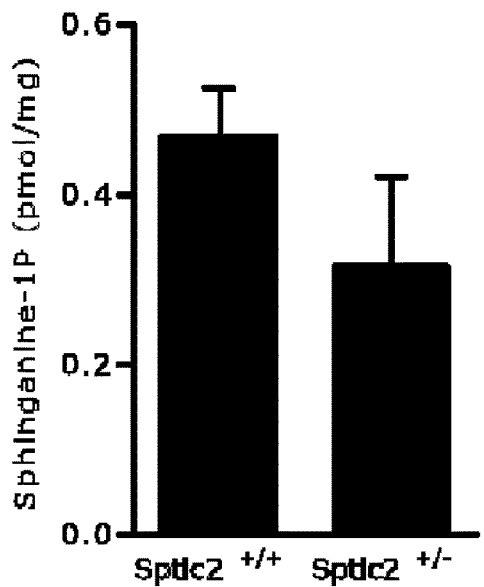
Figure 2D:
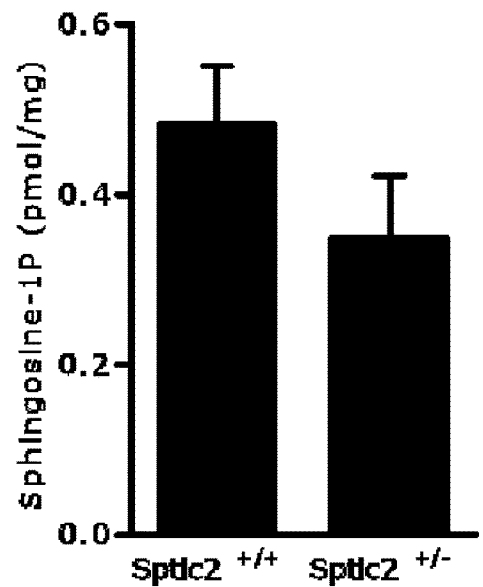
Figure 2E:
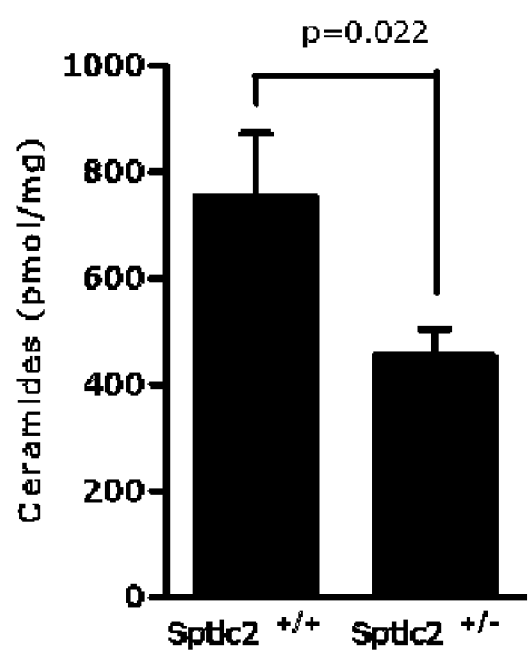

As shown herein, sphinganine and ceramides were decreased in lungs of Sptlc2$^{+/-}$ mice (FIGS. 2A and 2E). Thus, lung sphingolipid composition is altered in Sptlc2$^{+/-}$ mice, which is consistent with decreased SPT activity.

Figure 3A:
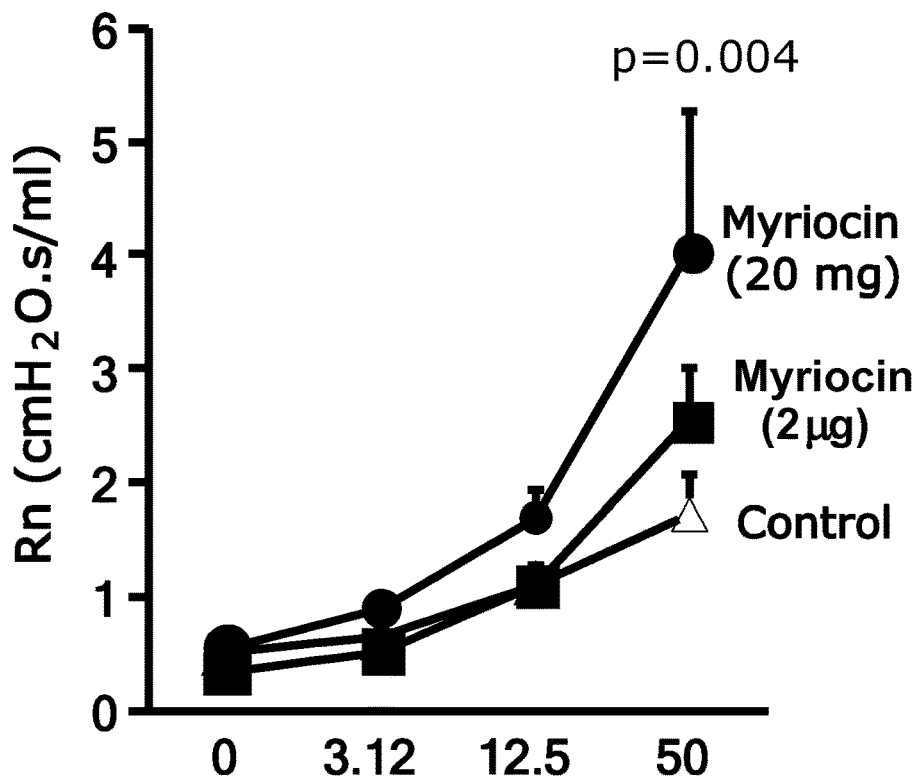
FIG. 3A-3H show that decreased SPT activity leads to bronchial hyper-responsiveness.
Figure 3B:
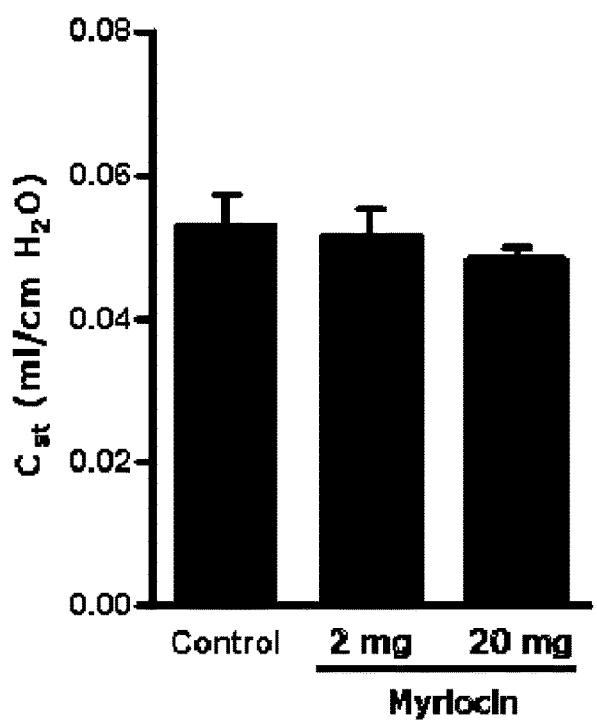
Figure 3C:
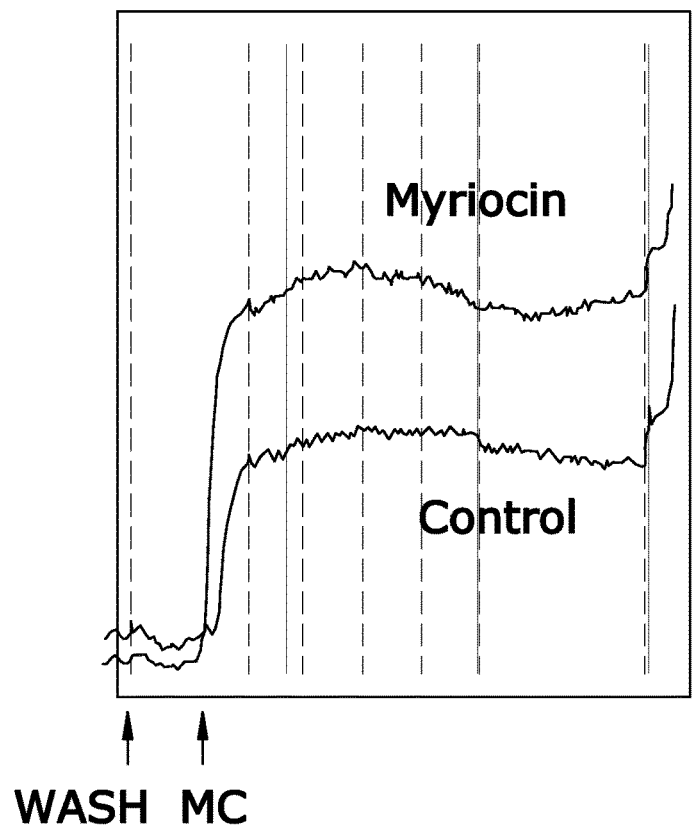
Figure 3D:
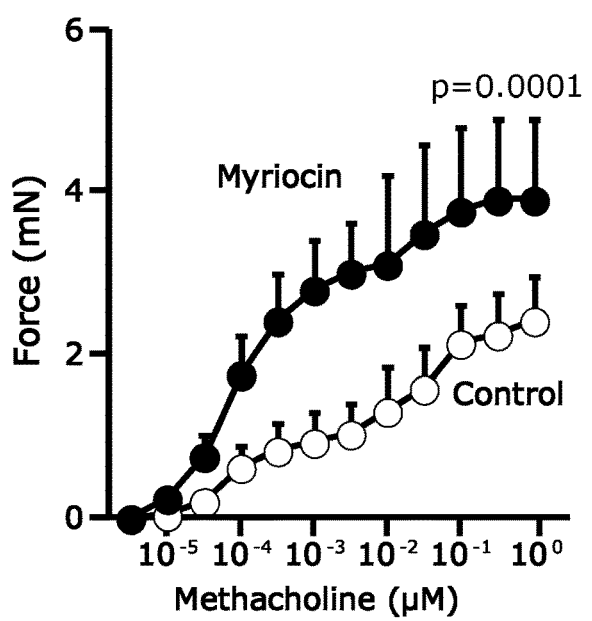
Figure 3E:
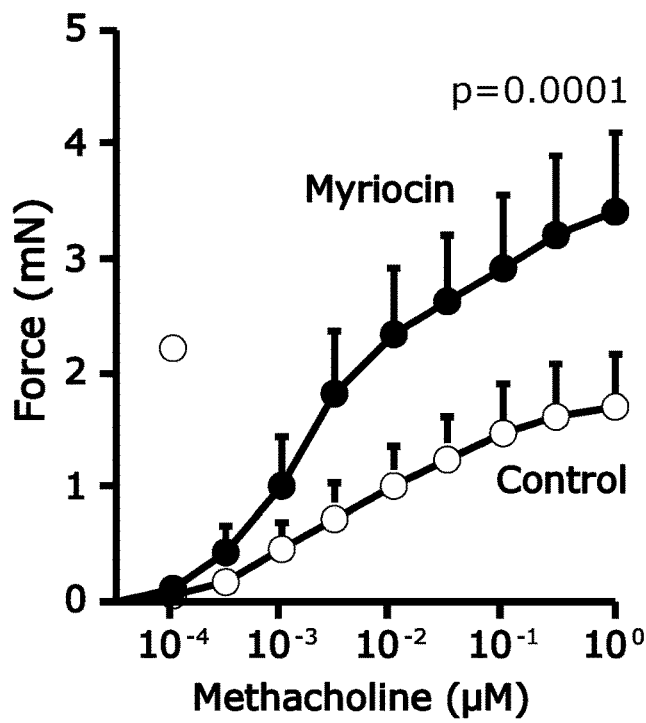

Methacholine was used to induce bronchoconstriction in Sptlc2$^{+/-}$ and Sptlc2$^{+/+}$ mice, as well as in mice pre-treated with myriocin. Airway reactivity, determined by changes in central airway resistance (Rn) in response to nebulized methacholine, was increased 3 h following myriocin administration (FIG. 3A). Application of myriocin directly to the respiratory tract increased contractile responses of bronchial rings isolated from these mice (FIG. 3C) in a dose-dependent manner (FIG. 3D). Human bronchial rings that were kept for 90 min in a myriocin-containing bath solution also exhibited increased contractile force (FIG. 3E).

Figure 3F:
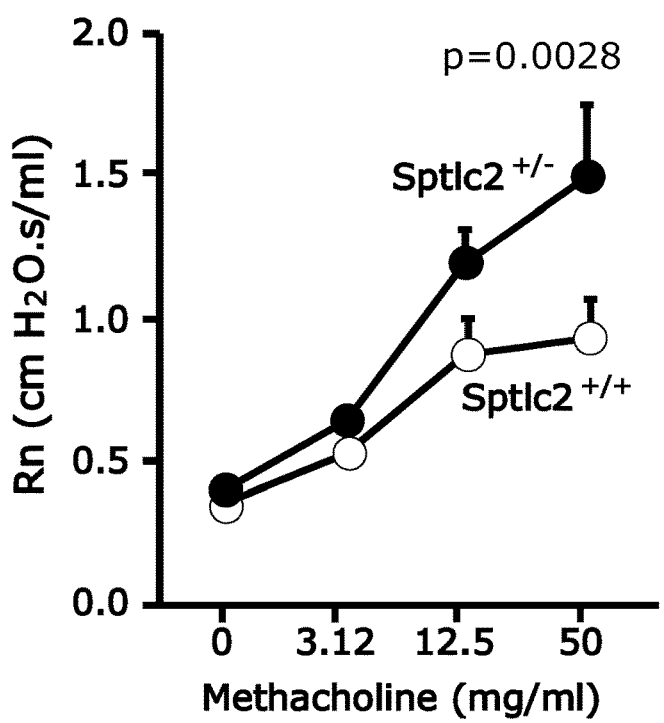
Figure 3G:
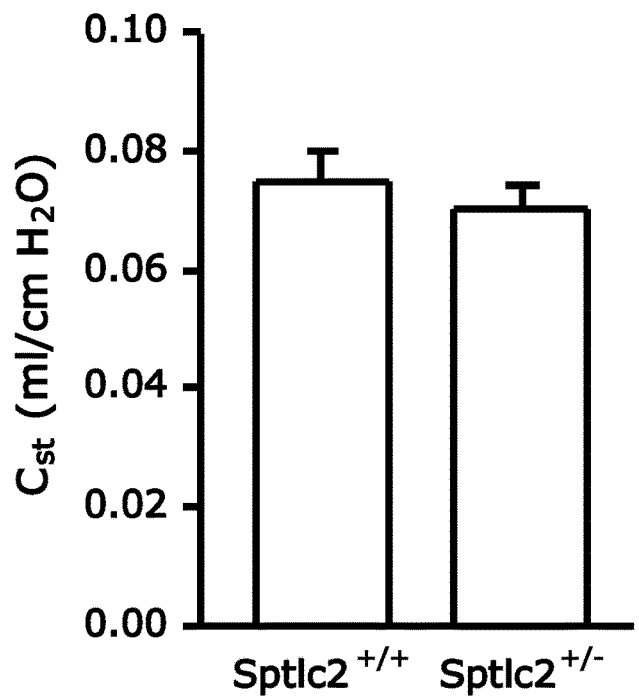
Figure 3H:
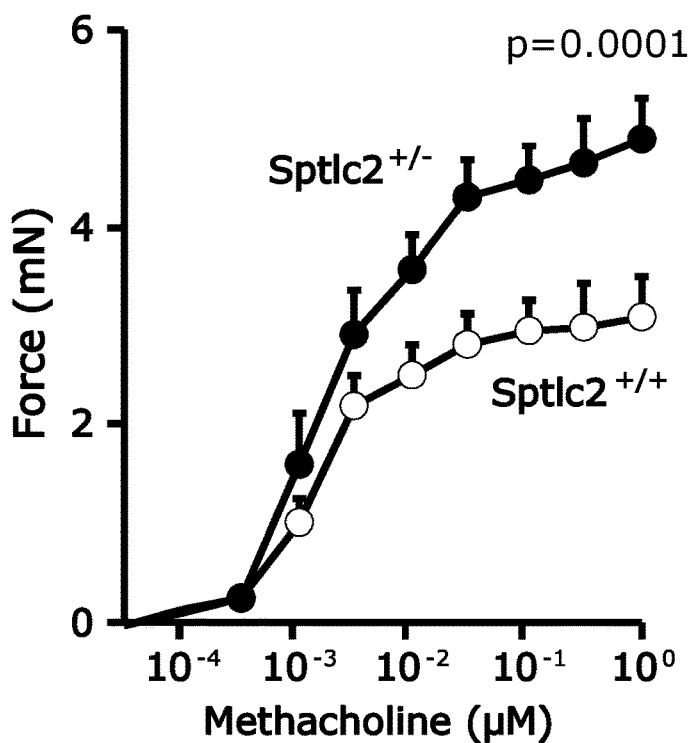

Airway resistance was also increased in response to methacholine in Sptlc2$^{+/-}$ mice compared to Sptlc2$^{+/+}$ controls (FIG. 3F). No differences were detected in the baseline mechanical lung parameters, including static compliance (FIG. 3G). Also, isolated bronchial rings from Sptlc2$^{+/-}$ mice had an increased contractile response to methacholine compared to bronchial rings isolated from controls (FIG. 3H). Thus, acute or chronic partial SPT deficiency in the respiratory tract affects lung sphingolipid composition and increases airway reactivity.

Figure 4A:
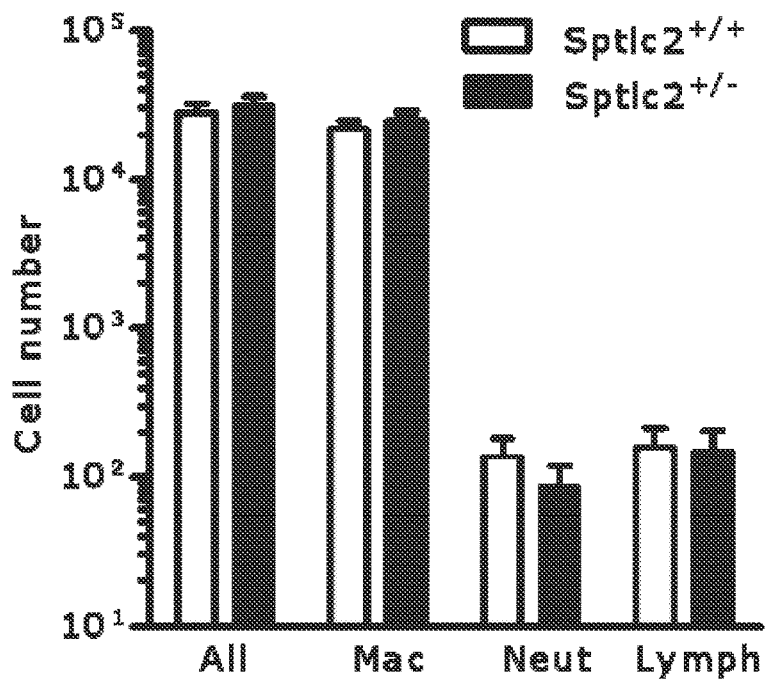
Figure 4B:
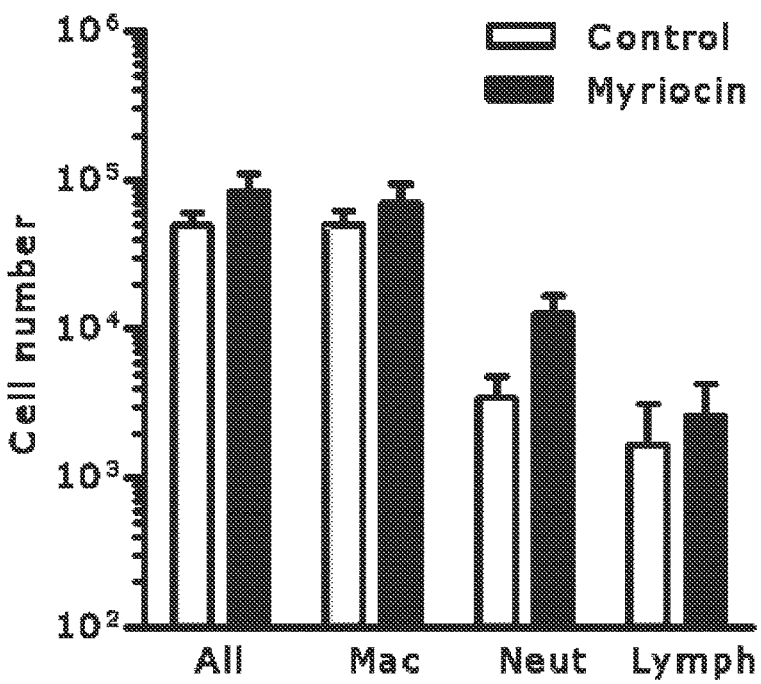
FIG. 4B graphically illustrates the numbers of cells in bronchioalveolar lavage from myriocin-treated (20 μg) mice.
Figure 4G:
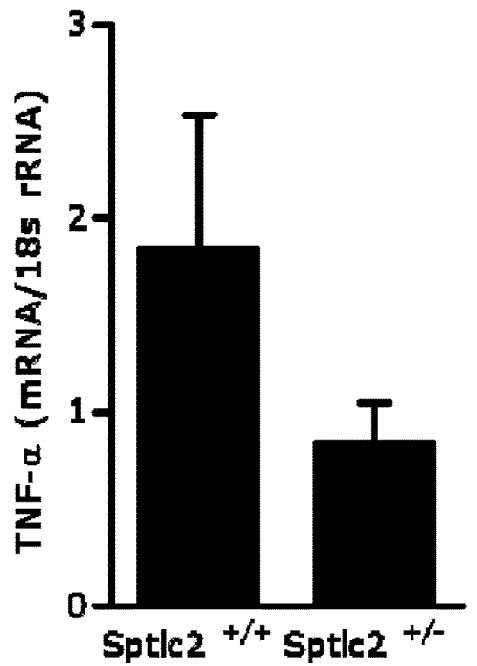
FIG. 4G graphically illustrates the expression level of tumor necrosis factor alpha (TNF-α) in Sptlc2$^{+/-}$ mice.
Figure 4H:
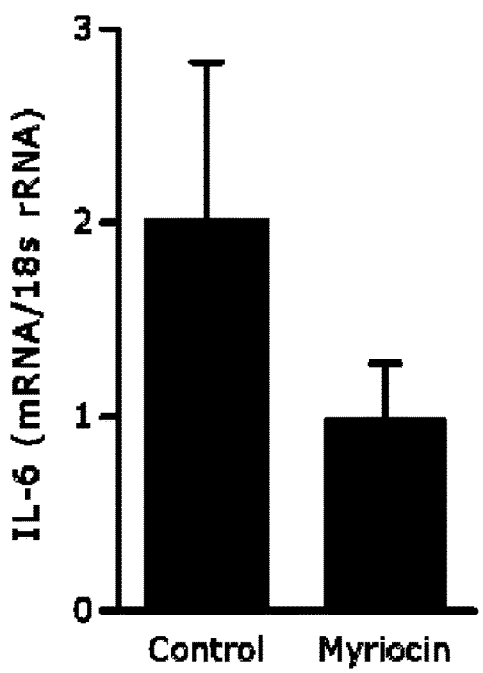
FIG. 4H graphically illustrates the expression level of interleukin-6 (IL-6) following myriocin (20 μg) administration.
Figure 4I:
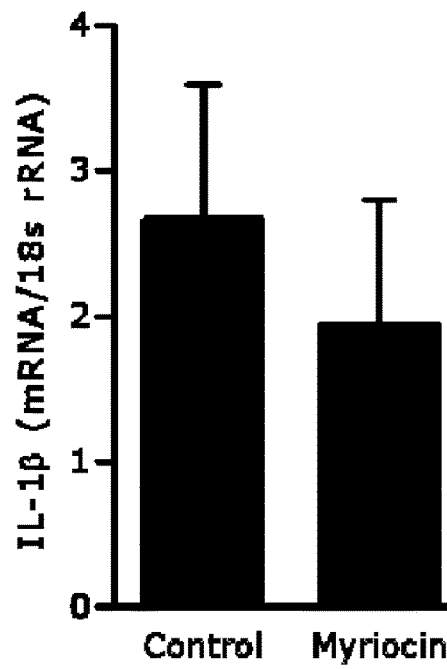
FIG. 4I graphically illustrates the expression level of interleukin-1β (IL-1β) following myriocin (20 μg) administration.
Figure 4J:
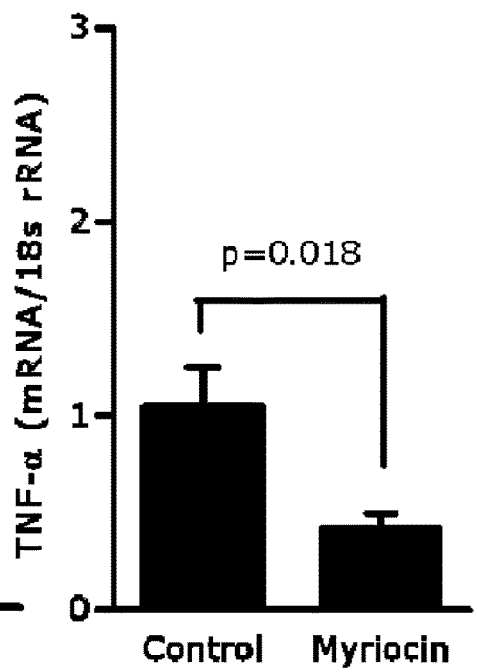
FIG. 4J graphically illustrates the expression level of tumor necrosis factor alpha (TNF-α) following myriocin (20 μg) administration. Expression levels shown in FIG. 4E-4J were quantified by RT-Real-Time PCR and normalized to 18S RNA. Data in FIG. 4A-4B are the mean of 5-8 mice/group. The images shown in FIG. 4C-4D are representative of three independent experiments. The expression levels in FIG. 4H-4J are the mean of 5-8 mice/group. The error bars show s.e.m. The symbol * signifies $p<0.05$ (FIG. 4A-4B: ANOVA.

Further studies were undertaken to determine if inflammation is associated with decreased SPT activity in the respiratory tract. Numbers of different types of immune cells in bronchial alveolar lavage (BAL) from Sptlc2$^{+/-}$ mice were similar to those in the BAL of Sptlc2$^{+/+}$ controls (FIG. 4A). A small increase in the number of neutrophils was seen in the BAL of myriocin-treated animals (FIG. 4B). However, no inflammatory changes were seen in lung sections of Sptlc2+/− mice (FIG. 4C) or myriocin-treated mice (FIG. 4D). Expression of the inflammatory cytokines IL-6, IL-1β or TNF-α in the lungs of Sptlc2$^{+/-}$ or myriocin-treated mice was not increased compared to their respective controls. Instead, Il-6 (FIG. 4E) was decreased in Sptlc2$^{+/-}$ mice and TNF-α was decreased in the myriocin-treated mice (FIG. 4J). Thus, decreased SPT activity in the lung is not associated with increased inflammation.

Prior studies linking asthma to sphingolipids have centered on inflammatory and allergic mechanisms related to the sphingolipid mediator sphingosine-1P (S1P). Sphingosine-1P is involved in mast cell degranulation and airway hyper-responsiveness in allergic asthma models (Kume et al., J. Pharmacol. Exp. Ther. 320, 766 (2007); Roviezzo et al., Am. J. Respir. Cell. Mol. Biol. 42, 572 (2010); Roviezzo et al., Am. J. Respir. Cell. Mol. Biol. 36, 757 (2007); Ryan et al., Drug News Perspec. 21, 89 (2008)). Sphingosine-1P has been a focus for development of sphingolipid-based anti-inflammatory agents (Ble et al., Br. J. Pharmacol 158, 1295 (2009); Lai et al., J Immunol. 180, 4323 (2008); Lai et al., Biosci. Rep. 31, 145 (2011); Nishiuma et al., 27-30). However, sphingosine-1P levels in the lung were not altered in the models reported here.

Figure 4L:
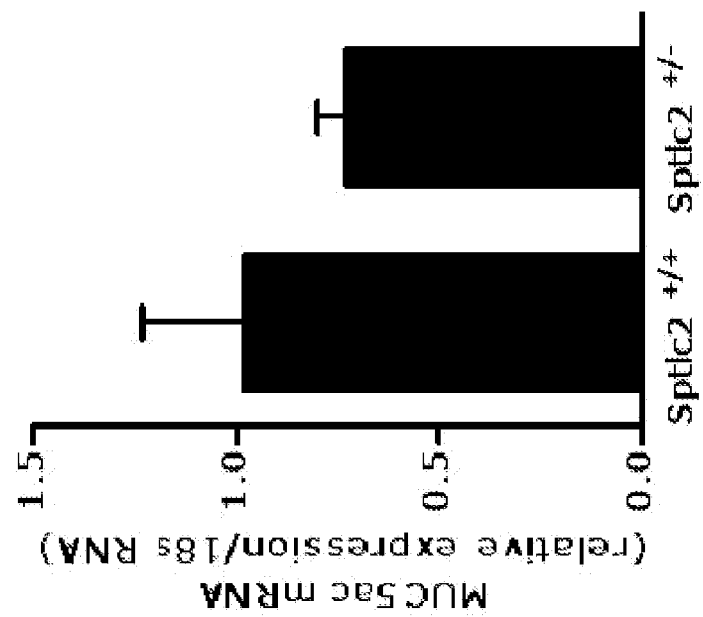
Figure 4K:
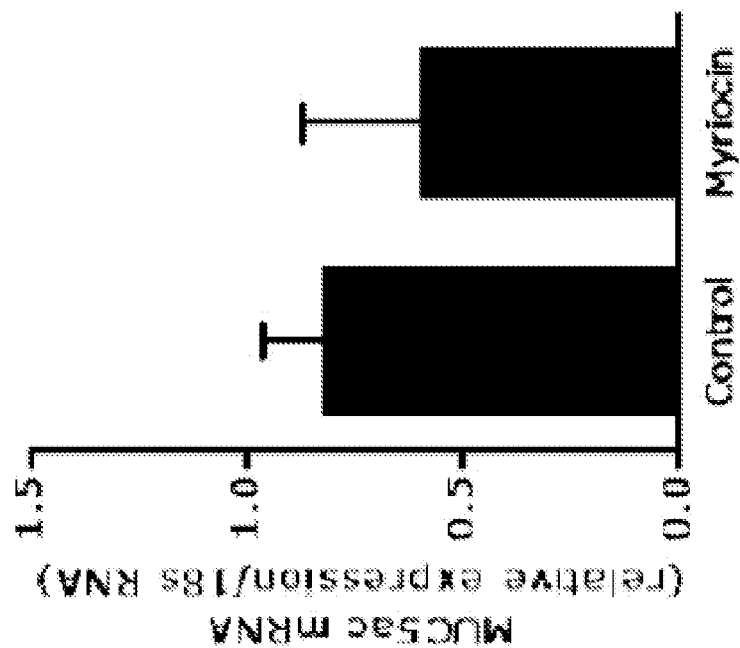

Increased mucus production and airway remodeling are other major features associated with asthma besides inflammation and airway hyper-responsiveness. No differences in mucus-producing cells were seen on Periodic acid-Schiff (PAS)-stained lung sections of myriocin-treated mice and Sptlc2$^{+/-}$ mice. Expression of Muc5ac, a marker to assess mucus production in mice (Oguma et al., J. Immunol. 187, 999 (2011)), was unchanged in both, myriocin-treated mice and in Sptlc2$^{+/-}$ mice (FIG. 4K-4L).

Figures 4M, 4N:
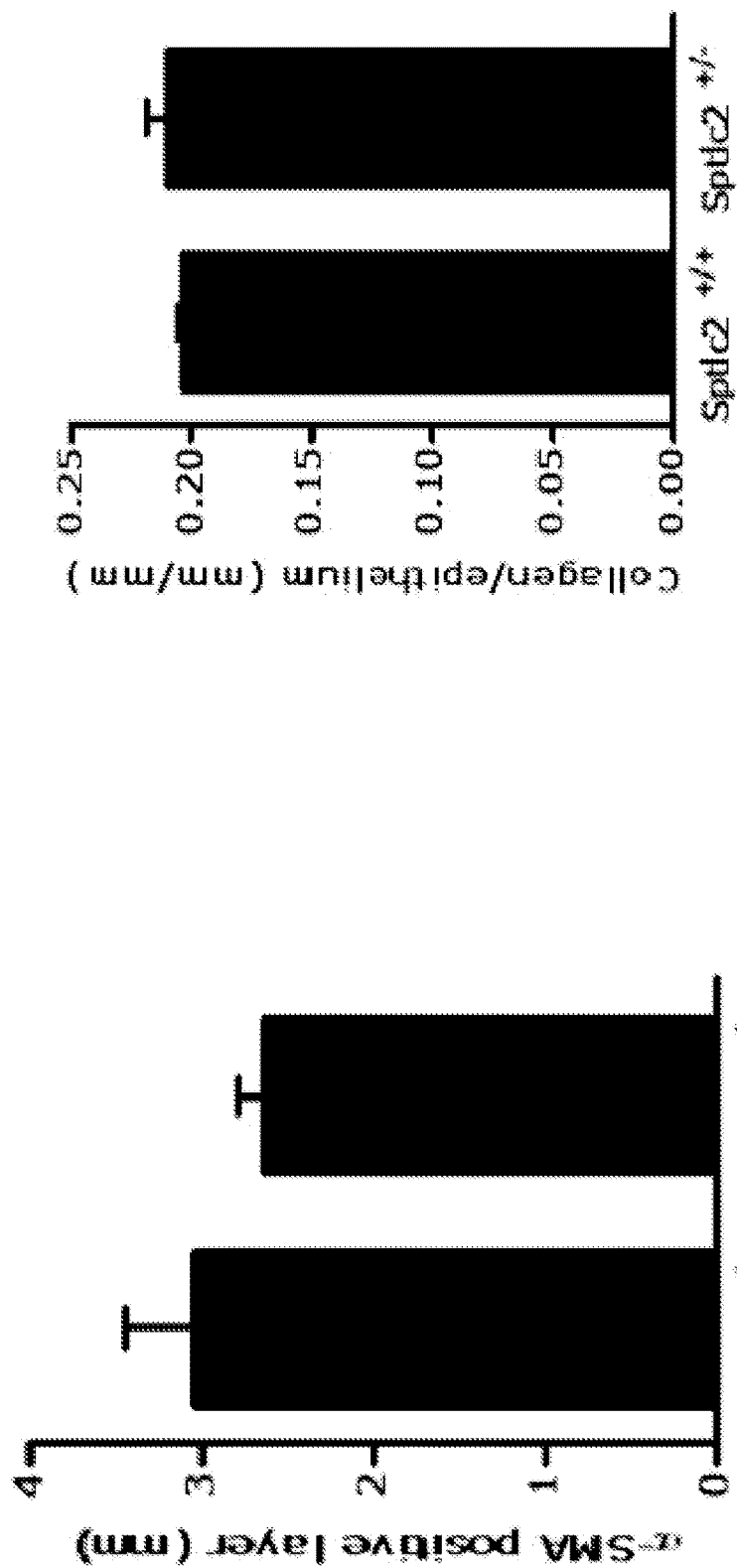

It has been suggested that ORMDL3 is related to epithelial cell remodeling based on the finding that heterologous expression of human ORMDL3 increased cytosolic Ca$^{2+}$ and facilitated the unfolded protein response through decreased expression of SERCA (Cantero-Recasens et al., Hum. Mol. Genet. 19, 111 (2010)), a protein related to airway remodeling (Mahn et al., Proc. Natl. Acad. Sci. 106, 10775 (2009)). However, no changes were observed in the lungs of the Sptlc2$^{+/-}$ mice that suggested airway remodeling. Bronchial wall thickness and the thickness of the bronchial collagen layer in 100-200 μm bronchi was comparable between Sptlc2$^{+/-}$ and Sptlc2$^{+/+}$ mice (FIG. 4M-4N). Furthermore, bronchial hyper-responsiveness occurred just hours after SPT inhibition with myriocin, which makes it unlikely that structural changes caused such bronchial hyper-responsiveness.

Figure 5A:
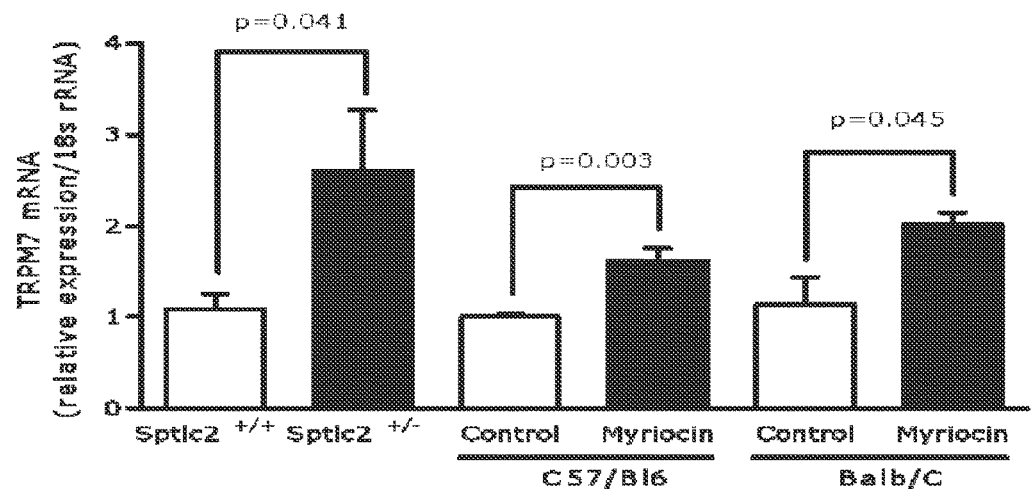
FIG. 5A-5D illustrates that magnesium homeostasis is altered in lungs with decreased SPT activity.
Figure 5B:
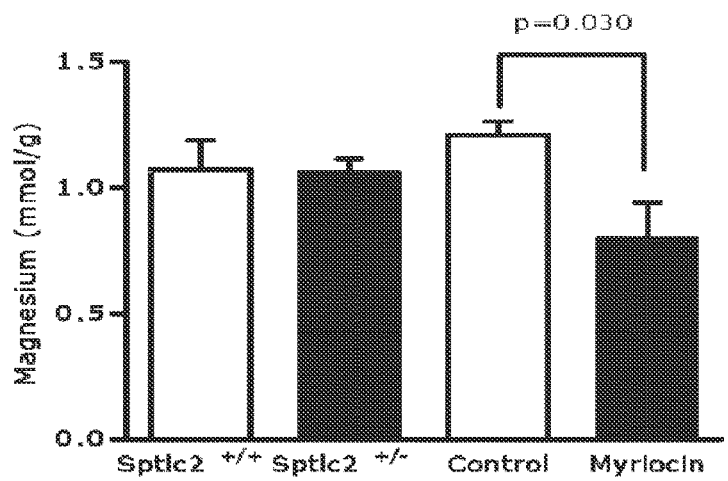
Figure 5C:
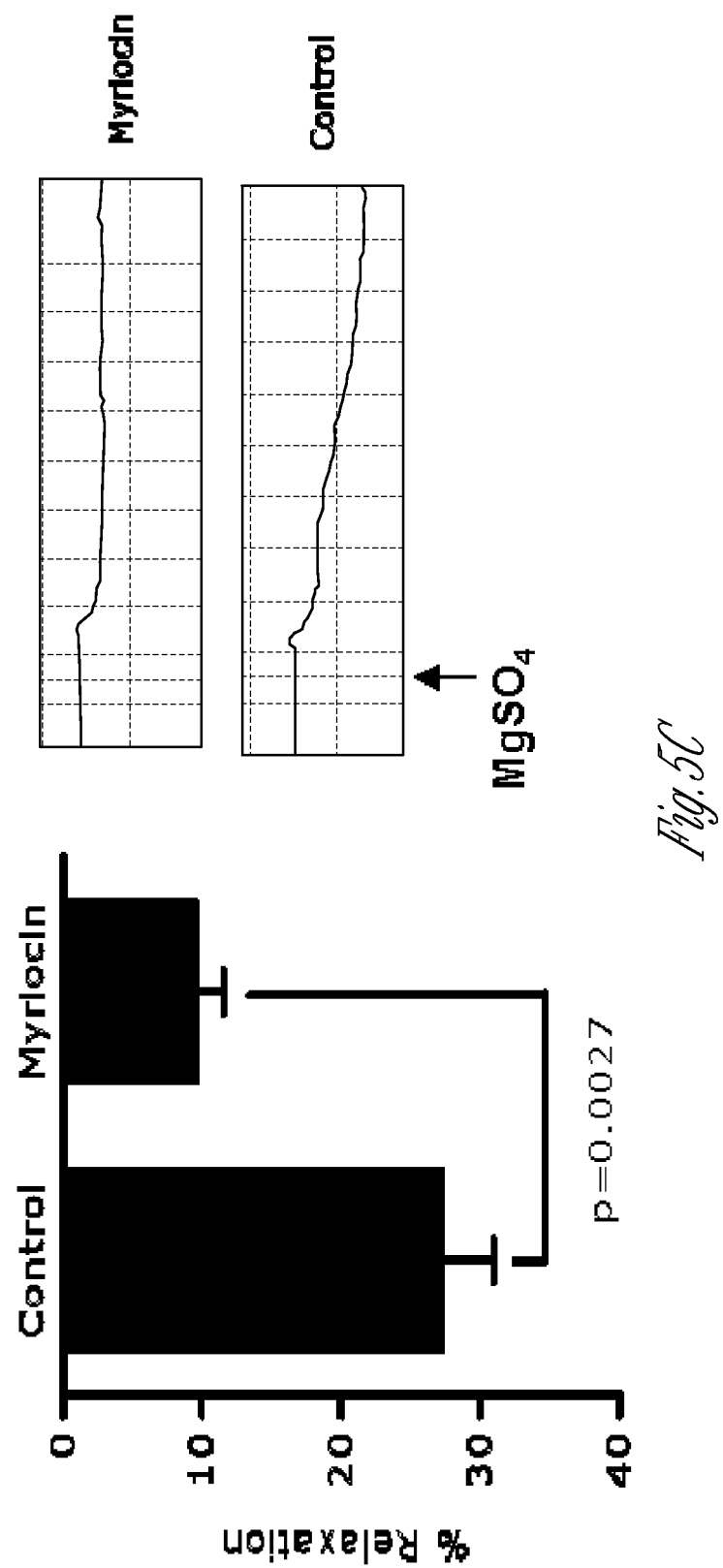
Figure 5D:
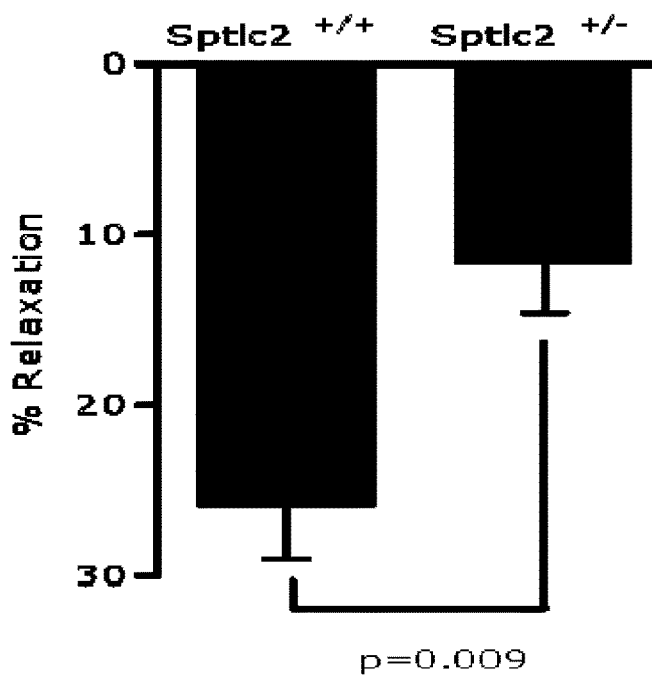

A recent report suggests that supplementation of cultured vascular smooth muscle cells with short-chain ceramides and sphingomyelins increases intracellular magnesium (Mg$^{2+}$) concentration (Zheng et al., Am. J. Physiol. 300, H486 (2011)). TRPM7 is a universally expressed regulator of cellular Mg$^{2+}$ homeostasis (Ryazanova et al., Nat. Commun 1, 109 (2010); Schmitz et al., Cell 114, 191 (2003); Touyz, Am. J. Physiol. 294, H1103 (2008)). As shown in FIG. 5A, TRPM7 expression was increased in the lungs of Sptlc2$^{+/-}$ mice and in mice that had received myriocin. Total serum (not shown) and lung magnesium levels were unaffected in Sptlc2$^{+/-}$ mice (FIG. 3B). However, lung magnesium levels in myriocin-treated mice were reduced (FIG. 3B). The expression of TRPM6, the "gatekeeper" in transepithelial magnesium transport (Groenestege et al., J. Am. Soc. Nephrol. 17, 1035-1043 (2006)), was not altered When bronchial rings isolated from mice that had received intranasal myriocin were stimulated with methacholine prior to addition of MgSO$_4$, the magnesium-induced relaxation of the rings was impaired (FIG. 5C). A similar pattern was seen in bronchial rings isolated from Sptlc2$^{+/-}$ mice (FIG. 5D). Thus, decreased SPT activity in the respiratory tract alters magnesium homeostasis and the response of the airways to magnesium.

Asthma has been associated with lower intracellular magnesium concentrations (Dominguez et al., Clin. Sci. 95, 137 (1998); Hashimoto et al., J. Asthma 37, 489 (2000); Jiang et al., Eur. Rev. Med. Pharmacol. Sci. 14, 935 (2010); Sinert et al., Scand. J. Clin. Lab. Invest. 65, 659 (2005)). Systemic or aerosolized $MgSO_4$ is used to treat asthma exacerbations (Dominguez et al., Clin. Sci. 95, 137 (1998); Hughes et al., Lancet 361, 2114 (2003); Kowal et al., Arch. Immunol. Ther. Exp. 55, 35 (2007); Lindeman et al., J. Appl. Physiol. 66, 2527 (1989); Rolla et al., Magnesium 6, 201 (1987); Villeneuve et al., Ann Pharmacother. 40, 1118 (2006)). However, the universal efficacy of magnesium supplementation is controversial.

Total magnesium concentrations in the lung were mildly decreased upon administration of myriocin, but were unchanged in serum, erythrocytes, lung and BAL of the $Sptlc2^{+/-}$ mice. $Sptlc2^{+/-}$ mice are a longer term asthma-prone animal model than myriocin-administered animals. Hence, the increased levels of magnesium in the lungs of $Sptlc2^{+/-}$ mice compared to myriocin-administered mice may be due to compensation in the $Sptlc2^{+/-}$ mice, which have had time to adapt. As noted, the expression of TRPM6, which is the "gatekeeper" in transepithelial $Mg^{2+}$ transport, was not altered in $Sptlc2^{+/-}$ mice or in myriocin-administered mice, but expression of TRPM6 and TRPM7 can be affected by a variety of factors (Touyz, Am. J. Physiol. 294, H1103 (2008); Groenestege et al., J. Am. Soc. Nephrol. 17, 1035 (2006)).

While both asthma models ($Sptlc2^{+/-}$ mice and myriocin-administered mice) exhibited impaired magnesium-induced relaxation upon methacholine-induced bronchoconstriction, administration of agents that directly increase the products of the de-novo sphingolipid synthetic pathway is an improvement over administration of magnesium to treat asthma, because there does not appear to be any role for magnesium supplementation in chronic stable asthma (Bernstein et al., Arch Intern Med. 1995; 155:271-276; 4. National Institutes of Health. Global strategy for asthma management and prevention. Bethesda, Md.: National Institutes of Health, National Heart, Lung, and Blood Institute; 2002). None-the-less, observation of an impaired magnesium-induced relaxation response in a subject is an indicator that the subject can benefit from use of the methods and compositions described herein.

Figure 6A:
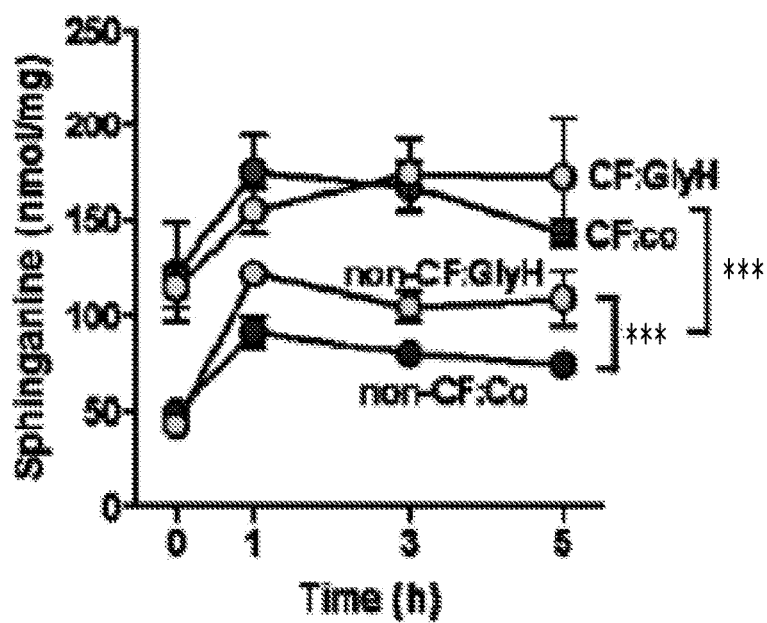
FIG. 6A-6D illustrates that GlyH-101 increases sphingolipid synthesis in respiratory epithelial cells and alleviates bronchial hyper-reactivity in SPT-deficient mice.
Figure 6B:
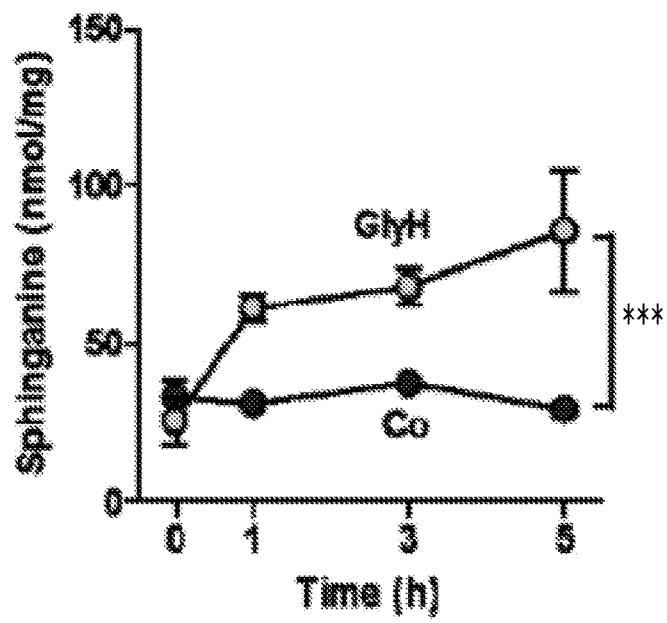

As demonstrated herein, administering an agent that is capable of increasing de-novo sphingolipid synthesis is beneficial for treatment of bronchial hyper-responsiveness. For example, as shown in FIG. 6 sphinganine (produced by the de-novo sphingolipid synthesis pathway), increases when GlyH-101 is added to non-CF airway epithelial cells. CF airway epithelial cells have increased baseline levels of sphinganine that are not altered with the CFTR inhibitor (FIG. 6A). GlyH-101 also increases sphinganine in A549 cells, a lung epithelial cell line (FIG. 6B).

Figure 6C:
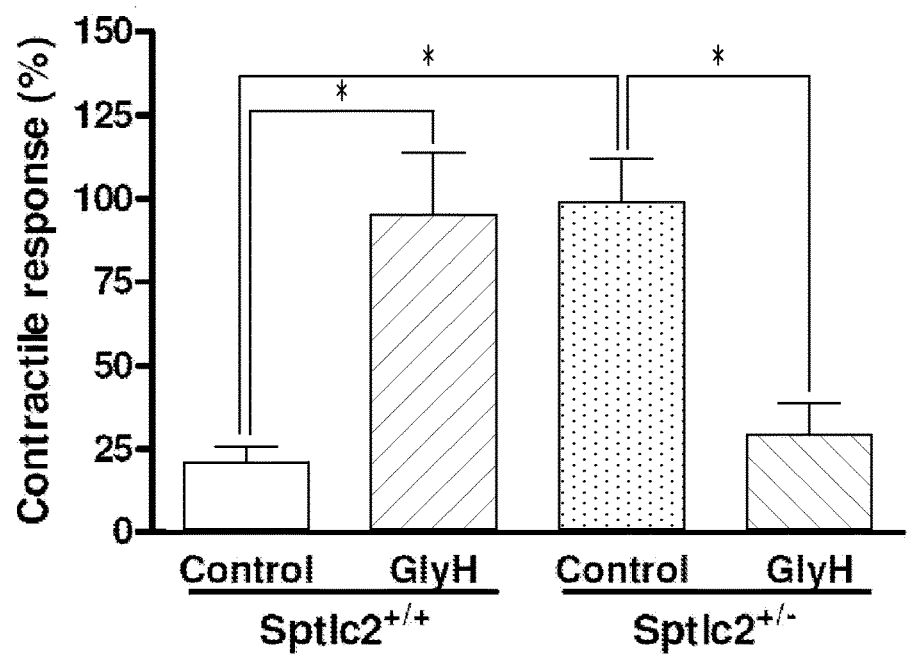
Figure 6E:
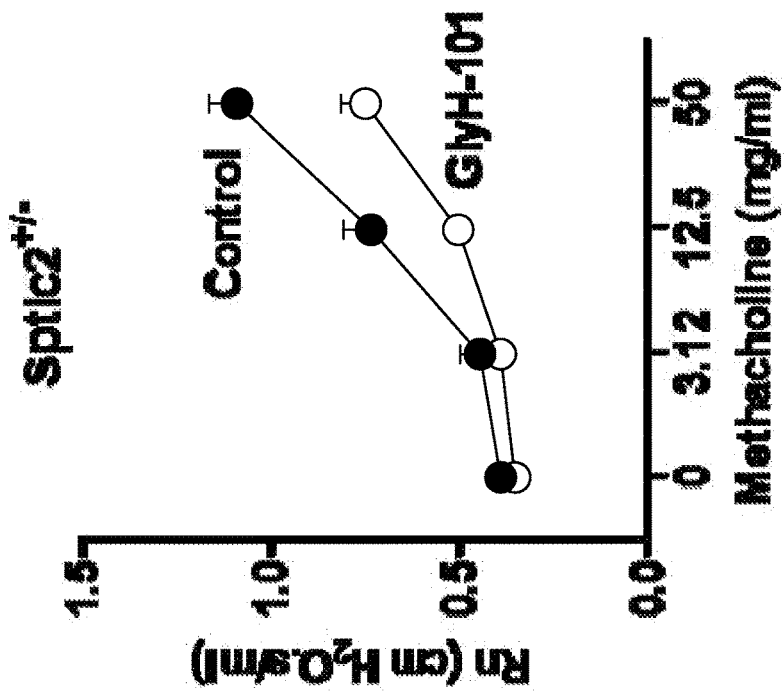
FIG. 6E shows that GlyH-101 alleviates airway resistance observed in Sptlc2$^{+/-}$ mice after intranasal administration of methacholine. GlyH-101 (5 μg) was instilled intranasally to Sptlc2$^{+/+}$ (FIG. 6D) and Sptlc2$^{+/-}$ (FIG. 6E) mice. Airway resistance (Rn) in response to increasing doses of inhaled methacholine was determined after 3 h. As shown, only the increased airway reactivity in the SPT-deficient Sptlc2$^{+/-}$ mice responds to treatment with GlyH-101.
Figure 6D:
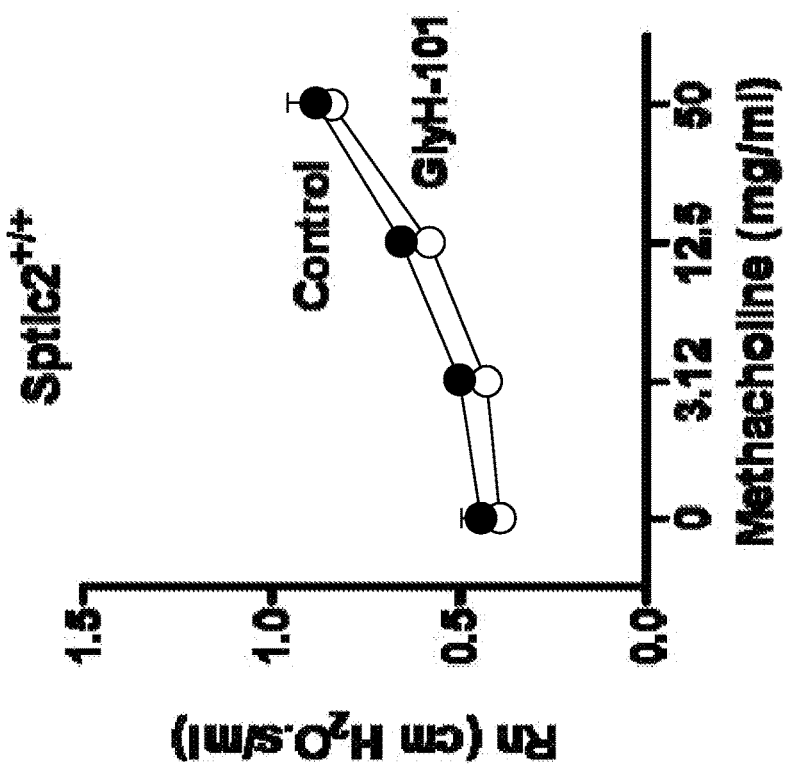

Further, as shown in FIG. 6C, inhibition of CFTR by GlyH-101 in bronchial rings from wild type mice ($Sptlc^{+/+}$) leads to an increased contractile response. In contrast, bronchial rings from Spt-deficient mice exhibit a contractile response upon methacholine administration that is decreased by GlyH-101. Similarly, in FIG. 6D, airway resistance (Rn) of wild type mice upon methacholine administration is unaffected by GlyH-101 but this is not the case when Spt-deficient mice are tested. FIG. 6E shows that the airway resistance observed in Spt-deficient ($Sptlc^{+/-}$) mice upon methacholine administration is relieved by GlyH-101. Thus, inhibition of CFTR by GlyH-101 ameliorates bronchial hyper-responsiveness induced by Spt deficiency. Inhibition of CFTR therefore increases sphingolipid de-novo synthesis in Spt-deficient cells (FIG. 6A-6B), and lead to normalization of bronchial hyper-reactivity (FIG. 6C-6E).

Figure 7:
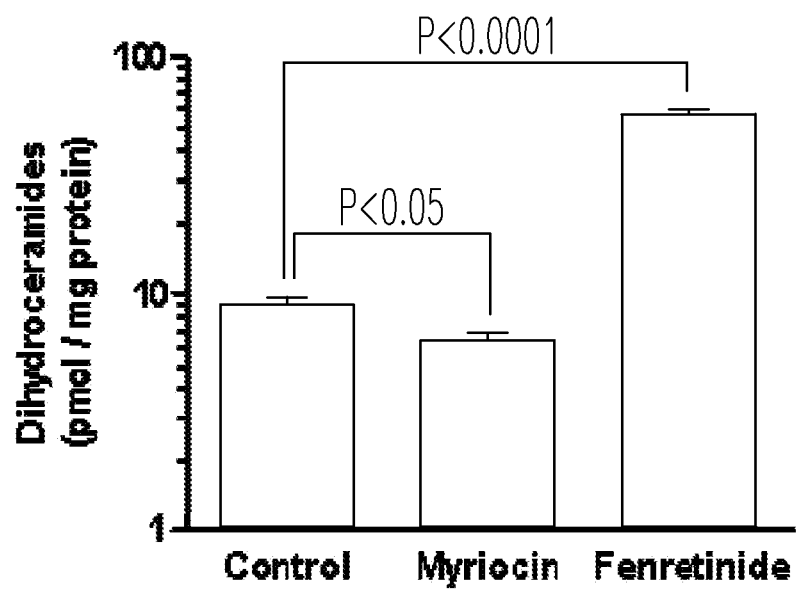
FIG. 7 illustrates that fenretinide increases metabolites of de-novo sphingolipid synthesis. Human bronchial epithelial cells were incubated with myriocin (1 μM) or fenretinide (10 μM) for 3 h in serum free medium supplemented with fatty acid-free bovine serum albumin (0.1%). Cell lysates were analyzed by mass spectrometry. The sums (mean+SEM) of all dihydroceramides are shown as a reflection of the activity of the de-novo sphingolipid synthesis pathway.

Another therapeutic agent that can reduce asthmatic bronchoconstriction is Fenretinide (4-hydroxy(phenyl)retinamide; 4-HPR). Fenretinide is an inhibitor of dihydroceramide reductase. This enzyme catalyzes the formation of ceramides and thereby siphons off sphingolipids from the de-novo synthetic pathway. Inhibition of dihydroceramide reductase increases the concentration of sphingolipids generated through the de-novo sphingolipid synthesis pathways as shown in FIG. 7.

Thus, GlyH-101, fenretinide and related compounds, such as those described herein, can be used to enhance sphingolipid synthesis and reduce the susceptibility to bronchoconstriction of a subject. Other CFTR inhibitors that can be employed in the methods and compositions described herein include iOWHO32 [3-(3,5-dibromo-4-hydroxyphenyl)-N-(4-phenoxybenzyl)-1,2,4-oxadizole-5-carboxamide] (52), crofelemer (a proanthrocyanidin oligomer), PPQ-102 {7,9-dimethyl-11-phenyl-6-(5-methylfuran-2-yl)-5,6-dihydro-pyrimido[4',5'-3,4]pyrrolo[1,2-a]quinoxaline-8,10-(7H,9H)-dione} (Tradtrantip et al., J Med Chem 52(20): 6447-55 (2009)). BPO-27 {6-(5-bromofuran-2-yl)-7,9-dimethyl-8,10-dioxo-11-phenyl-7,8,9,10-tetrahydro-6H-benzo[b]pyrimido[4',5':3,4]pyrrolo[1,2-d][1,4]oxazine-2-carboxylic acid 42} (Synder et al., J Med Chem 54(15): 5468-77 (2011)) and CFTRinh-172 ([3-[(3-trifluoromethyl)phenyl]-5-[(4-carboxyphenyl)methylene]-2-thioxo-4-thiazolidinone]) (Yang et al., J Am Soc Nephrol 19 (7): 1300-1310, (2008)).

Dihydroceramide reductase inhibitors, amino acid substrates of SPT (such as serine, alanine and glycine), as well as inhibitors of CFTR including any of those shown above enhance de-novo sphingolipid synthesis. For example, the content of sphingolipids in the airways and/or lungs of a subject can be increased by at least 10%, or 15%, or 20%, or 25%, or 30%, or 35%, or 40%, or 45%, or 50%, or 55%, or 60%, or 65%, or 70%, or 75%, or 80%, or 85%, or 90%, or 100% by use of the methods and agents described herein. The content of sphingolipids in the airways and/or lungs of a subject can be increased 2-fold or more. For example, the content of sphingolipids in the airways and/or lungs of a subject can be increased by 3-fold, 5-fold, 7-fold, 8-fold, 9-fold, 10-fold or more.

Administration of such agents can reduce airway constriction in a subject having an asthma episode or prone to having an asthma episode by at least 10%, or 15%, or by 20%, or 25%, or 30%, or 35%, or 40%, or 45%, or 50%, or 55%, or 60%, or 65%, or 70%, or 75%, or 80%, or 85%, or 90%, or 100% by use of the methods and agents described herein.

Administration of such agents can reduce the force needed for air intake by a subject having an asthma episode or prone to having an asthma episode by at least 10%, or 15%, or 20%, or 25%, or 30%, or 35%, or 40%, or 45%, or 50%, or 55%, or 60% by use of the methods and agents described herein.

Treatment of Subjects

Subjects that can benefit from treatment with the agents described herein (e.g., cystic fibrosis transmembrane conductance regulator (CFTR) inhibitors, dihydroceramide reductase inhibitors, and/or substrates for serine palmitoyl-CoA transferase (SPT)) include mammals currently prone to asthma attacks, mammals having an asthma episode, as well as mammals suspected of developing asthma. Subjects that can be treated include mammals such as domestic, agricultural and zoo animals. Humans with a propensity or probability of having an asthma episode are preferred subject.

In some instances, subjects with ORMDL3 polymorphisms and/or those whose asthma is responsive to MgSO$_4$ therapy can also benefit from treatment with the agents described herein (e.g., cystic fibrosis transmembrane conductance regulator (CFTR) inhibitors, dihydroceramide reductase inhibitors, and substrates for serine palmitoyl-CoA transferase (SPT)). Hence, one step in asthma treatment can include determining whether a given subject suffering an asthma attack will respond to magnesium (e.g., MgSO$_4$) therapy (for example, by observing whether a subject has an impaired magnesium-induced relaxation response). Another step that can be performed independently of an evaluation of the subject's magnesium responsiveness, can include determining whether a subject has polymorphisms in the 17Q21 chromosomal locus or in the ORMDL3 gene locus. For example, the polymorphism can be Rs 7216389 (T allele), rs 8076131 (A allele), rs 4378650 (C allele), rs 3744246 (C allele), rs12603332 (C allele), and/or rs 3859192 (C allele) (see, EP2006687, WO2008155396, and US2011046202, as well as Galanter et al., Am J Respir Crit Care Med. 177(11): 1194-1200 (2008), each of which is specifically incorporated herein in its entirety).

Compositions

Any of the compounds described herein, including agents that increase sphingolipid synthesis or reduce airway constriction, can be formulated into compositions for administration to a subject who suffers from asthma, who is having an asthma episode, or who is suspected of having or developing asthma. Any compound or mixture of compounds that can increase sphingolipid synthesis or reduce airway constriction can be provided in a composition. Such compounds include any of those described herein and can include, for example, cystic fibrosis transmembrane conductance regulator (CFTR) inhibitors, dihydroceramide reductase inhibitors, and substrates for serine palmitoyl-CoA transferase (SPT). The compositions and methods described herein may not primarily increase sphingosine-1P levels.

The compositions can include one compound, or two compounds, or three compounds, or four compounds, or five compounds selected from cystic fibrosis transmembrane conductance regulator (CFTR) inhibitors, dihydroceramide reductase inhibitors, or substrates for serine palmitoyl-CoA transferase (SPT).

The compositions of the invention can be pharmaceutical compositions. In some embodiments, the compositions can include a pharmaceutically acceptable carrier. By "pharmaceutically acceptable" it is meant that a carrier, diluent, excipient, solvent and/or salt is compatible with the other ingredients of the formulation, and is not deleterious to the recipient thereof. The compositions can be formulated in any convenient form.

In some embodiments, the therapeutic agents of the invention are administered in a "therapeutically effective amount" within the compositions. Such a therapeutically effective amount is an amount sufficient to obtain the desired physiological effect, such as a reduction of at least one symptom of a asthma, or reduction of the frequency or severity of an asthma attack. For example, the compounds can reduce airway resistance (Rn) and/or reduce the frequency or severity of an asthma attack by at least 5%, or 10%, or 15%, or 20%, or 25%, or 30%, or 35%, or 40%, or 45%, or 50%, or 55%, or 60%, or 65%, or %70, or 80%, or 90%, 095%, or 97%, or 99%, or any numerical percentage between 5% and 100%. Symptoms of asthma can include airway hyper-reactivity, airway constriction, increased force needed for lung ventilation, and/or reduced relaxation of bronchial rings. Symptoms of asthma can also include coughing, wheezing, shortness of breath, chest pain, chest tightness, reduction in lung inflation, reduction in lung deflation and combinations thereof.

To achieve the desired effect(s), the compounds and combinations thereof, may be administered as single or divided dosages. For example, the compounds can be administered in dosages of at least about 0.001 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, the compound chosen for administration, the severity of disease, the weight, the physical condition, the health, and the age of the subject. Such factors can be readily determined by the clinician employing animal models or other test systems that are available in the art.

The compounds described herein can be formulated into compositions that contain other anti-asthma agents such as corticosteroids, long-acting beta-agonists, short-acting beta-agonists, leukotriene modifiers, mast cell stabilizers, theophylline, immunomodulators, anticholinergics and the like.

Other therapeutic agents can also be included in the compositions. The compositions can also contain other ingredients such as chemotherapeutic agents, anti-viral agents, anti-fungal agents, antibacterial agents, antimicrobial agents and/or preservatives. For example, antibacterial agents such as antibiotics, antibodies, beta-lactam antibiotics, antibacterial enzymes, protein synthesis inhibitors, biocides, peptides, lantibiotics, lanthione-containing molecules, and combinations thereof can be combined with one or more of the compounds described herein to generate a composition useful for treating asthma. Examples of antibacterial agents that can be combined with the compounds described herein include ampicillin, chloramphenicol, ciprofloxacin, cotrimoxazole, lysostaphin (an enzyme first identified in *Staphylococcus simulans*), macrolides, penicillin, quinoline, sulfisoxazole, sulfonamides, aminoglycosides, tetracyclines, vancomycin, and combinations thereof. The compositions can contain one or more of the compounds described herein with any such antibacterial agents.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the therapeutic agents and compositions of the invention may be essentially continuous over a preselected period of time or may be in a series of spaced doses. Both local and systemic administration is contemplated. For example, the compositions can be administered to the subject's airways.

To prepare the composition, the compound(s) and other agents are synthesized or otherwise obtained, purified as necessary or desired. These compound(s) and other agents can be suspended in a pharmaceutically acceptable carrier and/or lyophilized or otherwise stabilized. These compound(s) can be adjusted to an appropriate concentration, and optionally combined with other agents. The absolute weight of a given compound and/or other agent included in a unit dose can vary widely. For example, about 0.01 to about 2 g, or about 0.1 to about 500 mg, of at least one compound and/or other agent, or a plurality of compounds and/or other agents can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the compounds of the invention can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

Suitable treatment regimens for treatment can also include one-time, monthly, weekly, daily or multiple daily treatments.

It will be appreciated that the amount of compounds and/or other agents for use in treatment will vary not only with the particular carrier selected but also with the route of administration, the nature of the bacterial infection being treated or inhibited, and the age and condition of the patient. Ultimately the attendant health care provider can determine proper dosage. In addition, a pharmaceutical composition can be formulated as a single unit dosage form.

The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system. For example the compounds can be linked to a convenient carrier such as a nanoparticle or be supplied in prodrug form. The compounds and/or agents may also be formulated for sustained release (for example, using microencapsulation, see WO 94/07529, and U.S. Pat. No. 4,962,091).

Thus, one or more suitable unit dosage forms comprising the compound(s) and/or agent(s) can be administered by a variety of routes including parenteral (including subcutaneous, intravenous, intramuscular and intraperitoneal), oral, rectal, dermal, transdermal, intrathoracic, intrapulmonary and intranasal (respiratory) routes.

The compositions of the invention may be prepared in many forms that include aqueous solutions, suspensions, tablets, hard or soft gelatin capsules, and liposomes and other slow-release formulations, such as shaped polymeric gels. Administration of compounds can also involve parenteral or local administration of the in an aqueous solution or sustained release vehicle.

It may be useful to formulate the compositions for intrapulmonary and intranasal (respiratory) routes of administration. Local administration to airways and/or the lungs can be employed. For example, administration can be intraesophageal, intranasal, intrabronchial (e.g., via bronchoscope), or a combination thereof.

For example, the compositions can be formulated as inhalants or aerosols to be administered via inhalation. The compounds of the present invention can be formulated into containers that include pressurized acceptable propellants such as dichlorodifluoromethane, propane, nitrogen and the like. The compositions can also be formulated for administration via a nebulizer or other lung inhalation device.

Liquid pharmaceutical compositions may be in the form of, for example, aqueous or oily suspensions, solutions, emulsions, syrups or elixirs, dry powders for constitution with water or other suitable vehicle before use. Such liquid pharmaceutical compositions may contain conventional additives such as suspending agents, emulsifying agents, non-aqueous vehicles (which may include edible oils), or preservatives. The pharmaceutical compositions may take such forms as suspensions, solutions, or emulsions in oily or aqueous vehicles, and may contain formulatory agents such as suspending, stabilizing and/or dispersing agents. Suitable carriers include saline solution and other materials commonly used in the art. The compounds can be formulated in dry form (e.g., in freeze-dried form), in the presence or absence of a carrier. If a carrier is desired, the carrier can be included in the pharmaceutical formulation, or can be separately packaged in a separate container, for addition to the compound that is packaged in dry form, in suspension or in soluble concentrated form in a convenient liquid.

The compounds and/or other agents can also be administered in an oral dosage form. Such an oral dosage form can be formulated such that the compounds and/or other agents are released in the stomach or into the intestine after passing through the stomach. Examples of methods for preparing formulations that release in the intestine are described, for example, in U.S. Pat. No. 6,306,434 and in the references contained therein.

A compound can be formulated for parenteral administration (e.g., by injection, for example, bolus injection or continuous infusion) and may be presented in unit dosage form in ampoules, prefilled syringes, small volume infusion containers or multi-dose containers with an added preservative.

Definitions

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralalkyl groups are alkyl groups as defined above in which a hydrogen or carbon bond of an alkyl group is replaced with a bond to an aryl group as defined above. Representative aralkyl groups include benzyl and phenyl-ethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

In general, "substituted" refers to an organic group as defined herein in which one or more bonds to a hydrogen atom contained therein are replaced by one or more bonds to a non-hydrogen atom such as, but not limited to, a deuterium, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

Halo refers to halogen, for example, F, Cl, Br, or I.

The present description is further illustrated by the following examples, which should not be construed as limiting in any way. The contents of all cited references (including literature references, issued patents, published patent applications as cited throughout this application) are hereby expressly incorporated by reference.

EXAMPLE 1: General Experiment Methods

This Example describes some of the materials and methods use in the development of the invention.

Study Design.

Each experimental group included a minimum of five animals or bronchial rings per condition. Experiments assessing bronchial reactivity were performed three times. Experiments assessing SL composition, gene expression and inflammation were performed at least two times. The study was not blinded/randomized. The lung histological sections were evaluated by two different investigators in a blinded fashion.

Mice Studies.

Animal studies described herein were conducted under protocols approved by the Institutional Animal Care and Use Committee of Weill Cornell Medical College. Female BALB/c mice, obtained from Taconic Farms (Tarrytown, N.Y.). Animals were housed under specific pathogen-free conditions and used at 6 to 8 weeks of age. Myriocin (Enzo Life Sciences, Plymouth Meeting, Pa.) was freshly prepared from a 10 mM stock solution to a 1 mM or 100 µM solution in 0.9% saline and 0.05% fatty acid free bovine serum albumin and 50 µl were administered intranasally. Control animals received the vehicle solution (1% DMSO in 0.9% saline, 0.5% BSA) or were naïve. Three hours later the animals underwent pulmonary function testing and were sacrificed. Heterozygous SPT-deficient mice (Sptlc2$^{+/-}$) or homozygous controls (Sptlc2$^{+/+}$) were bred, identified by genotyping using procedures like those described by Hojjati et al. (2005) and used at 6-8 weeks of age.

Tissue Sphingolipid Analyses.

Lungs were harvested following perfusion with phosphate-buffered saline (PBS, Invitrogen, Carlsbad, Calif.) containing 0.6 mM ethylenediamine tetra acetic acid dipotassium salt dehydrate (EDTA, Invitrogen) via the right ventricle to remove blood cells from the pulmonary circulation. The lungs were then homogenized in normal PBS. De-novo sphingolipid synthesis was assessed by evaluating incorporation of $^3$H-serine (24.1 Ci/mmol, Perkin Elmer (Boston, Mass.) into ceramide and sphingosine. Sphingolipid synthesis through the recycling pathway was assessed by evaluating incorporation of $^3$H-sphingosine (18.2 Ci/mmol, Perkin Elmer (Boston, Mass.) into ceramide and sphingomyelin. In both assays, equal amounts of fresh lung homogenates were incubated for 30 min at 37° C. with 2 µl of the radioactive tracer, followed by lyophilization to determine dry weight, lipid extraction with chloroform/methanol/water (1:1:0.9). The organic phase was evaporated, dissolved in 50 µl chloroform/methanol (1:1) spotted on thin-liquid chromatography plates (TLC) (Merck Silica gel 60, Darmstadt, Germany) and chromatographed for 25 min with chloroform-methanol-ammonium hydroxide (65: 25:4 v/v). Ceramides, sphingomyelin, phosphatidylserine, sphinganine and sphingosine, all dissolved at 1 µg/µl were run as standards. The lipids were identified according to their Rf values after visualization in an iodine vapor tank. The TLC plate was cut at the corresponding lipid spot, mixed with scintillation fluid (Ultima Gold, Packard Instrument Company, CT) and analyzed in a scintillation counter (Perkin Elmer Wallac, Gaithersburg, Md.). Results are calculated as dpm/mg protein.

Sphinganine, sphingosine, sphinganine-1-phosphate, sphingosine-1-phosphate, ceramides (Cer16, Cer18, Cer20, Cer22, Cer24:1, Cer24) were quantified in lung homogenates by ultra-performance liquid chromatography-tandem mass spectrometry (UPLC-MS/MS), on a Waters Xevo, equipped with a Waters BEH Phenyl UPLC Column (AC-QUITY UPLC BEH Phenyl Column, 3.0×100 mm, 1.7 µm and a ACQUITY BEH Phenyl VanGuard Pre-column, 2.1×5 mm, 1.7 µm in the Columbia University Lipid Core as reported by Shaner et al. (2009) with minor modifications. 120 nm of an internal standard mix (Avanti Polar Lipids, Mix 1) in ethanol, 0.5 ml methanol and 0.25 ml chloroform were added to the lyophilized lung homogenates and sonicated for 12 h at 48° C. After centrifugation at 10,000 g for 5 min, the supernatant was evaporated in a glass tube and resuspended in 100 µl methanol. 10 µl were injected into the UPLC-MS/MS. Results are calculated as pmol/mg.

Lung Mechanics and Airway Reactivity.

Mice were anaesthetized with pentobarbital (100 mg/kg; American Pharmaceutical Partners, Los Angeles, Calif.), tracheostomized and mechanically ventilated at a rate of 150 breaths/min, a tidal volume of 10 ml/kg and positive end-expiratory pressure of 2-3 cm H$_2$O using a computer-controlled animal ventilator (Sireq, Montreal, Canada).

Three perturbations were used to assess baseline respiratory mechanics and the effects were analyzed using the Flexivent software (Scireq):

(1) Static compliance was determined using the Salazar-Knowles equation (Colebatch et al., J Appl Physiol 46:387-393 (1971) to the plateau pressure measurements obtained between total lung capacity and functional residual capacity;

(2) Single-frequency forced oscillations were applied to determine tissue resistance (R), elastance (E) and dynamic compliance (C) using a single compartment model;

(3) Broadband forced oscillations were applied to determine Newtonian (airway) resistance (Rn), tissue damping (G) and tissue elastance using a constant phase model. Rn and G were also assessed following increasing doses of methacholine (3.125, 12.5 and 50 mg/ml).

To directly assess bronchial reactivity bronchi were dissected from myriocin treated mice, Sptlc2$^{+/-}$ or naïve mice, and mounted on hooks in a multiwire myograph system (DMT, Ann Arbor, Mich.) where they were kept at a resting tension of 200-250 mg in Krebs Henseleit (KH) solution at 37° C. (95% $O_2$, 5% $CO_2$). In addition, bronchial rings from naïve mice were bathed in myriocin (10 µM) for 3 h in the myograph before analysis. Mechanical forces were measured isometrically with force transducers interfaced to a data acquisition system (ADInstruments, Colorado Springs, Colo.) and analyzed with LabChart6Pro for Windows. Potassium (80 mM) was used to achieve maximum contraction and methacholine (0.01-10 µM) was added 30 min after washout of the $K^+$ solution. Contractile responses were measured as percentage of the response to $K^+$.

Human bronchial tissues were obtained from patients (n=15) undergoing surgery for lung cancer. The study was approved by the IRB at Weill Cornell Medical College. Within 30 min following resection, segments of bronchi with an inner diameter of 3-5 mm were taken from areas as far removed from the malignancy as possible. Bronchi were placed in oxygenated KH and following removal of adhering fat and connective tissues four to eight rings of the same bronchus were prepared. Each set of bronchial rings was suspended under an initial tension of 300-350 mg in KH solution containing 0.01% BSA, bubbled with 95% $O_2$ and 5% $CO_2$ at 37° C. and then washed every 15 min for 1 h. $K^+$ solution (80 mM) was then used to achieve maximum contraction and myriocin (10 µM) or solvent was added 30 min after washout of the $K^+$ solution. Methacholine (0.01-1 µM) was added after 90 minutes. Experiments were conducted on parallel groups of four rings at a time. Contractile responses were measured and analyzed as for the murine rings.

Assessment of Inflammation.

BAL was collected by intratracheal instillations of PBS (2×0.5 ml). Cell differentials were determined by Giemsa stain on cytospin preparations. Cell viability was determined by trypan blue exclusion. Expression of TNF-α, IL-6 and IL-1β in the lung was quantified by TaqMan RealTime RT-PCR. RNA was extracted using TRIzol (Invitrogen). Following reverse transcription of 3 µg RNA, IL-6, TNF-α or IL-1β mRNAs were amplified using probes specific for IL6 (Mm00445197_m1), IL1β (Mm00445197_m1) or TNF-α (Mm00445197_m1; all from Applied Biosystems, Carlsbad, Calif.). RNA levels were quantified using the ΔΔCt method and normalized to expression of murine ribosomal 18s (4310893E, Applied Biosystems). For lung histology, lungs were inflated with 4% paraformaldehyde at 25 cm $H_2O$ and 5 µm paraffin sections were stained with hematoxylin and eosin (H&E).

Lung $Mg^{2+}$ Homeostasis and on Bronchial Response to Magnesium ($Mg^{2+}$).

RNA levels of the $Mg^{2+}$ transporter TRPM6 and TRMP7 were analyzed by real-time RT-PCR using probes for TRMP6 (Mm00445197_m1) or TRMP7 (Mm00445197_m) and quantified as described above. Total $Mg^{2+}$ levels in BAL, lung homogenates and serum were determined on an Olympus AU2700™ Analyzer. In this method $Mg^{2+}$ is reacted with xylidyl blue in a strongly basic solution where calcium interference is eliminated by glycoletherdiamine-N,N,N',N'-tetraacetic acid (GEDTA). The color produced is measured bichromatically at 520/800 nm. It is proportional to the magnesium concentration. To assess bronchial reactivity following administration of $Mg^{2+}$, 154 mg of isotonic $MgSO_4$ was nebulized to Sptlc2 mice or mice that had received myriocin, followed by nebulization of methacholine and determination of airway resistance as described above. The effect of $Mg^{2+}$ supplementation on methacholine-induced contraction of bronchial rings was analyzed by adding $MgSO_4$ (15 mM) to the myograph bath solution following stimulation with methacholine (10 µM).

ORMDL Expression.

RNA was extracted from lungs using TRIzol (Invitrogen). Following reverse transcription of 3 µg RNA, ORMDL1, 2 and 3 mRNAs were amplified using the following primers and probes (Roche Applied Science):

```
ORMDL1:
                        (forward; SEQ ID NO: 1)
5'-GGGAATTGTCCTGTGACCAG, (reverse; SEQ ID NO: 2)
5'-CACTGTGGGCAACTCCAAC
probe 17 (#04686900001);

ORMDL2:
                        (forward; SEQ ID NO: 3)
5'-TCCTGGAGACCACAGGTGTA, (reverse; SEQ ID NO: 4)
5'-AGCTTGTTCCCCAGCTGTC
probe 92 (#04692098001);

ORMDL3:
                        (forward; SEQ ID NO: 5)
5'-CCCTCACCAACCTTATCCAC, (reverse; SEQ ID NO: 6)
5'-GGACCCCGTAGTCCATCTG
probe 109 (#04692284001).
```

RNA levels were quantified using the ΔΔCt method and normalized to expression of murine ribosomal 18s (4310893E, Applied Biosystems).

Mucus Production.

Lung sections were stained with periodic acid-Schiff stain (PAS) and analyzed by light microscopy. Expression of MUC5ac (Mm01276735) was quantified by TaqMan Real-Time RT-PCR as described above.

Airway Remodeling.

Lung sections were stained with Masson's Trichrome and analyzed by light microscopy. Epithelial and collagen layer thickness was quantified in 100-200 µm bronchi using Metamorph software (Sunnyvale, Calif.).

Statistics.

Data points from individual assays are presented as mean±standard error of the mean (SEM). Comparisons between two groups were conducted by one-way unpaired two sample t-test. Comparisons of more than two groups and the pulmonary function tests were conducted by two-way repeated measures ANOVA with Bonferroni post-hoc comparison. All experiments were done with matched control conditions.

EXAMPLE 2: Reduced Sphingolipid Synthesis Induces Airway Hyper-Reactivity

This Example provides data showing that impaired sphingolipid synthesis in the respiratory tract induces airway hyper-reactivity.

Impaired Respiratory Tract SPT Alters Pulmonary Sphingolipid Composition

Figure 1F:
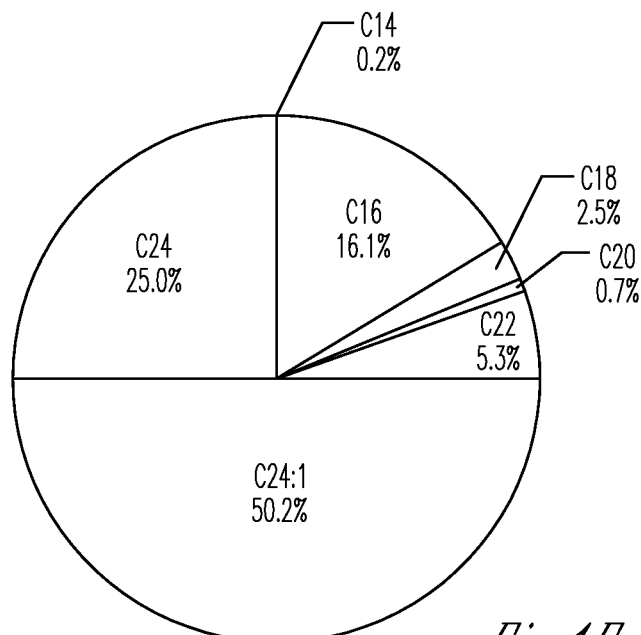
Figure 1G:
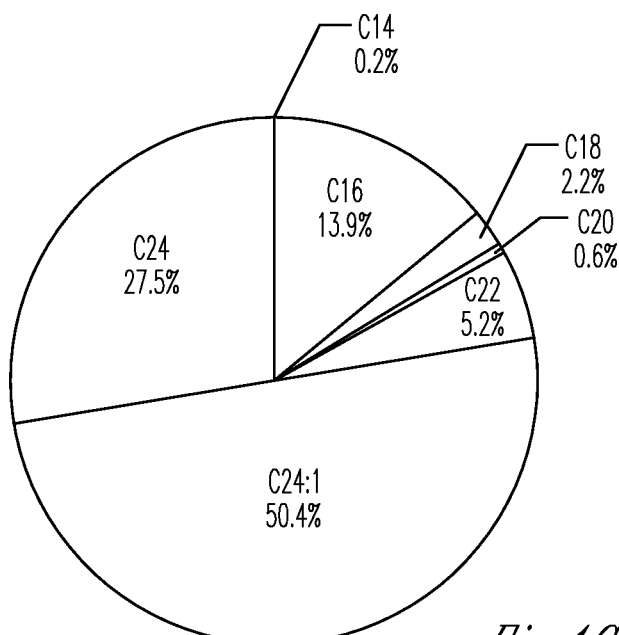

Myriocin is a potent and specific inhibitor of SPT that affects SPT independent of orm. To assess if direct administration of myriocin to the respiratory tract affects pulmonary sphingolipid synthesis, the lung sphingolipid composition was determined by ultra-performance liquid chromatography-tandem mass spectrometry (UPLC-MS/MS) 3 h following intranasal administration of myriocin. As shown in FIG. 1, myriocin reduced sphinganine in the lung (FIG. 1A). While sphingosine (FIG. 1B), sphinganine-1P (Sa1P; FIG. 1C) and sphingosine-1P (S1P; FIG. 1D) levels were not significantly decreased, the sum of ceramides (C14, C16, C18, C20, C22, C24, C24:1) was decreased by myriocin treatment (FIG. 1E-1G). Certain ceramides were also individually decreased by myriocin (compare FIGS. 1F and 1G).

Figure 2F:
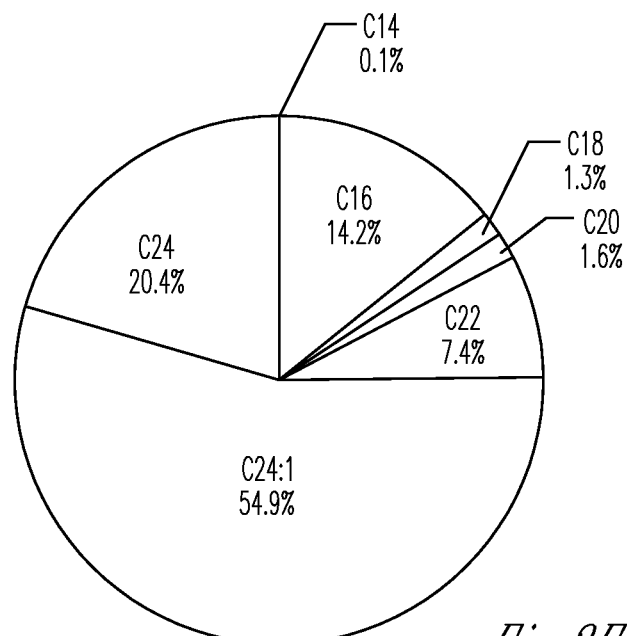
Figure 2G:
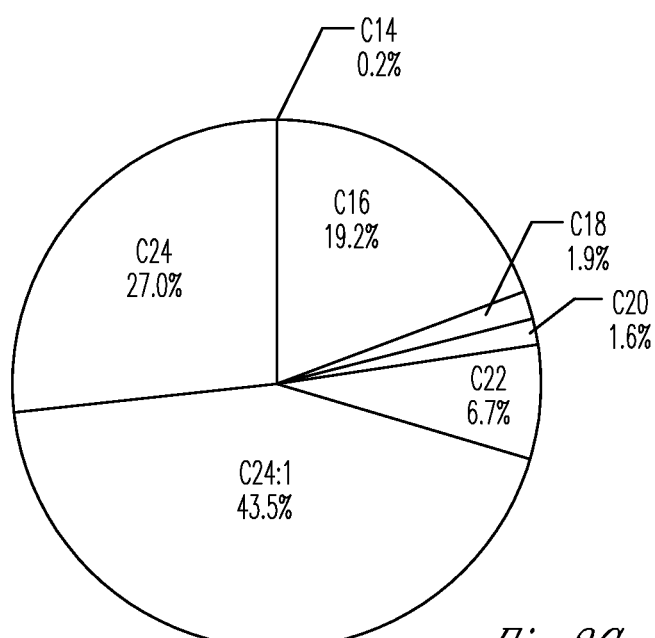

The sphingolipid composition of lungs from genetic SPT-deficient Sptlc2$^{+/-}$ mice was then evaluated. Sptlc2 codes for one of the three subunits of SPT (Lowther et al., *Biochem. Soc. Trans.* 40, 547-554 (2010)). Homozygous knockout of the gene is embryonically lethal. Heterozygous Sptlc2$^{+/-}$ mice have 60% decreased hepatic SPT activity, decreased hepatic sphinganine, ceramides and sphingosine and decreased serum ceramides and sphingosine levels but no other apparent phenotype (Hojjati et al., *Biochim. Biophys. Acta* 1737, 44-51 (2005)). As shown in FIG. 2A, sphinganine levels were reduced in lungs of Sptlc2$^{+/-}$ mice ($p<0.05$). FIG. 2E-2G show that the sum of all measured ceramides was also decreased in lungs of Sptlc2$^{+/-}$ mice ($p<0.05$), and individually the C22 and C24:1 ceramides were lower in the Sptlc2$^{+/-}$ mice. Sphingosine (FIG. 2B), sphinganine-1P (FIG. 2C), and sphingosine-1P (FIG. 2D) were not significantly altered in lungs of Sptlc2$^{+/-}$ mice. These date indicate that both acute and chronic partial SPT deficiency in the respiratory tract affects lung sphingolipid composition.

Figure 2H:
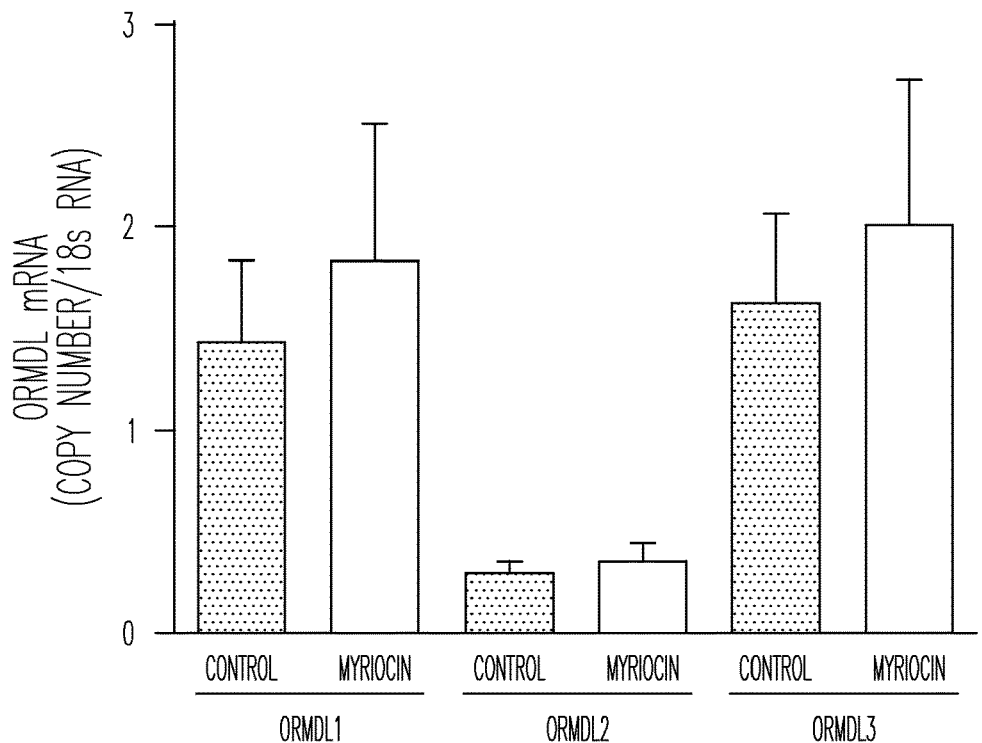
Figure 2I:
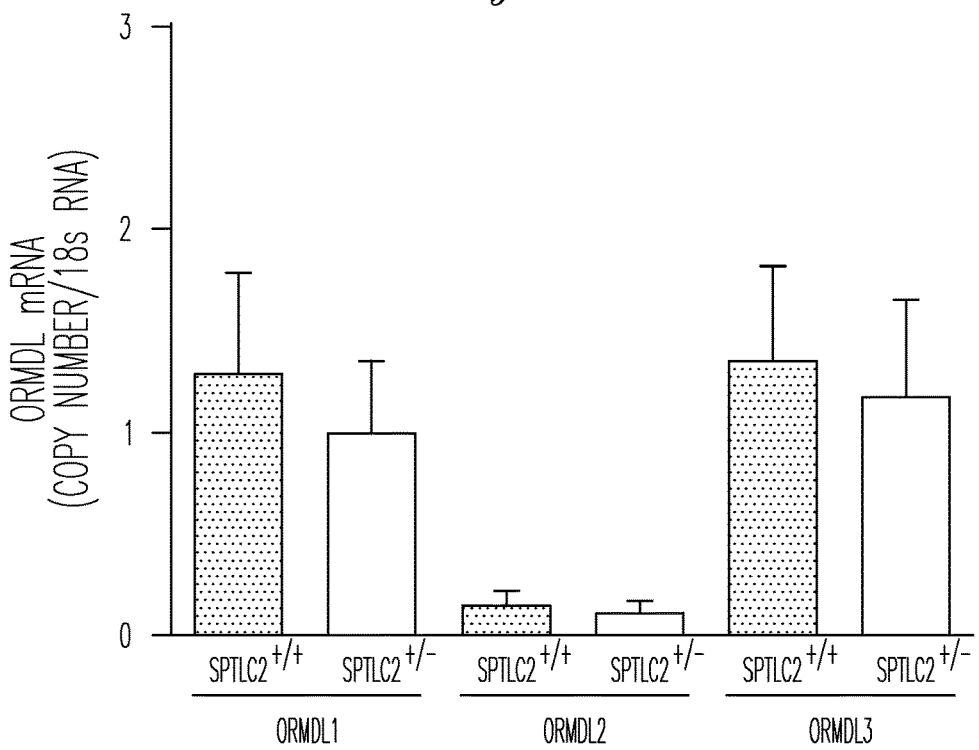

To assess if ORMDL expression was altered with decreased activity of SPT, mRNA expression of ORMDL1, 2 and 3 in lung tissue was analyzed following myriocin treatment and in the Sptlc2$^{+/-}$ mice. Expression of ORMDL1, 2 or 3 was not affected by myriocin (FIG. 2H) or by genetic SPT deficiency (FIG. 2I).

Impaired SPT in the Respiratory Tract Results in Bronchial Hyper-Reactivity

Experiments were then performed to assess if administration of myriocin directly to the respiratory tract affects pulmonary function. Myriocin (2 or 20 µg) was administered intranasally to BALB/c mice. Airway resistance (Rn) in response to increasing doses of inhaled methacholine was determined 3 h after myriocin administration. As shown in FIG. 3A, airway reactivity was increased at 3 h following myriocin administration. Baseline lung mechanical properties, such as static compliance (FIG. 3B), were not altered. Application of myriocin directly to the respiratory tract increased contractile responses of bronchial rings isolated from these mice (FIG. 3C) in a dose-dependent manner (FIG. 3D). Similar results were obtained with human bronchial rings that were kept for 90 min in a myriocin-containing bath solution (FIG. 3E).

Airway resistance in response to methacholine in Sptlc2$^{+/-}$ compared to Sptlc2$^{+/+}$ controls was also increased (FIG. 3F). No differences were detected in the baseline mechanical lung parameters, including static compliance (FIG. 3G). Moreover, contractile response to methacholine was increased in bronchial rings isolated from Sptlc2$^{+/-}$ mice compared to bronchial rings isolated from Sptlc2$^{+/+}$ controls (FIG. 3H). These data indicate that acute or chronic partial SPT deficiency in the respiratory tract increases airway reactivity.

Decreased SPT Activity in the Lung is not Associated with Increased Inflammation, Increased Mucus Production or Airway Remodeling Experiments were next performed to assess if inflammation is associated with decreased SPT activity in the respiratory tract. The number of cells in BAL from Sptlc2$^{+/-}$ mice was similar to Sptlc2$^{+/+}$ controls (FIG. 4A), but a small increase in the number of neutrophils was seen in the BAL of myriocin-treated animals (FIG. 4B). No inflammatory changes were seen in lung sections of Sptlc2$^{+/-}$ mice (FIG. 4C) or myriocin-treated mice (FIG. 4D). No increases in expression of the inflammatory cytokines IL-6 (FIG. 4E), IL-1β (FIG. 4F) or TNF-α (FIG. 4G) were observed in the lungs of Sptlc2$^{+/-}$ mice compared to Sptlc2$^{+/+}$ controls, or in myriocin-treated mice compared to controls (FIG. 4H-J). However, 11-6 expression was less in Sptlc2$^{+/-}$ mice (FIG. 4E) and TNF-α expression was less in the myriocin-treated mice (FIG. 4J). These data indicate that decreased SPT activity in the lung is not associated with increased inflammation.

Increased mucus production and airway remodeling are other major features associated with asthma. No differences in mucus-producing cells were seen on PAS-stained lung sections of myriocin-treated mice (FIG. 4K) and Sptlc2$^{+/-}$ mice (FIG. 4L). Expression of Muc5ac, a marker to assess mucus production in mice (Oguma et al., *J. Immunol.* 187, 999-1005 (2011)), was unchanged in both, myriocin-treated mice and Sptlc2$^{+/-}$ mice (FIG. 4K-4L).

To evaluate if chronic reduction of de-novo-sphingolipid synthesis is associated with airway remodeling, the thickness of the airways was assessed in the Sptlc2$^{+/-}$ mice. Thickness of the α-SMA positive smooth muscle cell layers (FIG. 4M) or thickness of the collagen layer (FIG. 4N) in 100-200 µm bronchi was comparable between Sptlc2$^{+/-}$ mice and controls.

Decreased SPT Activity in the Lung is Associated with Altered Magnesium Homeostasis Short-chain ceramides and sphingomyelin are reported to increase intracellular magnesium concentration in cultured vascular smooth muscle cells (Zheng et al., *Am. J. Physiol.* 300, H486-492 (2011)). Experiments were designed to assess if inhibition of SPT could lead to alterations in cellular magnesium homeostasis in the respiratory tract. TRPM7 is a universally expressed regulator of cellular magnesium homeostasis (Ryazanova et al., *Nat. Commun.* 1, 109 (2010); Schmitz et al., *Cell* 114, 191-200 (2003); Touvz, *Am. J. Physiol.* 294, H1103-1118 (2008)). As shown in FIG. 5A, expression of TRPM7 was increased in the lungs of Sptlc2$^{+/-}$ mice and mice that had received myriocin. The expression of TRPM6, the "gatekeeper" in transepithelial magnesium transport (Groenestege et al., *J. Am. Soc. Nephrol.* 17, 1035-1043 (2006)), was not altered (data not shown). Total serum and lung magnesium levels were also unaffected in Sptlc2$^{+/-}$ mice. However, lung magnesium levels were reduced in myriocin-treated mice (FIG. 5B). Interestingly, when bronchial rings isolated from mice that had received myriocin intranasal were stimulated with methacholine prior to addition of MgSO$_4$, the magnesium-induced relaxation of the rings was impaired (FIG. 5C). A similar pattern was seen in bronchial rings isolated from Sptlc2$^{+/-}$ mice (FIG. 5D). These data indicate that decreased SPT activity in the respiratory tract alters magnesium homeostasis and the response of the airways to magnesium.

The data described in this Example demonstrate that sphingolipid synthesis is associated with airway hyperactivity, a key feature of asthma. Two mouse models provide proof that sphingolipid synthesis is associated with airway hyperactivity: haploinsufficient Sptlc2$^{+/-}$ mice and mice that had inhaled myriocin, a specific inhibitor of de-novo sphingolipid synthesis. In both models, de-novo sphingolipid synthesis in the lung was not completely shut-off, but was impaired enough to decrease overall pulmonary ceramide and sphinganine content, consistent with inhibited de-novo sphingolipid synthesis. Interestingly, the expression of ORMDL1, 2 and 3 was not altered in the lungs of Sptlc2$^{+/-}$ mice or following myriocin administration.

Increased airway reactivity was not associated with inflammation, mucus hyperplasia or airway remodelling, other key features of asthma. However, the phenotype in both models was associated with altered magnesium homeostasis and an altered response of the airways to magnesium Inhibition with myriocin and genetic SPT deficiency both impaired the relaxing effect of MgSO$_4$ in methacholine-induced bronchoconstriction.

Accordingly, SPT expression and sphingolipid levels influence magnesium homeostasis and hyperreactivity of respiratory airways.

EXAMPLE 3: Increased Sphingolipid Synthesis Reduces Airway Hyper-Reactivity

This Example provides data showing that cystic fibrosis transmembrane conductance regulator (CFTR) inhibitors enhance the concentration of sphingolipid intermediates in tracheal epithelial cells and alleviate bronchial hyper-reactivity.
Methods
GlyH-101 (50 µM) was added to culture media of cystic fibrosis tracheal cells, non-cystic fibrosis tracheal cells or A549 cells (a lung epithelial cell line).

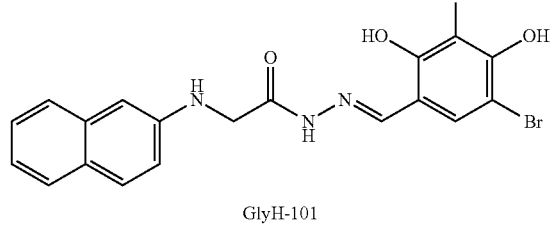

GlyH-101

Sphinganine, an intermediate of de-novo sphingolipid synthesis, was quantified in cell lysates by LC-MS/MS.

In another experiment, bronchial rings were isolated from Sptlc2$^{+/-}$ or Sptlc2$^{+/+}$ mice and mounted in a myograph. CFTR inhibitor GlyH-101 or the solvent DMSO (control) were added to the bath solution. After 2 hr contractile responses of the rings stimulated with methacholine (10 mM) were determined.

To evaluate if increasing sphingolipid synthesis in the respiratory tract would alleviate the increased bronchial responsiveness of SPT-deficient airways, the CFTR inhibitor GlyH-101 was administered directly to the respiratory tract of Sptlc2$^{+/+}$ and Sptlc2$^{+/-}$ mice via the intranasal route. Control mice received diluent only. The bronchial reactivity of these animals was evaluated three hours after methacholine administration (which induces contraction of bronchi). Results FIG. 6A-6B show that sphinganine levels increase in cultured respiratory epithelial cells when GlyH-101 was added. Sphinganine is a sphingolipid intermediate produced only via the de-novo sphingolipid synthesis pathway (FIG. 8). Cells from the trachea of cystic fibrosis patients have increased baseline levels of sphinganine that are not altered by addition of GlyH-101 to the culture medium (FIG. 6A). GlyH-101 is an inhibitor of CFTR, which is a electrolyte channel expressed in bronchial and vascular smooth muscle cells.

As shown in FIG. 6E, GlyH-101 alleviated the airway resistance occurring in Sptlc2$^{+/-}$ mice after administration of the bronchial constriction agent methacholine. GlyH-101 had no effect on bronchial reactivity of control Sptlc2$^{+/+}$ mice (FIG. 6D). In contrast, in Sptlc2$^{+/-}$ mice the elevated bronchial reactivity decreased following administration on GlyH-101 (FIG. 6E).

These data indicate that the increased de-novo sphingolipid synthesis induced by short-term inhibition of CFTR leads to decreased bronchial reactivity in mice that are deficient in SPT. GlyH-101 and other compounds that increase de-novo sphingolipid synthesis can be an effective therapeutic strategy for individuals with asthma.

EXAMPLE 4: Increased Sphingolipid Synthesis Reduces Airway Hyper-Reactivity

This Example provides data showing that increasing the activity of SPT alleviates bronchial hyper-reactivity.
Methods
Fenretinide (N-(4-hydroxyphenyl)retinamide) is a synthetic retinoid that inhibits the dihydroceramide desaturase and increases the activities of SPT and ceramide synthase (Fabrias et al., *Progr Lipid Res* 51:82-94 (2012)).

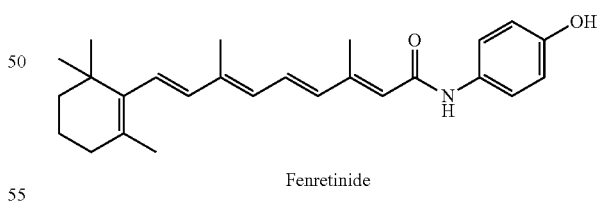

Fenretinide

Human bronchial epithelial cells were incubated with either myriocin (1 µM) or fenretinide (10 µM) for 3 hours. The amounts of sphingolipids were then quantified by mass spectrometry.
Results
As shown in FIG. 7, the sum of all dihydroceramides was increased in cells treated with fenretinide. Dihydroceramides are intermediates of only the de-novo pathway of sphingolipid synthesis (FIG. 8).

The viability of the cells was not affected by fenretinide or myriocin. Fenretinide can induce cell death at doses as low as 5 µM in cancer cells (Wang et al. *Cancer Res* 61:5102-5 (2001)), but toxicity is usually not seen in doses up to 12 µM in non-malignant cells (Li et al., *Cancer Letters* 284:175-81 (2009); O'Donnell et al., *Leukemia* 16:902-10 (2002)). Accordingly, low doses of fenretinide may effectively alleviate bronchial hyper reactivity.

REFERENCES

1. H. Bisgaard, K. Bonnelykke, P. M. Sleiman, M. Brasholt, B. Chawes, E. Kreiner-Moller, M. Stage, C. Kim, R. Tavendale, F. Baty, C. B. Pipper, C. N. Palmer, H. Hakonarsson, Chromosome 17q21 gene variants are associated with asthma and exacerbations but not atopy in early childhood. *Am. J. Respir. Crit. Care Med.* 179, 179-185 (2009).
2. E. Bouzigon, E. Corda, H. Aschard, M. H. Dizier, A. Boland, J. Bousquet, N. Chateigner, F. Gormand, J. Just, N. Le Moual, P. Scheinmann, V. Siroux, D. Vervloet, D. Zelenika, I. Pin, F. Kauffmann, M. Lathrop, F. Demenais, Effect of 17q21 variants and smoking exposure in early-onset asthma. *N. Engl. J. Med.* 359, 1985-1994 (2008).
3. J. Galanter, S. Choudhry, C. Eng, S. Nazario, J. R. Rodriguez-Santana, J. Casal, A. Torres-Palacios, J. Salas, R. Chapela, H. G. Watson, K. Meade, M. LeNoir, W. Rodriguez-Cintron, P. C. Avila, E. G. Burchard, ORMDL3 gene is associated with asthma in three ethnically diverse populations. *Am. J. Respir. Crit. Care Med.* 177, 1194-1200 (2008).
4. E. Halapi, D. F. Gudbjartsson, G. M. Jonsdottir, U. S. Bjornsdottir, G. Thorleifsson, H. Helgadottir, C. Williams, G. H. Koppelman, A. Heinzmann, H. M. Boezen, A. Jonasdottir, T. Blondal, S. A. Gudjonsson, T. Thorlacius, A. P. Henry, J. Altmueller, M. Krueger, H. D. Shin, S. T. Uh, H. S. Cheong, B. Jonsdottir, B. R. Ludviksson, D. Ludviksdottir, D. Gislason, C. S. Park, K. Deichmann, P. J. Thompson, M. Wjst, I. P. Hall, D. S. Postma, T. Gislason, A. Kong, I. Jonsdottir, U. Thorsteinsdottir, K. Stefansson, A sequence variant on 17q21 is associated with age at onset and severity of asthma. *Eur. J. Hum. Genet.* 18, 902-908 (2010).
5. M. F. Moffatt, I. G. Gut, F. Demenais, D. P. Strachan, E. Bouzigon, S. Heath, E. von Mutius, M. Farrall, M. Lathrop, W. O. Cookson, A large-scale, consortium-based genomewide association study of asthma. *N. Engl. J. Med.* 363, 1211-1221 (2010).
6. M. F. Moffatt, M. Kabesch, L. Liang, A. L. Dixon, D. Strachan, S. Heath, M. Depner, A. von Berg, A. Bufe, E. Rietschel, A. Heinzmann, B. Simma, T. Frischer, S. A. G. Willis-Owen, K. C. C. Wong, T. Illig, C. Vogelberg, S. K. Weiland, E. von Mutius, G. R. Abecasis, M. Farrall, I. G. Gut, G. M. Lathrop, W. O. C. Cookson, Genetic variants regulating ORMDL3 expression contribute to the risk of childhood asthma. *Nature* 448, 470-473 (2007).
7. C. Ober, T. C. Yao, The genetics of asthma and allergic disease: a 21st century perspective. *Immunol. Rev.* 242, 10-30 (2011).
8. P. M. Sleiman, K. Annaiah, M. Imielinski, J. P. Bradfield, C. E. Kim, E. C. Frackelton, J. T. Glessner, A. W. Eckert, F. G. Otieno, E. Santa, K. Thomas, R. M. Smith, W. Glaberson, M. Garris, S. Gunnlaugsson, R. M. Chiavacci, J. Allen, J. Spergel, R. Grundmeier, M. M. Grunstein, M. Magnusson, H. Bisgaard, S. F. Grant, H. Hakonarson, ORMDL3 variants associated with asthma susceptibility in North Americans of European ancestry. *J. Allergy Clin. Immunol.* 122, 1225-1227 (2008).
9. R. Tavendale, D. F. Macgregor, S. Mukhopadhyay, C. N. Palmer, A polymorphism controlling ORMDL3 expression is associated with asthma that is poorly controlled by current medications. *J. Allergy Clin. Immunol.* 121, 860-863 (2008).
10. D. G. Torgerson, E. J. Ampleford, G. Y. Chiu, W. J. Gauderman, C. R. Gignoux, P. E. Graves, B. E. Himes, A. M. Levin, R. A. Mathias, D. B. Hancock, J. W. Baurley, C. Eng, D. A. Stern, J. C. Celedon, N. Rafaels, D. Capurso, D. V. Conti, L. A. Roth, M. Soto-Quiros, A. Togias, X. Li, R. A. Myers, I. Romieu, D. J. Van Den Berg, D. Hu, N. N. Hansel, R. D. Hernandez, E. Israel, M. T. Salam, J. Galanter, P. C. Avila, L. Avila, J. R. Rodriquez-Santana, R. Chapela, W. Rodriguez-Cintron, G. B. Diette, N. F. Adkinson, R. A. Abel, K. D. Ross, M. Shi, M. U. Faruque, G. M. Dunston, H. R. Watson, V. J. Mantese, S. C. Ezurum, L. Liang, I. Ruczinski, J. G. Ford, S. Huntsman, K. F. Chung, H. Vora, W. J. Calhoun, M. Castro, J. J. Sienra-Monge, B. del Rio-Navarro, K. A. Deichmann, A. Heinzmann, S. E. Wenzel, W. W. Busse, J. E. Gem, R. F. Lemanske, Jr., T. H. Beaty, E. R. Bleecker, B. A. Raby, D. A. Meyers, S. J. London, F. D. Gilliland, E. G. Burchard, F. D. Martinez, S. T. Weiss, L. K. Williams, K. C. Barnes, C. Ober, D. L. Nicolae, Meta-analysis of genome-wide association studies of asthma in ethnically diverse North American populations. *Nat. Genet.* 43, 887-892 (2011).
11. L. Hjelmqvist, M. Tuson, G. Marfany, E. Herrero, S. Balcells, R. Gonzalez-Duarte, ORMDL proteins are a conserved new family of endoplasmic reticulum membrane proteins. *Genome Biol.* 3, RESEARCH0027 (2002).
12. D. K. Breslow, S. R. Collins, B. Bodenmiller, R. Aebersold, K. Simons, A. Shevchenko, C. S. Ejsing, J. S. Weissman, Orm family proteins mediate sphingolipid homeostasis. *Nature* 463, 1048-1053 (2010).
13. D. K. Breslow, J. S. Weissman, Membranes in balance: mechanisms of sphingolipid homeostasis. *Mol. Cell* 40, 267-279 (2010).
14. S. Han, M. A. Lone, R. Schneiter, A Chang, Orm1 and Orm2 are conserved endoplasmic reticulum membrane proteins regulating lipid homeostasis and protein quality control. *Proc. Natl. Acad. Sci.* 107, 5851-5856 (2010).
15. Y. Sun, Y. Miao, Y. Yamane, C. Zhang, K. M. Shokat, H. Takematsu, Y. Kozutsumi, D. G. Drubin, Orm protein phosphoregulation mediates transient sphingolipid biosynthesis response to heat stress via the Pkh-Ypk and Cdc55-PP2A pathways. *Mol. Biol. Cell* 23, 2388-2398 (2012).
16. D. L. Siow, B. W. Wattenberg, Mammalian ORMDL proteins mediate the feedback response in ceramide biosynthesis. *J. Biol. Chem.* 287, 40198-40204 (2012).
17. G. Cantero-Recasens, C. Fandos, F. Rubio-Moscardo, M. A. Valverde, R. n. Vicente, The asthma-associated ORMDL3 gene product regulates endoplasmic reticulum-mediated calcium signaling and cellular stress. *Hum. Mol. Genet.* 19, 111-121 (2010).
18. K. Mahn, S. J. Hirst, S. Ying, M. R. Holt, P. Lavender, O. O. Ojo, L. Siew, D. E. Simcock, C. G. McVicker, V. Kanabar, V. A. Snetkov, B. J. O'Connor, C. Karner, D. J. Cousins, P. Macedo, K. F. Chung, C. J. Corrigan, J. P. T. Ward, T. H. Lee, Diminished sarco/endoplasmic reticulum Ca2+ ATPase (SERCA) expression contributes to airway remodelling in bronchial asthma. *Proc. Natl. Acad. Sci.* 106, 10775-10780 (2009).
19. M. Miller, A. B. Tam, J. Y. Cho, T. A. Doherty, A. Pham, N. Khorram, P. Rosenthal, J. L. Mueller, H. M. Hoffman, M. Suzukawa, M. Niwa, D. H. Broide, ORMDL3 is an inducible lung epithelial gene regulating metalloproteases, chemokines, OAS, and ATF6. *Proc. Natl. Acad. Sci.* 109, 16648-16653 (2012).
20. A. Carreras-Sureda, G. Cantero-Recasens, F. Rubio-Moscardo, K. Kiefer, C. Peinelt, B. A. Niemeyer, M. A. Valverde, R. Vicente, ORMDL3 modulates store-operated calcium entry and lymphocyte activation. *Hum. Mol. Genet.* 22, 519-530 (2013).
21. K. J. Hsu, S. E. Turvey, Functional analysis of the impact of ORMDL3 expression on inflammation and activation of the unfolded protein response in human airway epithelial cells. Allergy Asthma Clin. Immunol. 9, 4 (2013).
22. Y. Miyake, Y. Kozutsumi, S. Nakamura, T. Fujita, T. Kawasaki, Serine palmitoyltransferase is the primary target of a sphingosine-like immunosuppressant, ISP-1/myriocin. *Biochem. Biophys. Res. Commun.* 211, 396-403 (1995).
23. M. R. Hojjati, Z. Li, X. C. Jiang, Serine palmitoyl-CoA transferase (SPT) deficiency and sphingolipid levels in mice. *Biochim. Biophys. Acta* 1737, 44-51 (2005).
24. I. Petrache, V. Natarajan, L. Zhen, T. R. Medler, A. T. Richter, C. Cho, W. C. Hubbard, E. V. Berdyshev, R. M. Tuder, Ceramide upregulation causes pulmonary cell apoptosis and emphysema-like disease in mice. *Nat. Med.* 11, 491-498 (2005).
25. E. Strettoi, C. Gargini, E. Novelli, G. Sala, I. Piano, P. Gasco, R. Ghidoni, Inhibition of ceramide biosynthesis preserves photoreceptor structure and function in a mouse model of retinitis pigmentosa. *Proc. Natl. Acad. Sci.* 107, 18706-18711 (2010).
26. M. R. Hojjati, Z. Li, H. Zhou, S. Tang, C. Huan, E. Ooi, S. Lu, X. C. Jiang, Effect of myriocin on plasma sphingolipid metabolism and atherosclerosis in apoE-deficient mice. *J. Biol. Chem.* 280, 10284-10289 (2005).
27. T. S. Park, R. L. Panek, S. B. Mueller, J. C. Hanselman, W. S. Rosebury, A. W. Robertson, E. K. Kindt, R. Homan, S. K. Karathanasis, M. D. Rekhter, Inhibition of sphingomyelin synthesis reduces atherogenesis in apolipoprotein E-knockout mice. *Circulation* 110, 3465-3471 (2004).
28. J. Lowther, J. H. Naismith, T. M. Dunn, D. J. Campopiano, Structural, mechanistic and regulatory studies of serine palmitoyltransferase. *Biochem. Soc. Trans.* 40, 547-554 (2010).
29. T. Oguma, K. Asano, K. Tomomatsu, M. Kodama, K. Fukunaga, T. Shiomi, N. Ohmori, S. Ueda, T. Takihara, Y. Shiraishi, K. Sayama, S. Kagawa, Y. Natori, C. M. Lilly, K. Satoh, K. Makimura, A. Ishizaka, Induction of mucin and MUC5AC expression by the protease activity of *Aspergillus fumigatus* in airway epithelial cells. *J. Immunol.* 187, 999-1005 (2011).
30. T. Zheng, W. Li, B. T. Altura, N. C. Shah, B. M. Altura, Sphingolipids regulate [Mg2+]o uptake and [$Mg^{2+}$]i content in vascular smooth muscle cells: potential mechanisms and importance to membrane transport of Mg2+. *Am. J. Physiol.* 300, H486-492 (2011).
31. L. V. Ryazanova, L. J. Rondon, S. Zierler, Z. Hu, J. Galli, T. P. Yamaguchi, A. Mazur, A. Fleig, A. G. Ryazanov, TRPM7 is essential for $Mg^{2+}$ homeostasis in mammals. *Nat. Commun.* 1, 109 (2010).
32. C. Schmitz, A. L. Perraud, C. O. Johnson, K. Inabe, M. K. Smith, R. Penner, T. Kurosaki, A. Fleig, A. M. Scharenberg, Regulation of vertebrate cellular $Mg^{2+}$ homeostasis by TRPM7. *Cell* 114, 191-200 (2003).
33. R. M. Touyz, Transient receptor potential melastatin 6 and 7 channels, magnesium transport, and vascular biology: implications in hypertension. *Am. J. Physiol.* 294, H1103-1118 (2008).
34. W. M. Groenestege, J. G. Hoenderop, L. van den Heuvel, N. Knoers, R. J. Bindels, The epithelial Mg2+ channel transient receptor potential melastatin 6 is regulated by dietary Mg2+ content and estrogens. *J. Am. Soc. Nephrol.* 17, 1035-1043 (2006).
35. N. Hagen-Euteneuer, D. Lutjohann, H. Park, A. H. Merrill, Jr., G. van Echten-Deckert, Sphingosine 1-phosphate (S1P) lyase deficiency increases sphingolipid formation via recycling at the expense of de-novo biosynthesis in neurons. *J. Biol. Chem.* 287, 9128-9136 (2012).
36. R. Kolesnick, D. W. Golde, The sphingomyelin pathway in tumor necrosis factor and interleukin-1 signaling. *Cell* 77, 325-328 (1994).
37. H. Kume, N. Takeda, T. Oguma, S. Ito, M. Kondo, Y. Ito, K Shimokata, Sphingosine 1-phosphate causes airway hyper-reactivity by rho-mediated myosin phosphatase inactivation. *J. Pharmacol. Exp. Ther.* 320, 766-773 (2007).
38. F. Roviezzo, B. D'Agostino, V. Brancaleone, L. De Gruttola, M. Bucci, G. De Dominicis, D. Orlotti, E. D'Aiuto, R. De Palma, F. Rossi, R. Sorrentino, G. Cirino, Systemic administration of sphingosine-1-phosphate increases bronchial hyperresponsiveness in the mouse. *Am. J. Respir. Cell. Mol. Biol.* 42, 572-577 (2010).
39. F. Roviezzo, A. Di Lorenzo, M. Bucci, V. Brancaleone, V. Vellecco, M. De Nardo, D. Orlotti, R. De Palma, F. Rossi, B. D'Agostino, G. Cirino, Sphingosine-1-Phosphate/Sphingosine Kinase Pathway Is Involved in Mouse Airway Hyperresponsiveness. *Am. J. Respir. Cell. Mol. Biol.* 36, 757-762 (2007).
40. J. J. Ryan, S. Spiegel, The role of sphingosine-1-phosphate and its receptors in asthma. *Drug News Perspect.* 21, 89-96 (2008).
41. F. X. Ble, C. Cannet, S. Zurbruegg, C. Gerard, N. Frossard, N. Beckmann, A. Trifilieff, Activation of the lung S1P(1) receptor reduces allergen-induced plasma leakage in mice. *Br. J. Pharmacol.* 158, 1295-1301 (2009).
42. W. Q. Lai, H. H. Goh, Z. Bao, W. S. Wong, A. J. Melendez, B. P. Leung, The role of sphingosine kinase in a murine model of allergic asthma. *J. Immunol.* 180, 4323-4329 (2008).
43. W. Q. Lai, W. S. Wong, B. P. Leung, Sphingosine kinase and sphingosine 1-phosphate in asthma. *Biosci. Rep.* 31, 145-150 (2011).
44. T. Nishiuma, Y. Nishimura, T. Okada, E. Kuramoto, Y. Kotani, S. Jahangeer, S. Nakamura, Inhalation of sphingosine kinase inhibitor attenuates airway inflammation in asthmatic mouse model. *Am. J. Physiol.* 294, L1085-1093 (2008).
45. L. J. Dominguez, M. Barbagallo, G. Di Lorenzo, A. Drago, S. Scola, G. Morici, C. Caruso, Bronchial reactivity and intracellular magnesium: a possible mechanism for the bronchodilating effects of magnesium in asthma. *Clin. Sci.* 95, 137-142 (1998).
46. Y. Hashimoto, Y. Nishimura, H. Maeda, M. Yokoyama, Assessment of magnesium status in patients with bronchial asthma. *J. Asthma* 37, 489-496 (2000).
47. S. P. Jiang, Y. M. Wu, S. E. Guo, Z. Q. Lu, Decreased renal mRNA expression of TRPM6 is associated with hypomagnesemia in C57BL/6 asthmatic mice. *Eur. Rev. Med. Pharmacol. Sci.* 14, 935-940 (2010).

48. R. Sinert, M. Spektor, A. Gorlin, C. Doty, A. Rubin, B. T. Altura, B. M. Altura, Ionized magnesium levels and the ratio of ionized calcium to magnesium in asthma patients before and after treatment with magnesium. *Scand. J. Clin. Lab. Invest.* 65, 659-670 (2005).
49. R. Hughes, A. Goldkorn, M. Masoli, M. Weatherall, C. Burgess, R. Beasley, Use of isotonic nebulised magnesium sulphate as an adjuvant to salbutamol in treatment of severe asthma in adults: randomised placebo-controlled trial. *Lancet* 361, 2114-2117 (2003).
50. A. Kowal, B. Panaszek, W. Barg, A. Obojski, The use of magnesium in bronchial asthma: a new approach to an old problem. *Arch. Immunol. Ther. Exp.* 55, 35-39 (2007).
51. K. S. Lindeman, C. A. Hirshman, A. N. Freed, Effect of magnesium sulfate on bronchoconstriction in the lung periphery. *J. Appl. Physiol.* 66, 2527-2532 (1989).
52. G. Rolla, C. Bucca, W. Arossa, M. Bugiani, Magnesium attenuates methacholine-induced bronchoconstriction in asthmatics. *Magnesium* 6, 201-204 (1987).
53. E. J. Villeneuve, P. J. Zed, Nebulized magnesium sulfate in the management of acute exacerbations of asthma. *Ann. Pharmacother.* 40, 1118-1124 (2006).
54. R. L. Shaner, J. C. Allegood, H. Park, E. Wang, S. Kelly, C. A. Haynes, M. C. Sullards, A. H. Merrill, Jr., Quantitative analysis of sphingolipids for lipidomics using triple quadrupole and quadrupole linear ion trap mass spectrometers. *J. Lipid Res.* 50, 1692-1707 (2009).
55. B. S. Ding, D. J. Nolan, P. Guo, A. O. Babazadeh, Z. Cao, Z. Rosenwaks, R. G. Crystal, M. Simons, T. N. Sato, S. Worgall, K. Shido, S. Y. Rabbany, S. Rafii, Endothelial-derived angiocrine signals induce and sustain regenerative lung alveolarization. *Cell* 147, 539-553 (2011).
56. Fabrias G, Munoz-Olaya J, Cingolani F, Signorelli P, Casas J, et al., Dihydroceramide desaturase and dihydrosphingolipids: debutant players in the sphingolipid arena. Progr Lipid Res 51:82-94 (2012).
57. Wang H, Maurer B J, Reynolds C P, Cabot M C, N-(4-hydroxyphenyl)retinamide elevates ceramide in neuroblastoma cell lines by coordinate activation of serine palmitoyltransferase and ceramide synthase. Cancer Res 61:5102-5 (2001).
58. Li X, Ling W, Pennisi A, Khan S, Yaccoby S., Fenretinide inhibits myeloma cell growth, osteoclastogenesis and osteoclast viability. Cancer Letters 284:175-81 (2009).
59. O'Donnell P H, Guo W X, Reynolds C P, Maurer B J, N-(4-hydroxyphenyl)retinamide increases ceramide and is cytotoxic to acute lymphoblastic leukemia cell lines, but not to non-malignant lymphocytes. Leukemia 16:902-10 (2002).

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods, devices and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a reactor" or "a mixer" or "a feedstream" includes a plurality of such reactors, mixers or feedstreams (for example, a series of reactors, mixers or feedstreams), and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The following statements describe some of the elements or features of the invention.

Statements:
1. A method comprising administering to a subject with asthma, or a subject suspected of having asthma, an agent that increases sphingolipid content in the subject's airways or lungs.
2. The method of statement 1, wherein the agent is a dihydroceramide reductase inhibitor, a cystic fibrosis transmembrane conductance regulator (CFTR) inhibitor, a substrate for serine palmitoyl-CoA transferase (SPT), or a combination thereof.

3. The method of statement 1 or 2, wherein the agent is a compound of formula I:

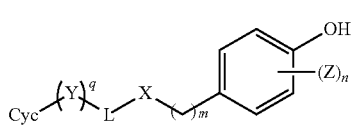

wherein:
   Cyc is aryl or cycloalkyl, optionally substituted with alkyl;
   Y is NH or O, and q is 0 or 1;
   L is alkyl or arylalkyl, wherein any alkyl optionally comprises one or more double bond, is optionally substituted with carbonyl, or both;
   X is C(O)NH—N=, C(O)NH, or NHC(O)-heteroaryl;
   m is 0 or 1, provided that when m is 1 and X is C(O)NH—N=, a carbon-nitrogen double bond is present; and
   each independently selected Z is halo or OH, n is 0, 1, 2, or 3.

4. The method of any of statements 1-3, wherein the agent is:

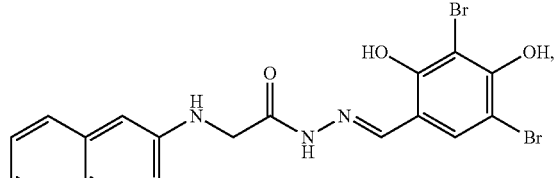

GlyH-101

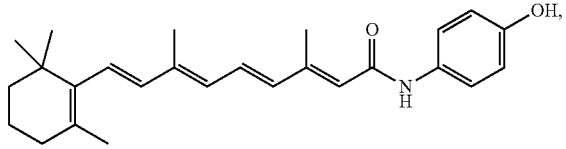

Fenretinide

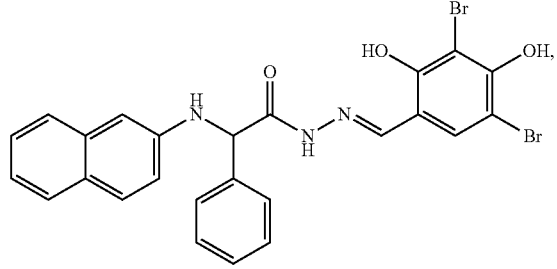

Phenyl-GlyH

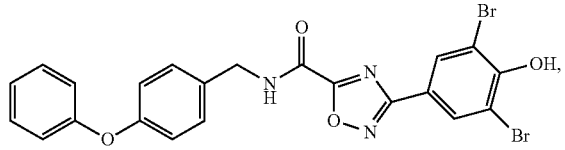

iOWH032 or
a combination thereof.

5. The method of any of statements 1-2, wherein the agent is a compound of formula II:

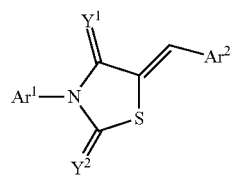

wherein
   $Y^1$ and $Y^2$ are each independently O or S;
   $Ar^1$ and $Ar^2$ are each independently aryl, wherein any aryl is optionally mono- or independently multi-substituted with carboxyl, haloalkyl, or tetrazolyl.

6. The method of any of statements 1-2 or 5, wherein the agent is:

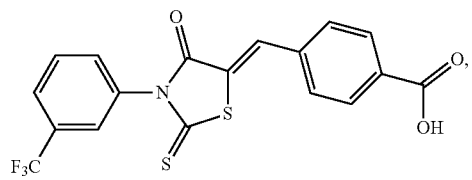

CFTR$_{inh}$-172

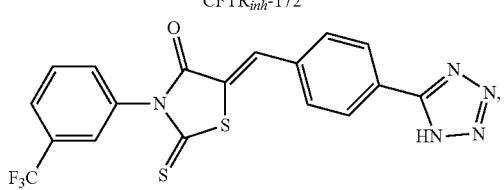

Tetrazolo-172 or
a combination thereof.

7. The method of any of statements 1-2, wherein the agent is a compound of formula III:

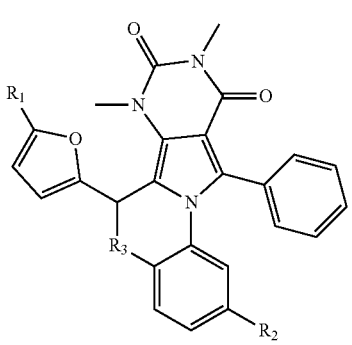

wherein:
   $R_1$ is alkyl or halo;
   $R_2$ is H or carboxyl; and
   $R_3$ is O or NH.

8. The method of any of statements 1-2 or 7, wherein the agent is:

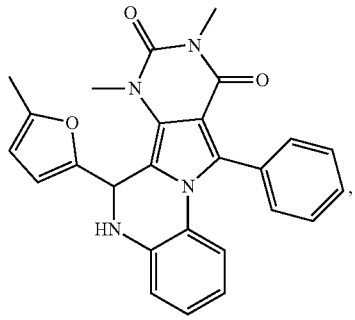
PPQ-102

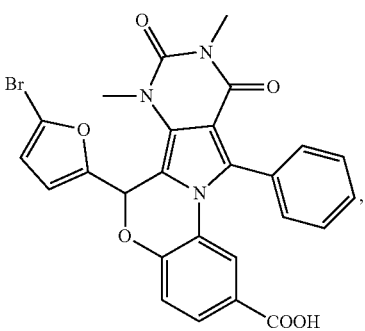
BPO-27 or
a combination thereof.

9. The method of any of statements 1-2, wherein the agent is a compound of formula IVa or IVb:

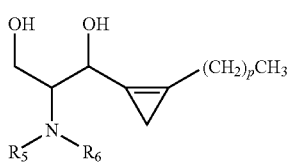
IVa

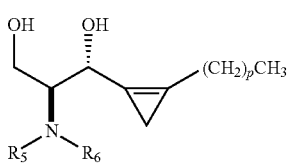
IVb wherein:

$R_5$ is —CO(CH$_2$)$_v$R$_7$, —COO(CH$_2$)$_v$R$_7$, —CONH(CH$_2$)$_v$R$_7$, —CSNH(CH$_2$)$_v$R$_7$, —COCO(CH$_2$)$_v$R$_7$;

v is an integer from 0 to 12;

$R_7$ is methyl or aryl;

$R_6$ is H or lower alkyl; and p is an integer from 8 to 16.

10. The method of any of statements 1, 2 or 9, wherein the agent is:

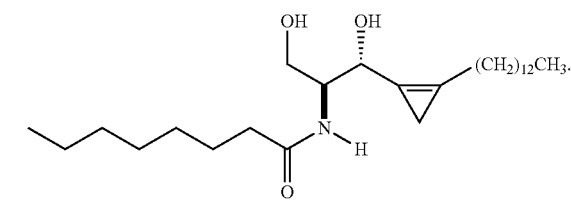
GT-11

11. The method of any of statements 1-2, wherein the agent is:

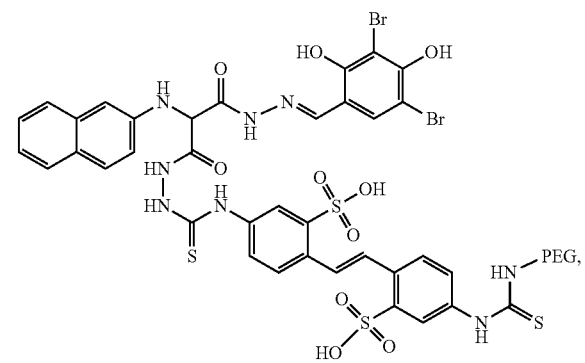
MalH-PEG

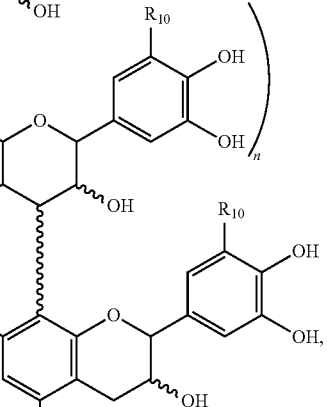
Crofelemer or
a combination thereof.

12. The method of any of statements 1-2, wherein the agent is serine, alanine, glycine or a combination thereof.

13. The method of any of statements 1-12, wherein the agent is administered in an amount that increases the content of sphingolipids in the airways and/or lungs of the subject by at least about 10%, or by 15%, or by 20%, or by 25%, or by 30%, or by 35%, or by 40%, or by 45%, or by 50%, or by 55%, or by 60%, or by 65%, or by 70%, or by 75%, or by 80%, or by 85%, or by 90%, or by 100%.
14. The method of any of statements 1-13, wherein the agent is administered in an amount that increases the content of sphingolipids in the airways and/or lungs of the subject by 2-fold or more.
15. The method of any of statements 1-14, wherein the agent is administered in an amount that increases the content of sphingolipids in the airways and/or lungs of the subject by at least about 3-fold, 5-fold, 7-fold, 8-fold, 9-fold or 10-fold.
16. The method of any of statements 1-15, wherein the agent is administered in an amount that reduces airway constriction in the subject by at least about 10%, or by 15%, or by 20%, or by 25%, or by 30%, or by 35%, or by 40%, or by 45%, or by 50%, or by 55%, or by 60%, or by 65%, or by 70%, or by 75%, or by 80%, or by 85%, or by 90%, or by 100%.
17. The method of any of statements 1-16, wherein the agent is administered in an amount that reduces the force needed for air intake by the subject by at least about 10%, or by 15%, or by 20%, or by 25%, or by 30%, or by 35%, or by 40%, or by 45%, or by 50%, or by 55%, or by 60%.
18. The method of any of statements 1-17, wherein the subject is having an asthma episode or suspected of having an asthma episode
19. The method of any of statements 1-18, wherein the subject is not responsive to magnesium administration.
20. The method of any of statements 1-19, further comprising administering magnesium to the subject.
21. The method of statement 19 or 20, wherein the magnesium is MgSO$_4$.
22. The method of any of statements 1-21, wherein the subject has a polymorphism in chromosome 17 at locus Q21 (i.e., at 17Q21).
23. The method of any of statements 1-22, further comprising determining whether the subject has a polymorphism in chromosomal region 17Q21 or in an ORMDL3 gene.
24. The method of any of statements 1-23, wherein the agent is administered to the subject if the subject is not responsive to magnesium administration or the subject has a polymorphism in chromosome 17 at locus Q21.
25. The method of any of statements 1-24, where the subject is deficient in serine palmitoyltransferase (SPT) enzyme or enzymatic activity.
26. The method of any of statements 1-25, which reduces the incidence or intensity of an asthmatic episode in a subject by at least about 10%, or by 15%, or by 20%, or by 25%, or by 30%, or by 35%, or by 40%, or by 45%, or by 50%, or by 55%, or by 60%, or by 70%, or by 80%, or by 90%, or by 95%.
27. The method of any of statement 1-26, wherein the subject is a mammal
28. The method of any of statement 1-27, where the subject is a human patient.
29. A composition comprising an agent that increases sphingolipid content in mammalian airways or lungs.
30. The composition of statement 29, formulated for oral or parenteral administration.
31. The composition of statement 29 or 30, formulated for administration to the mammalian airways and/or lungs.
32. The composition of any of statements 29-31, formulated into a container that also comprises a pressurized propellant.
33. The composition of any of statements 29-32, formulated for administration via a nebulizer or other lung inhalation device.
34. The composition of any of statements 29-33, wherein the agent is a dihydroceramide reductase inhibitor, a cystic fibrosis transmembrane conductance regulator (CFTR) inhibitor, a substrate for serine palmitoyl-CoA transferase (SPT), or a combination thereof.
35. The composition of any of statements 29-34, wherein the agent is a compound of formula I:

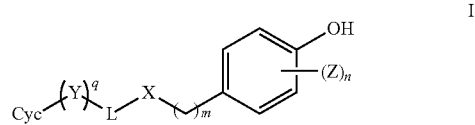

wherein:
Cyc is aryl or cycloalkyl, optionally substituted with alkyl;
Y is NH or O, and q is 0 or 1;
L is alkyl or arylalkyl, wherein any alkyl optionally comprises one or more double bond, is optionally substituted with carbonyl, or both;
X is C(O)NH—N=, C(O)NH, or NHC(O)-heteroaryl;
m is 0 or 1, provided that when m is 1 and X is C(O)NH—N=, a carbon-nitrogen double bond is present; and
each independently selected Z is halo or OH, n is 0, 1, 2, or 3.
36. The composition of any of statements 29-35, wherein the agent is:

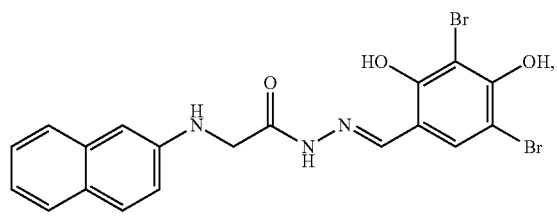

GlyH-101

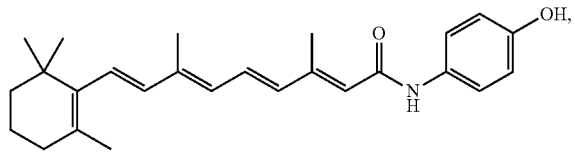

Fenretinide

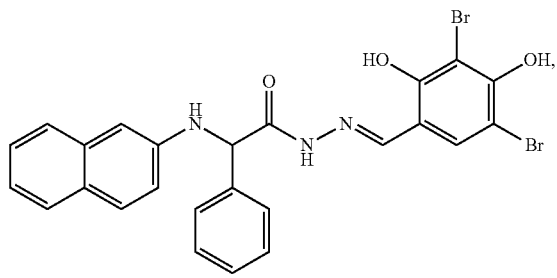

Phenyl-GlyH

-continued

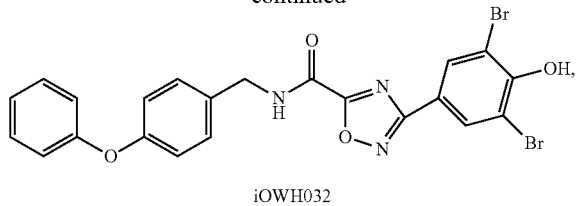

iOWH032 or
a combination thereof.

37. The composition of any of statements 29-34, wherein the agent is a compound of formula II:

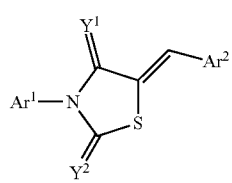

II wherein
Y$^1$ and Y$^2$ are each independently O or S;
Ar$^1$ and Ar$^2$ are each independently aryl, wherein any aryl is optionally mono- or independently multi-substituted with carboxyl, haloalkyl, or tetrazolyl.

38. The composition of any of statements 29-34 or 37, wherein the agent is:

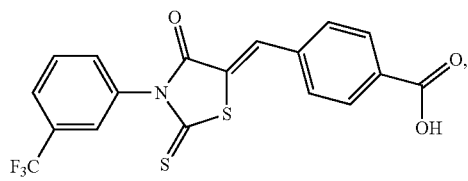

CFTR$_{inh}$-172

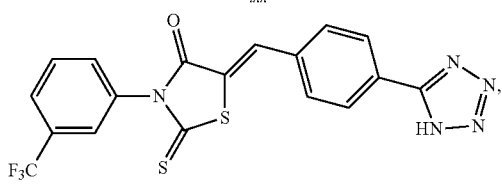

Tetrazolo-172 or
a combination thereof.

39. The composition of any of statements 29-34, wherein the agent is a compound of formula III:

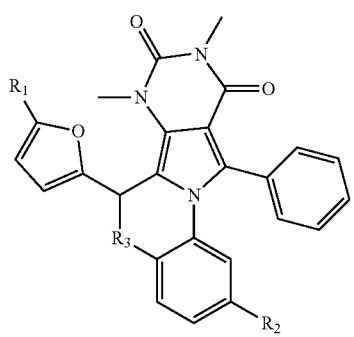

III wherein:
R$_1$ is alkyl or halo;
R$_2$ is H or carboxyl; and
R$_3$ is O or NH.

40. The composition of any of statements 29-34 or 39, wherein the agent is

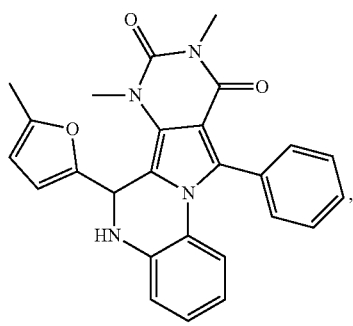

PPQ-102

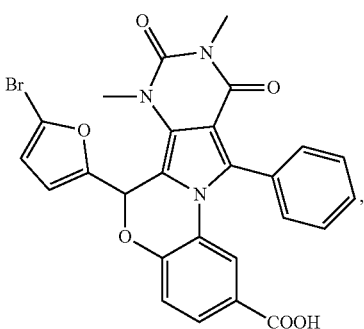

BPO-27 or
a combination thereof.

41. The composition of any of statements 29-34, wherein the agent is a compound of formula IVa or IVb:

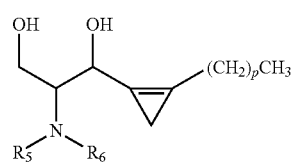

IVa

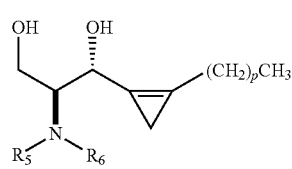

IVb wherein:
R$_5$ is —CO(CH$_2$)$_v$R$_7$, —COO(CH$_2$)$_v$R$_7$, —CONH(CH$_2$)$_v$R$_7$, —CSNH(CH$_2$)$_v$R$_7$, —COCO(CH$_2$)$_v$R$_7$;
v is an integer from 0 to 12;
R$_7$ is methyl or aryl;
R$_6$ is H or lower alkyl; and
p is an integer from 8 to 16.

42. The composition of any of statements 29-34 or 41, wherein the agent is:

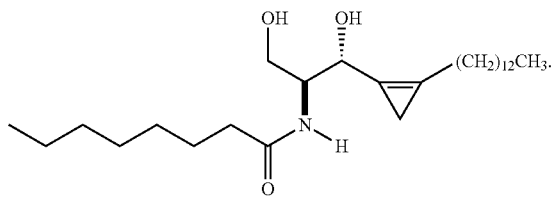

GT-11

43. The composition of any of statements 29-34, wherein the agent is:

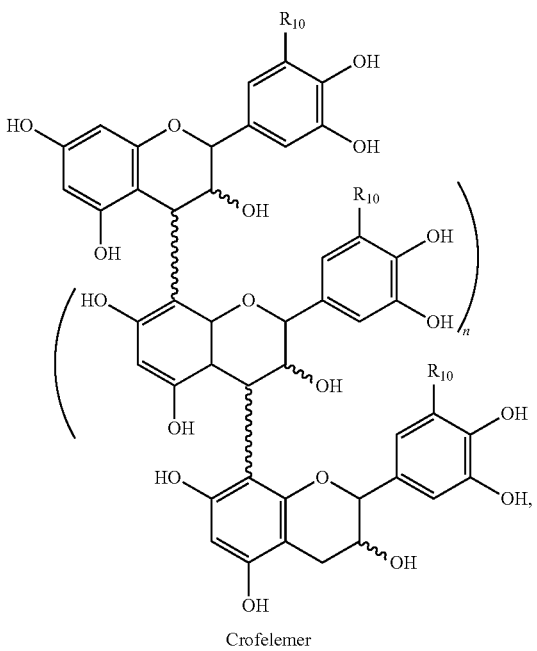

Crofelemer

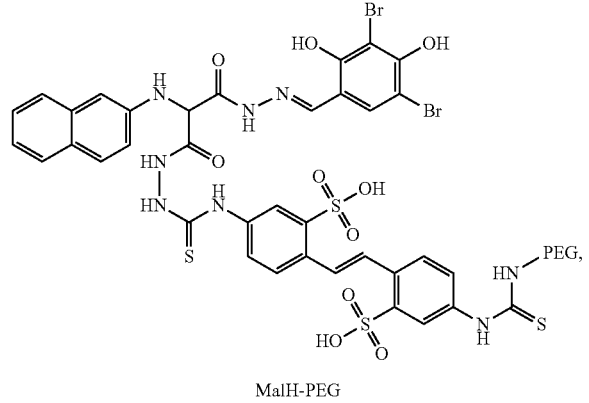

MalH-PEG or a combination thereof.

44. The composition of any of statements 29-34, wherein the agent is serine, alanine, glycine or a combination thereof.

45. The composition of any of statements 29-44, wherein the composition contains an amount of the agent that increases the content of sphingolipids in the airways and/or lungs of the subject by at least about 10%, or by 15%, or by 20%, or by 25%, or by 30%, or by 35%, or by 40%, or by 45%, or by 50%, or by 55%, or by 60%, or by 65%, or by 70%, or by 75%, or by 80%, or by 85%, or by 90%, or by 100%.

46. The composition of any of statements 29-45, wherein the composition contains an amount of the agent that increases the content of sphingolipids in the airways and/or lungs of the subject by 2-fold or more.

47. The composition of any of statements 29-46, wherein the composition contains an amount of the agent that increases the content of sphingolipids in the airways and/or lungs of the subject by at least about 3-fold, 5-fold, 7-fold, 8-fold, 9-fold or 10-fold.

48. The composition of any of statements 29-47, wherein the composition contains an amount of the agent that reduces airway constriction in the subject by at least about 10%, or by 15%, or by 20%, or by 25%, or by 30%, or by 35%, or by 40%, or by 45%, or by 50%, or by 55%, or by 60%, or by 65%, or by 70%, or by 75%, or by 80%, or by 85%, or by 90%, or by 100%.

49. The composition of any of statements 29-49, wherein the composition contains an amount of the agent that reduces the force needed for air intake by the subject by at least about 10%, or by 15%, or by 20%, or by 25%, or by 30%, or by 35%, or by 40%, or by 45%, or by 50%, or by 55%, or by 60%.

50. Use of an agent that increases sphingolipid content in mammalian airways for the treatment of asthma.

51. The use of statement 50, formulated for oral or parenteral administration.

52. The use of statement 50 or 51, formulated for administration to the mammalian airways and/or lungs.

53. The use of any of statements 50-52, formulated into a container that also comprises a pressurized propellant.

54. The use of any of statements 50-53, formulated for administration via a nebulizer or other lung inhalation device.

55. The use of any of statements 50-54, wherein the agent is a dihydroceramide reductase inhibitor, a cystic fibrosis transmembrane conductance regulator (CFTR) inhibitor, a substrate for serine palmitoyl-CoA transferase (SPT), or a combination thereof.

56. The use of any of statements 50-55, wherein the agent is a compound of formula I:

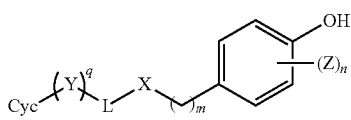

I wherein:
Cyc is aryl or cycloalkyl, optionally substituted with alkyl;
Y is NH or O, and q is 0 or 1;
L is alkyl or arylalkyl, wherein any alkyl optionally comprises one or more double bond, is optionally substituted with carbonyl, or both;
X is C(O)NH—N=, C(O)NH, or NHC(O)-heteroaryl;
m is 0 or 1, provided that when m is 1 and X is C(O)NH—N=, a carbon-nitrogen double bond is present; and
each independently selected Z is halo or OH, n is 0, 1, 2, or 3.

57. The use of any of statements 50-56, wherein the agent is:

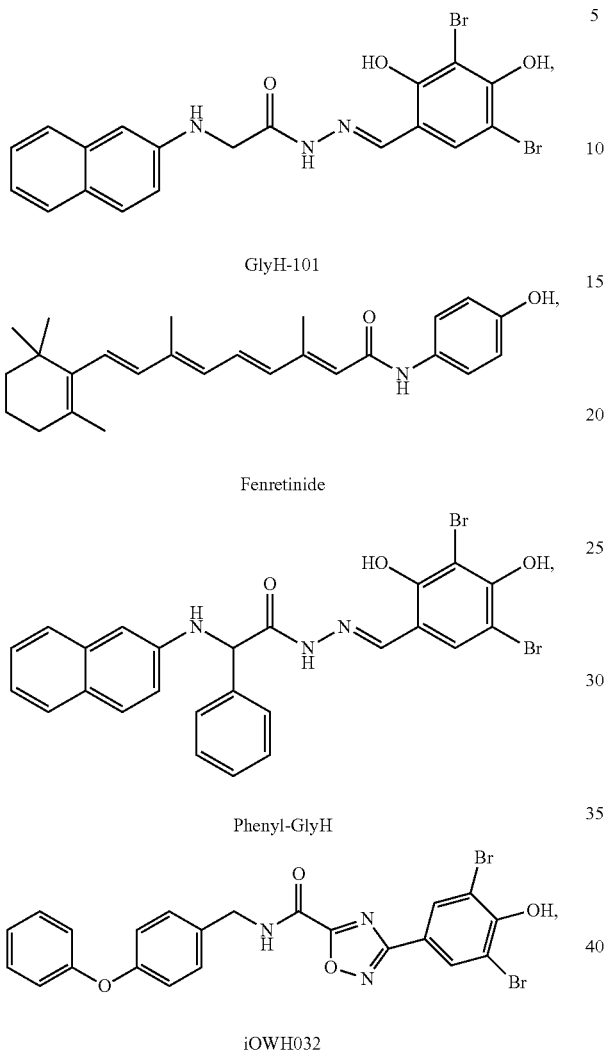

GlyH-101

Fenretinide

Phenyl-GlyH iOWH032 or
a combination thereof.

58. The use of any of statements 50-55, wherein the agent is a compound of formula II:

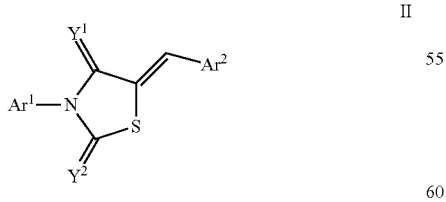

wherein
Y$^1$ and Y$^2$ are each independently O or S;
Ar$^1$ and Ar$^2$ are each independently aryl, wherein any aryl is optionally mono- or independently multi-substituted with carboxyl, haloalkyl, or tetrazolyl.

59. The use of any of statements 50-55 or 58, wherein the agent is:

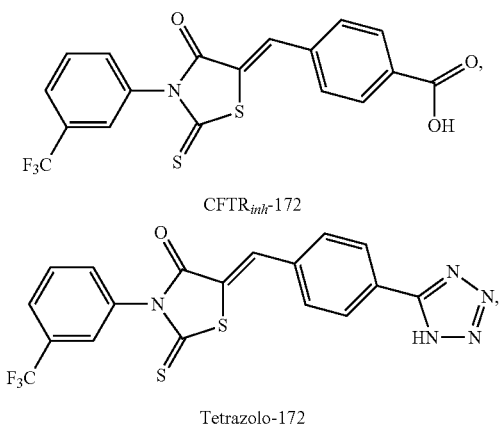

CFTR$_{inh}$-172

Tetrazolo-172 or
a combination thereof.

60. The use of any of statements 50-55, wherein the agent is a compound of formula III:

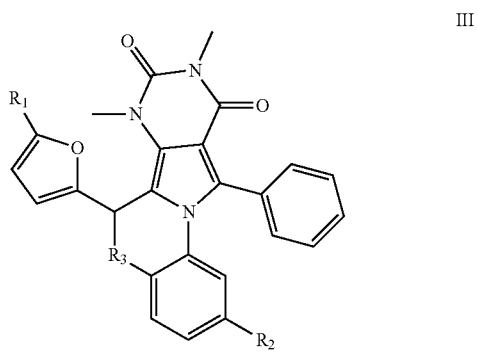

wherein:
R$_1$ is alkyl or halo;
R$_2$ is H or carboxyl; and
R$_3$ is O or NH.

61. The use of any of statements 50-55 or 60, wherein the agent is

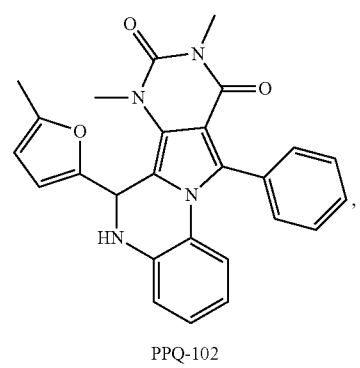

PPQ-102

47

-continued

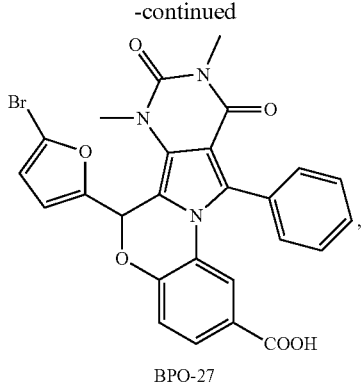

BPO-27 or a combination thereof.

62. The use of any of statements 50-55, wherein the agent is a compound of formula IVa or IVb:

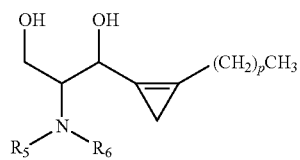

IVa

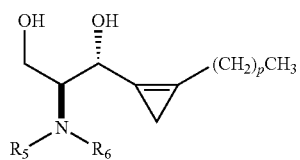

IVb wherein:

$R_5$ is —CO(CH$_2$)$_v$R$_7$, —COO(CH$_2$)$_v$R$_7$, —CONH(CH$_2$)$_v$R$_7$, —CSNH(CH$_2$)$_v$R$_7$, —COCO(CH$_2$)$_v$R$_7$;

v is an integer from 0 to 12;

$R_7$ is methyl or aryl;

$R_6$ is H or lower alkyl; and p is an integer from 8 to 16.

63. The use of any of statements 50-55 or 63, wherein the agent is:

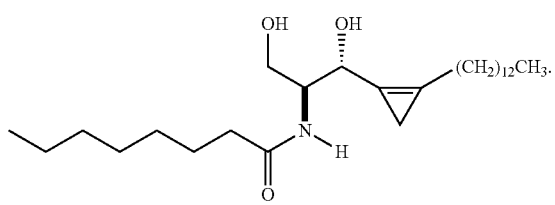

GT-11

64. The use of any of statements 50-55, wherein the agent is:

48

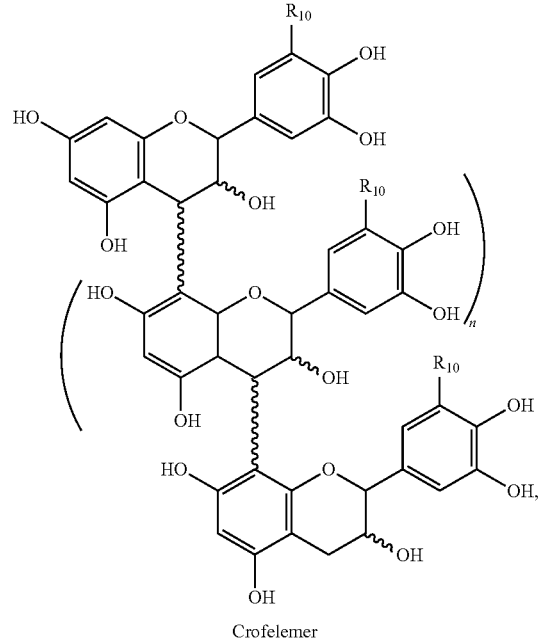

Crofelemer

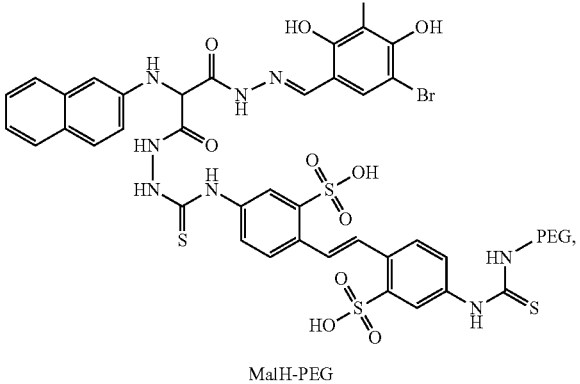

MalH-PEG or a combination thereof.

65. The use of any of statements 50-55, wherein the agent is serine, alanine, glycine or a combination thereof.

66. The use of any of statements 50-65, wherein the composition contains an amount of the agent that increases the content of sphingolipids in the airways and/or lungs of the subject by at least about 10%, or by 15%, or by 20%, or by 25%, or by 30%, or by 35%, or by 40%, or by 45%, or by 50%, or by 55%, or by 60%, or by 65%, or by 70%, or by 75%, or by 80%, or by 85%, or by 90%, or by 100%.

67. The use of any of statements 50-66, wherein the composition contains an amount of the agent that increases the content of sphingolipids in the airways and/or lungs of the subject by 2-fold or more.

68. The use of any of statements 50-67, wherein the composition contains an amount of the agent that increases the content of sphingolipids in the airways and/or lungs of the subject by at least about 3-fold, 5-fold, 7-fold, 8-fold, 9-fold or 10-fold.

69. The use of any of statements 50-68, wherein the composition contains an amount of the agent that reduces airway constriction in the subject by at least about 10%, or by 15%, or by 20%, or by 25%, or by 30%, or by 35%, or by 40%, or by 45%, or by 50%, or by 55%, or by 60%, or by 65%, or by 70%, or by 75%, or by 80%, or by 85%, or by 90%, or by 100%.

70. The use of any of statements 50-69, wherein the composition contains an amount of the agent that reduces the force needed for air intake by the subject by at least about 10%, or by 15%, or by 20%, or by 25%, or by 30%, or by 35%, or by 40%, or by 45%, or by 50%, or by 55%, or by 60%.

The following claims also summarize aspects of the invention.

What is claimed:

1. A method comprising administering to a subject with asthma GlyH-101 ((naphthalen-2-ylamino)-acetic acid (3,5-dibromo-2,4-dihydroxybenzylidene)-hydrazide), to increase the content of de novo synthesized sphinganine in the airways and/or lungs of the subject by at least about 25% and to reduce bronchial airway constriction by at least 25%.

2. The method of claim 1, wherein the subject is having an asthma episode or suspected of having an asthma episode.

3. The method of claim 1, wherein the subject is not responsive to magnesium administration.

4. The method of claim 1, wherein the subject has a polymorphism in chromosome 17 at locus Q21.

5. The method of claim 1, further comprising determining whether the subject has a polymorphism in chromosomal region 17Q21 or in an ORMDL3 gene.

6. The method of claim 1, wherein the agent is administered to the subject if the subject is not responsive to magnesium administration or the subject has a polymorphism in chromosome 17 at locus Q21.

7. The method of claim 1, which does not significantly alter sphingosine-1P levels or mucus-producing cells in the lungs.

8. The method of claim 1, wherein the agent is combined with serine, alanine, glycine, phenyl-GlyH, fenretinide, crofelemer, PPQ-102, BPO-27, $CFTR_{inh}$-172, Tetrazolo-172, MalH-PEG, iOWHO32, or a combination thereof.

* * * * *